(12) United States Patent
Chen et al.

(10) Patent No.: US 6,753,154 B1
(45) Date of Patent: Jun. 22, 2004

(54) HUMAN AZU-1 GENE, VARIANTS THEREOF AND EXPRESSED GENE PRODUCTS

(75) Inventors: Huei-Mei Chen, Richmond, CA (US); Mina Bissell, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/344,624

(22) Filed: Jun. 25, 1999

Related U.S. Application Data

(60) Provisional application No. 60/090,747, filed on Jun. 26, 1998.

(51) Int. Cl.[7] .................. G01N 33/574; G01N 33/567; C12Q 1/00; C12Q 1/68; C12P 19/26
(52) U.S. Cl. .............................. 435/7.23; 435/4; 435/6; 435/7.21; 435/84; 435/85; 435/89; 435/91.1; 435/91.2; 436/63; 436/64; 436/501; 424/9.1; 424/9.2; 424/130.1; 424/138.1; 530/300; 530/350; 530/386; 530/387.1; 530/387.9; 530/388.1; 530/388.15; 530/389.1; 530/389.7
(58) Field of Search ............................ 436/63, 64, 501; 435/4, 6, 7.21, 7.23, 84, 85, 89, 91.1, 91.2; 514/1, 2, 12, 42, 43, 44; 530/300, 350, 386, 387.1, 387.9, 388.1, 388.15, 389.1, 389.7; 424/9.1, 9.2, 130.1, 138.1

(56) References Cited

U.S. PATENT DOCUMENTS 6,342,581 B1 * 1/2002 Rosen et al.

OTHER PUBLICATIONS

Chen et al. Up–expression of a novel breast tumor suppressor candidate gene AZ1 correlates with tumorigenic reversion and cytoskeletal reorganzination. Molecular Biology of the Cell 9S:247, 1998.*
Nucleic acid database sheet for sequence 31 of U.S. Patent 6342581, Jan. 8, 1999.*
NCBI Sequence Viewer, Accession No. AF176646, amino acid and nucleic acid database sheets, Apr. 12, 2000.*
Chen et al. AZU–1: A Candidate Breast Tumor Suppressor and Biomarker for Tumor Progression. 11:1357–1367, Apr. 2000.0.*

* cited by examiner

*Primary Examiner*—Alana M. Harris
(74) *Attorney, Agent, or Firm*—Hana Verny

(57) ABSTRACT

A human AZU-1 gene, mutants, variants and fragments thereof. Protein products encoded by the AZU-1 gene and homologs encoded by the variants of AZU-1 gene acting as tumor suppressors or markers of malignancy progression and tumorigenicity reversion. Identification, isolation and characterization of AZU-1 and AZU-2 genes localized to a tumor suppressive locus at chromosome 10q26, highly expressed in nonmalignant and premalignant cells derived from a human breast tumor progression model. A recombinant full length protein sequences encoded by the AZU-1 gene and nucleotide sequences of AZU-1 and AZU-2 genes and variant and fragments thereof. Monoclonal or polyclonal antibodies specific to AZU-1, AZU-2 encoded protein and to AZU-1, or AZU-2 encoded protein homologs.

13 Claims, 25 Drawing Sheets

(3 of 25 Drawing Sheet(s) Filed in Color)

FIG. 4A

```
   1  GGAAAGCCCT TTGCACACAT CGGCCTATTG AAGCACTTTG CTTGATTCAG
  51  CTATTCTCCT CTCAGGACCT GCCTGGATCA TCCCAGCCTG TAGAATCCTG
 101  GGTTTCTGTG GCAGTTTGTT CTTCTGGTAT CACCTGCTAT GCTCTGAATG
 151  TTTGTATCCC TCTCAGCCCC GAAATTCCTG TGTTGAAATC CTAACCCCTA
 201  AGGTGATGGT ATGAGGAGGT GGGGCCTTCG GGAGGTGATT AGGCCATAAG
 251  GGCGGAGCCT TTGTGAATGG GATTAGTGCC CTTATAAAAA GAGGCCCCAC
 301  AGCACTGCCT TGCCTCTTCT GCCACGTGAA GATGCAGTGA AAGGAGCTG
 351  TCTGTGAACT TGGAAGGGGT CCTCATGAGA CACTGAACCT GCTGGTGCCT
 401  TGATCTTGGA CTTCCCAGCC TCCAGAACT//T TCACCTGTGG CAGATGATAT
 451  CATCCAGCCC GCTGCCCCTG CAGACCTGGA AAGCCCAACC TTAGCTGCCT
 501  CTTCCTACCA CAGTGATGTT GTTGGCCAGG TCTCTACGGA TCTGATAGCC
 551  CAGAGGAGTT CCGATTCTGA AGAGGCATTT GAGACCCCGG AGTCAACGAC
 601  CCCTGTCAAA GCTCCGCCAG CTCCACCCCC ACCACCCCCC GAAGTCATCC
 651  CAGAACCCGA GGTCAGCACA CAGCCACCCC CGGAAGAACC AGGATGTGGT
 701  TCTGAGACAG TCCCTGTCCC TGATGGCCCA CGGAGCGACT CGGTGGAAGG
 751  AAGTCCCTTC CGTCCCCGT CACACCCCTT CTCTGCCGTC TTCGATGAAG
 801  ACCAGCCGAT AGCCAGCAGT GGGACTTACA ACTTGGACTT TGACAACATT
 851  GAGCTTGTGG ATACCTTTCA GACCTTGGAG CCTCGTGCCT CAGACGCTAA
 901  GAATCAGGAG GGCAAAGTGA ACACACGGAG GAAGTCCACG GATTCCGTCC
 951  CCATCTCTAA GTCTACACTG TCCCGGTCGC TCAGCCTGCA AGCCAGTGAC
1001  TTTGATGGTG CTTCTTCCTC AGGCAATCCC GAGGCCGTGG CCCTTGCCCC
1051  AGATGCATAT AGCACGGGTT CCAGCAGTGC TTCTAGTACC CTTAAGCGAA
1101  CTAAAAAACC GAGGCCGCCT TCCTTAAAAA AGAAACAGAC CACCAAGAAA
1151  CCCACAGAGA CCCCCCCAGT GAAGGAGACG CAACAGGAGC CAGATGAAGA
1201  GAGCCTTGTC CCCAGTGGGG AGAATCTAGC ATCTGAGACG AAAACGGAAT
1251  CTGCCAAGAC GGAAGGTCCT AGCCCAGCCT TATTGGAGGA GACGCCCCTT
1301  GAGCCCGCTG TGGGGCCCAA AGCTGCCTGC CCTCTGGACT CAGAGAGTGC
1351  AGAAGGGGTT GTCCCCCCGG CTTCTGGAGG TGGCAGAGTG CAGAACTCAC
1401  CCCCTGTCGG GAGGAAAACG CTGCCTCTTA CCACGGCCCC GGAGGCAGGG
1451  GAGGTAACCC CATCGGATAG CGGGGGGCAA GAGGACTCTC CAGCCAAAGG
1501  GCTCTCCGTA AGGCTGGAGT TTGACTATTC TGAGGACAAG AGTAGTTGGG
1551  ACAACCAGCA GGAAAACCCC CCTCCTACCA AAAAGATAGG CAAAAAGCCA
1601  GTTGCCAAAA TGCCCCTGAG GAGGCCAAAG ATGAAAAAGA CACCCGAGAA
1651  ACTTGACAAC ACTCCTGCCT CACCTCCCAG ATCCCTGCT GAACCCAATG
1701  ACATCCCCAT TGCTAAAGGT ACTTACACCT TTGATATTGA CAAGTGGGAT
1751  GACCCCAATT TTAACCCTTT TTCTTCCACC TCAAAAATGC AGGAGTCTCC
1801  CAAACTGCCC CAACAATCAT ACAACTTTGA CCCAGACACC TGTGATGAGT
1851  CCGTTGACCC CTTTAAGACA TCCTCTAAGA CCCCCAGCTC ACCTTCTAAA
1901  TCCCCAGCCT CCTTTGAGAT CCCGGCCAGT GCTATGGAAG CCAATGGAGT
1951  GGACGGGGAT GGGCTAAACA AGCCCGCCAA GAAGAAGAAG ACGCCCCTAA
2001  AGACGGTGAA AAAGTCGCCA AAACGGTCTC CTCTCTCTGA TCCACCTTCC
2051  CAGGACCCCA CCCCAGCTGC TACACCAGAA ACACCACCAG TGATCTCTGC
2101  GGTGGTCCAC GCCACAGATG AGGAAAAGCT GGCGGTCACC AACCAGAAGT
2151  GGACGTGCAT GACAGTGGAC CTAGAGGCTG ACAAACAGGA CTACCCGCAG
2201  CCCTCGGACC TGTCCACCTT TGTAAACGAG ACCAAATTCA GTTCACCCAC
2251  TGAGGAGTTG GATTACAGAA ACTCCTATGA AATTGAATAT ATGGAGAAAA
```

FIG. 4B

```
2301  TTGGCTCCTC CTTACCTCAG GACGACGATG CCCCGAAGAA GCAGGCCTTG
2351  TACCTTATGT TTGACACTTC TCAGGAGAGC CCTGTCAAGT CATCTCCCGT
2401  CCGCATGTCA GAGTCCCCGA CGCCGTGTTC AGGGTCAAGT TTTGAAGAGA
2451  CTGAAGCCCT TGTGAACACT GCTGCGAAAA ACCAGCATCC TGTCCCACGA
2501  GGACTGGCCC CTAACCAAGA GTCACACTTG CAGGTGCCAG AGAAATCCTC
2551  CCAGAAGGAG CTGGAGGCCA TGGGCTTGGG CACCCCTTCA GAAGCGATTG
2601  AAATTAGAGA GGCTGCTCAC CCAACAGACG TCTCCATCTC CAAAACAGCC
2651  TTGTACTCCC GCATCGGGAC CGCTGAGGTG GAGAAACCTG CAGGCCTTCT
2701  GTTCCAGCAG CCCGACCTGG ACTCTGCCCT CCAGATCGCC AGAGCAGAGA
2751  TCATAACCAA GGAGAGAGAG GTCTCAGAAT GGAAAGATAA ATATGAAGAA
2801  AGCAGGCGGG AAGTGATGGA AATGAGGAAA ATAGTGGCCG AGTATGAGAA
2851  GACCATCGCT CAGATGATAG AGGACGAACA GAGAGAGAAG TCAGTCTCCC
2901  ACCAGACGGT GCAGCAGCTG GTTCTGGAGA AGGAGCAAGC CCTGGCCGAC
2951  CTGAACTCCG TGGAGAAGTC TCTGGCCGAC CTCTTCAGAA GATATGAGAA
3001  GATGAAGGAG GTCCTAGAAG GCTTCCGCAA GAATGAAGAG GTGTTGAAGA
3051  GATGTGCGCA GGAGTACCTG TCCCGGGTGA AGAAGGAGGA GCAGAGGTAC
3101  CAGGCCCTGA AGGTGCACGC GGAGGAGAAA CTGGACAGGG CCAATGCTGA
3151  GATTGCTCAG GTTCGAGGCA AGGCCCAGCA GGAGCAAGCC GCCCACCAGG
3201  CCAGCCTGCG GAAGGAGCAG CTGCGAGTGG ACGCCCTGGA AAGGACGCTG
3251  GAGCAGAAGA ATAAAGAAAT AGAAGAACTC ACCAAGATTT GTGACGAACT
3301  GATTGCCAAA ATGGGGAAAA GCTAACTCTG AACCGAATGT TTTGGACTTA
3351  ACTGTTGCGT GCAATATGAC CGTCGGCACA CTGCTGTTCC TCCAGTTCCA
3401  TGGACAGGTT CTGTTTTCAC TTTTTCGTAT GCACTACTGT ATTTCCTTTC
3451  TAAATAAAAT TGATTTGATT GTATGCAGTA CTAAGGAGAC TATCAGAATT
3501  TCTTGCTATT GGTTTGCATT TTCCTAGTAT AATTCATAGC AAGTTGACCT
3551  CAGAGTTCCT GTATCAGGGA GATTGTCTGA TTCTCTAATA AAAGACACAT
3601  TGCTGACCTT GGCCTTGCCC TTTGTACACA AGTTCCCAGG GTGAGCAGCT
3651  TTTGGATTTA ATATGAACAT GTACAGCGTG CATAGGGACT CTTGCCTTAA
3701  GGAGTGTAAA CTTGATCTGC ATTTGCTGAT TTGTTTTTAA AAAACAAGA
3751  AATGCATGTT TCAAATAAAA TTCTCTATTG TAAATAAAAT TTTTTCTTTG
3801  GATCTTGGCA ATA
```

FIG. 5A

```
   1  GGCACGAGCG ACAGTCCACA TGGTAGAAGA TGGTCCTGGG ACTTTGCTCA
  51  CACAGGGGTT CCAGGACATG TGCCAAGGTC CACGTGTGCC CCTTCTCCTC
 101  AGAGGGAGGT TTTGACTGTG CCTGAGGCCA ACAGTGAGCC CTGGACCCTT
 151  GACACGCTTG GGGGTGAAAG GAGACCCGGA GTCACTGCTG GCATCTTGGA
 201  AATGCGAAAT GCCCTGGGCA ACCAGAGCAC CCCTGCACCA CCAACTGGAG
 251  AAGTGGCAGA CACTCCCCTG GAGCCTGGCA AGGTGGCAGG CGCTGCTGGG
 301  GAAGCAGAGG GTGACATCAC CCTGAGCACA GCTGAGACAC AGGCATGTGC
 351  GTCCGGTGAT CTGCCTGAAG CAGGTACTAC GAGGACATTC TCCGTTGTGG
 401  CAGGTGACTT GGTGCTGCCA GGAAGCTGTC AGGACCCAGC CTGCTCTGAC
 451  AAGGCTCCGG GGATGGAGGG TACAGCTGCC CTTCATGGGG ACAGCCCAGC
 501  CAGGCCCCAG CAGGATAAGG AGCAGCCAGG ACCTGAGCGC CCCATTCCAG
 551  CTGGGGATGG GAAGGTGTGC GTCTCCTCAC CTCCAGAGCC TGACGAAACT
 601  CACGACCCGA AGCTGCAACA TTTGGCTCCA GAAGAGCTCC ACACTGACAG
 651  AGAGAGCCCC AGGCCTGGCC CATCCATGTT ACCTTCGGTT CCTAAGAAGG
 701  ATGCTCCAAG AGTCATGGAT AAAGTCACTT CAGATGAGAC CAGAGGTGCG
 751  GAAGGAACAG AAAG//TTCACC TGTGGCAGAT GATATCATCC AGCCCGCTGC
 801  CCCTGCAGAC CTGGAAAGCC AACCTTAGC TGCCTCTTCC TACCACAGTG
 851  ATGTTGTTGG CCAGGTCTCT ACGGATCTGA TAGCCCAGAG GAGTTCCGAT
 901  TCTGAAGAGG CATTTGAGAC CCCGGAGTCA ACGACCCCTG TCAAAGCTCC
 951  GCCAGCTCCA CCCCCACCAC CCCCCGAAGT CATCCCAGAA CCCGAGGTCA
1001  GCACACAGCC ACCCCCGGAA GAACCAGGAT GTGGTTCTGA GACAGTCCCT
1051  GTCCCTGATG GCCCACGGAG CGACTCGGTG GAAGGAAGTC CCTTCCGTCC
1101  CCCGTCACAC CCCTTCTCTG CCGTCTTCGA TGAAGACCAG CCGATAGCCA
1151  GCAGTGGGAC TTACAACTTG GACTTTGACA ACATTGAGCT TGTGGATACC
1201  TTTCAGACCT GGAGCCTCG TGCCTCAGAC GCTAAGAATC AGGAGGGCAA
1251  AGTGAACACA CGGAGGAAGT CCACGGATTC CGTCCCCATC TCTAAGTCTA
1301  CACTGTCCCG GTCGCTCAGC CTGCAAGCCA GTGACTTTGA TGGTGCTTCT
1351  TCCTCAGGCA ATCCCGAGGC CGTGGCCCTT GCCCCAGATG CATATAGCAC
1401  GGGTTCCAGC AGTGCTTCTA GTACCCTTAA GCGAACTAAA AAACCGAGGC
1451  CGCCTTCCTT AAAAAAGAAA CAGACCACCA AGAAACCCAC AGAGACCCCC
1501  CCAGTGAAGG AGACGCAACA GGAGCCAGAT GAAGAGAGCC TTGTCCCCAG
1551  TGGGGAGAAT CTAGCATCTG AGACGAAAAC GGAATCTGCC AAGACGGAAG
1601  GTCCTAGCCC AGCCTTATTG GAGGAGACGC CCCTTGAGCC CGCTGTGGGG
1651  CCCAAAGCTG CCTGCCCTCT GGACTCAGAG AGTGCAGAAG GGGTTGTCCC
1701  CCCGGCTTCT GGAGGTGGCA GAGTGCAGAA CTCACCCCCT GTCGGGAGGA
1751  AAACGCTGCC TCTTACCACG GCCCGGAGG CAGGGGAGGT AACCCCATCG
1801  GATAGCGGGG GGCAAGAGGA CTCTCCAGCC AAAGGGCTCT CCGTAAGGCT
1851  GGAGTTTGAC TATTCTGAGG ACAAGAGTAG TTGGGACAAC CAGCAGGAAA
1901  ACCCCCCTCC TACCAAAAAG ATAGGCAAAA AGCCAGTTGC CAAAATGCCC
1951  CTGAGGAGGC CAAAGATGAA AAAGACACCC GAGAAACTTG ACAACACTCC
2001  TGCCTCACCT CCCAGATCCC CTGCTGAACC CAATGACATC CCCATTGCTA
2051  AAGGTACTTA CACCTTTGAT ATTGACAAGT GGGATGACCC CAATTTTAAC
2101  CCTTTTTCTT CCACCTCAAA ATGCAGGAG TCTCCCAAAC TGCCCCAACA
2151  ATCATACAAC TTTGACCCAG ACACCTGTGA TGAGTCCGTT GACCCCTTTA
2201  AGACATCCTC TAAGACCCCC AGCTCACCTT CTAAATCCCC AGCCTCCTTT
2251  GAGATCCCGG CCAGTGCTAT GGAAGCCAAT GGAGTGGACG GGGATGGGCT
2301  AAACAAGCCC GCCAAGAAGA AGAAGACGCC CCTAAAGACG GTGAAAAGT
2351  CGCCAAAACG GTCTCCTCTC TCTGATCCAC CTTCCCAGGA CCCCACCCCA
2401  GCTGCTACAC CAGAAACACC ACCAGTGATC TCTGCGGTGG TCCACGCCAC
2451  AGATGAGGAA AAGCTGGCGG TCACCAACCA GAAGTGGACG TGCATGACAG
2501  TGGACCTAGA GGCTGACAAA CAGGACTACC CGCAGCCCTC GGACCTGTCC
2551  ACCTTTGTAA ACGAGACCAA ATTCAGTTCA CCCACTGAGG AGTTGGATTA
```

FIG. 5B

```
2601  CAGAAACTCC TATGAAATTG AATATATGGA GAAAATTGGC TCCTCCTTAC
2651  CTCAGGACGA CGATGCCCCG AAGAAGCAGG CCTTGTACCT TATGTTTGAC
2701  ACTTCTCAGG AGAGCCCTGT CAAGTCATCT CCCGTCCGCA TGTCAGAGTC
2751  CCCGACGCCG TGTTCAGGGT CAAGTTTTGA AGAGACTGAA GCCCTTGTGA
2801  ACACTGCTGC GAAAAACCAG CATCCTGTCC CACGAGGACT GGCCCCTAAC
2851  CAAGAGTCAC ACTTGCAGGT GCCAGAGAAA TCCTCCCAGA AGGAGCTGGA
2901  GGCCATGGGC TTGGGCACCC CTTCAGAAGC GATTGAAATT AGAGAGGCTG
2951  CTCACCCAAC AGACGTCTCC ATCTCCAAAA CAGCCTTGTA CTCCCGCATC
3001  GGGACCGCTG AGGTGGAGAA ACCTGCAGGC CTTCTGTTCC AGCAGCCCGA
3051  CCTGGACTCT GCCCTCCAGA TCGCCAGAGC AGAGATCATA ACCAAGGAGA
3101  GAGAGGTCTC AGAATGGAAA GATAAATATG AAGAAAGCAG GCGGGAAGTG
3151  ATGGAAATGA GGAAAATAGT GGCCGAGTAT GAGAAGACCA TCGCTCAGAT
3201  GATAGAGGAC GAACAGAGAG AGAAGTCAGT CTCCCACCAG ACGGTGCAGC
3251  AGCTGGTTCT GGAGAAGGAG CAAGCCCTGG CCGACCTGAA CTCCGTGGAG
3301  AAGTCTCTGG CCGACCTCTT CAGAAGATAT GAGAAGATGA AGGAGGTCCT
3351  AGAAGGCTTC CGCAAGAATG AAGAGGTGTT GAAGAGATGT GCGCAGGAGT
3401  ACCTGTCCCG GGTGAAGAAG GAGGAGCAGA GGTACCAGGC CCTGAAGGTG
3451  CACGCGGAGG AGAAACTGGA CAGGGCCAAT GCTGAGATTG CTCAGGTTCG
3501  AGGCAAGGCC CAGCAGGAGC AAGCCGCCCA CCAGGCCAGC CTGCGGAAGG
3551  AGCAGCTGCG AGTGGACGCC CTGGAAAGGA CGCTGGAGCA GAAGAATAAA
3601  GAAATAGAAG AACTCACCAA GATTTGTGAC GAACTGATTG CCAAAATGGG
3651  GAAAAGCTAA CTCTGAACCG AATGTTTTGG ACTTAACTGT TGCGTGCAAT
3701  ATGACCGTCG GCACACTGCT GTTCCTCCAG TTCCATGGAC AGGTTCTGTT
3751  TTCACTTTTT CGTATGCACT ACTGTATTTC CTTTCTAAAT AAAATTGATT
3801  TGATTGTATG CAGTACTAAG GAGACTATCA GAATTTCTTG CTATTGGTTT
3851  GCATTTTCCT AGTATAATTC ATAGCAAGTT GACCTCAGAG TTCCTGTATC
3901  AGGGAGATTG TCTGATTCTC TAATAAAAGA CACATTGCTG ACCTTGGCCT
3951  TGCCCTTTGT ACACAAGTTC CCAGGGTGAG CAGCTTTTGG ATTTAATATG
4001  AACATGTACA GCGTGCATAG GGACTCTTGC CTTAAGGAGT GTAAACTTGA
4051  TCTGCATTTG CTGATTTGTT TTTAAAAAAA CAAGAAATGC ATGTTTCAAA
4101  TAAAATTCTC TATTGTAAAT AAAATTTTTT CTTTGGATCT TGGCAATA
```

FIG. 6A

```
  1  MPLRRPKMKK TPEKLDNTPA SPPRSPAEPN DIPIAKGTYT FDIDKWDDPN    SPAZI
 51  FNPFSSTSKM QESPKLPQQS YNFDPDTCDE SVDPFKTSSK TPSSPSKSPA
101  SFEIPASAME ANGVDGDGLN KPAKKKKTPL KTVKKSPKRS PLSDPPSQDP    I
151  TPAATPETPP VISAVVHATD EEKLAVTNQK WTCMTVDLEA DKQDYPQPSD
201  LSTFVNETKF SSPTEELDYR NSYEIEYMEK IGSSLPQDDD APKKQALYLM
251  FDTSQESPVK SSPVRMSESP TPCSGSSFEE TEALVNTAAK NQHPVPRGLA    II
301  PNQESHLQVP EKSSQKELEA MGLGTPSEAI EIREAAHPTD VSISKTALYS
351  RIGTAEVEKP AGLLFQQPDL DSALQIARAE IITKEREVSE WKDKYEESRR
401  EVMEMRKIVA EYEKTIAQMI EDEQREKSVS HQTVQQLVLE KEQALADLNS    CCD
451  VEKSLADLFR RYEKMKEVLE GFRKNEEVLK RCAQEYLSRV KKEEQRYQAL
501  KVHAEEKLDR ANAEIAQVRG KAQQEQAAHQ ASLRKEQLRV DALERTLEQK
551  NKEIEELTKI CDELIAKMGK S
```

FIG. 6B

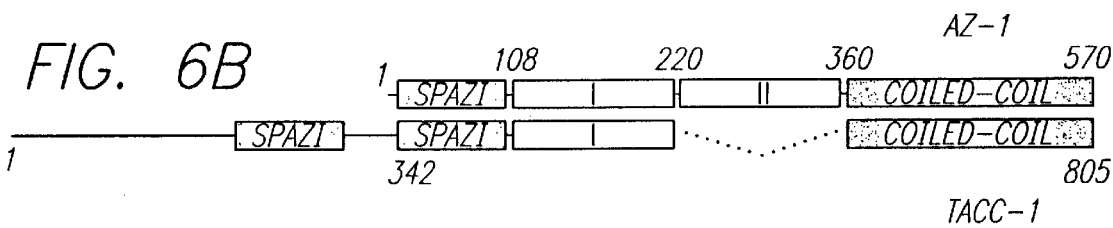

FIG. 6C

```
AZ-1     18  PASPPRSPAEPN--DIPIAKGTYTFDIDKW-----DDP--NFNPFSST
TACC1(A) 215 GNSCPELVPS-----RRSKLRKPKPVPLRK------KA--IGGEFSDT
TACC1(B) 359 KSAGLEQPTDPVARDGPLSQTSSKPDPSQW-----ESP--SFNPFGST
TACC3    344 GATSKRAPP-----RRLGERSGLKPPLRKAAVRQQKAPQEVEEDDGR
BCK1      31 SVASTKSSSK----SPRATSRKSIYDDIRS-----QFP--NLTPNSTH

AZ-1     60  SKMQESPKL--PQQSYNFDPDTCDE-SVDPFKTSSKTPSSPSKSP-AS
TACC1(A) 253 NAAVEGTPL--PKASYHFSPEELDE-NTSPLLGDARFQKSPPDIKETP
TACC1(B) 403 SVLQNSPPLS-SEGSYHFDPDNFDE-SMDPFKPTTTLTSSDFCSPTGN
TACC3    387 SGAGEDPPMPASRGSYHLDWDKMDDPNFIPFGGDTKSGCSEAQPPESP
BCK1      71 SQFYESTPV--IEQSFNWTTDDH-I-SAGTLENPTSFTNSSYKNDNGP
```

FIG. 6D

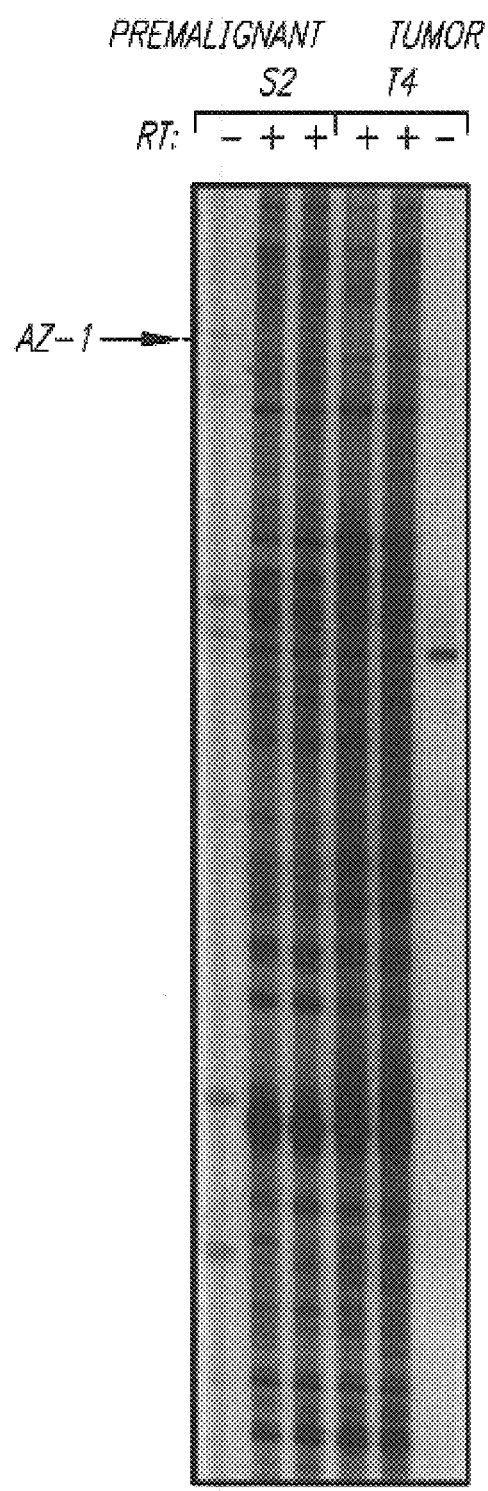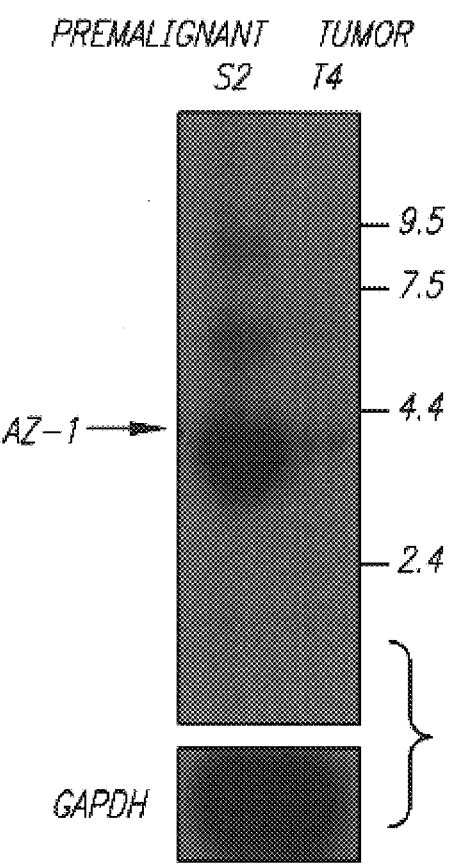
FIG. 9A
FIG. 9B

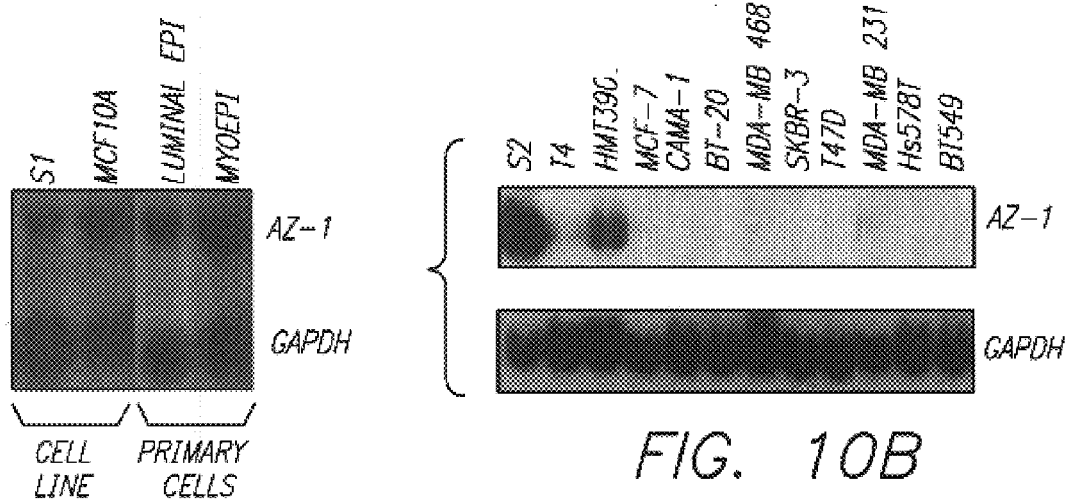
FIG. 10A
FIG. 10B
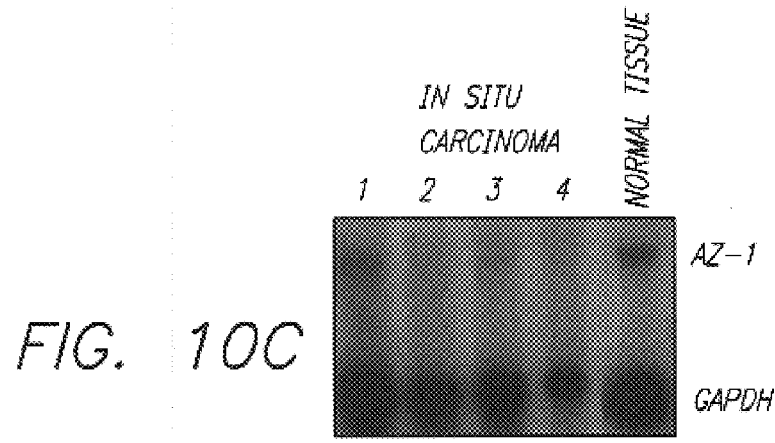
FIG. 10C
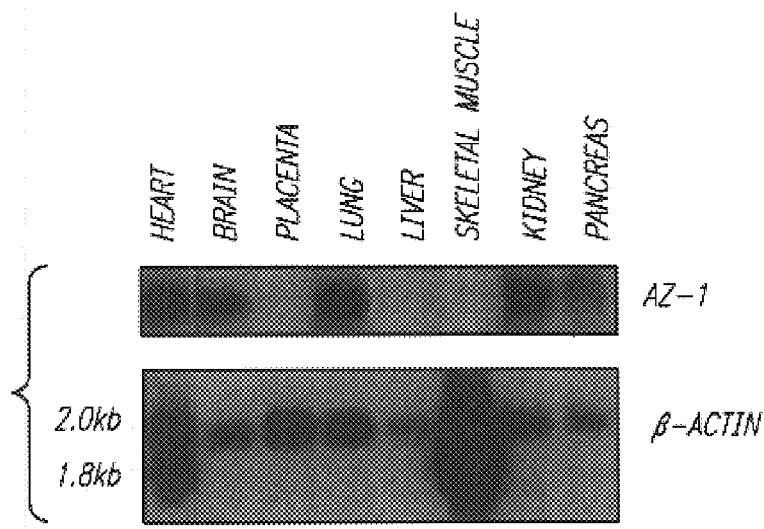
FIG. 11

FIG. 14A
−AZ-1 ab
+AZ-1 ab
FIG. 14B
+AZ-1 ab
FIG. 15
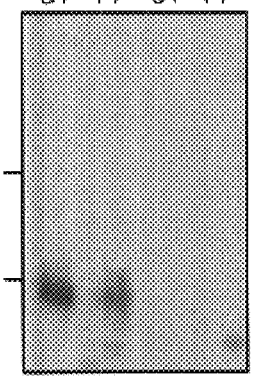 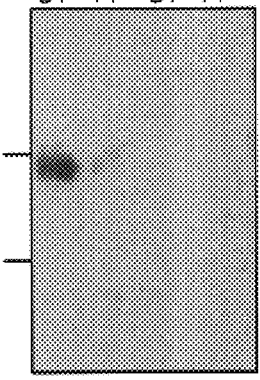 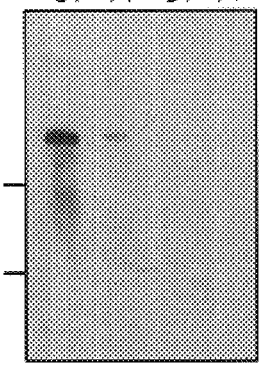
WESTERN ab: AZ-1     β CATENIN     E-CADHERIN
E-CADHERIN   

S1     T4-2 (MOCK)     T4-2 + AZ1

T4-2 (MOCK)     T4-2 + AZ1

FIG. 19A

```
1501 GCTCTCCGTAAGGCTGGAGTTTGACTATTCTGAGGACAAGAGTAGTTGGG 1550
             ||||||||||||||||||||||||||||||||||||||
   1 ..............TGGAGTTTGACTATTCTGAGGACAAGAGTAGTTGGG 36

1551 ACAACCAGCAGGAAAACCCCCTCCTACCAAAAAGATAGGCAAAAAGCCA 1600
     ||||||||||||||||||||||||||||||||||||||||||||||||||
  37 ACAACCAGCAGGAAAACCCCCTCCTACCAAAAAGATAGGCAAAAAGCCA 86

1601 GTTGCCAAAATGCCCCTGAGGAGGCCAAAGATGAAAAAGACACCCGAGAA 1650
     ||||||||||||||||||||||||||||||||||||||||||||||||||
  87 GTTGCCAAAATGCCCCTGAGGAGGCCAAAGATGAAAAAGACACCCGAGAA 136

1651 ACTTGACAACACTCCTGCCTCACCTCCCAGATCCCCTGCTGAACCCAATG 1700
     ||||||||||||||||||||||||||||||||||||||||||||||||||
 137 ACTTGACAACACTCCTGCCTCACCTCCCAGATCCCCTGCTGAACCCAATG 186

1701 ACATCCCCATTGCTAAAGGTACTTACACCTTTGATATTGACAAGTGGGAT 1750
     ||||||||||||||||||||||||||||||||||||||||||||||||||
 187 ACATCCCCATTGCTAAAGGTACTTACACCTTTGATATTGACAAGTGGGAT 236

1751 GACCCCAATTTTAACCCTTTTTCTTCCACCTCAAAAATGCAGGAGTCTCC 1800
     ||||||||||||||||||||||||||||||||||||||||||||||||||
 237 GACCCCAATTTTAACCCTTTTTCTTCCACCTCAAAAATGCAGGAGTCTCC 286

1801 CAAACTGCCCCAACAATCATACAACTTTGACCCAGACACCTGTGATGAGT 1850
     ||||||||||||||||||||||||||||||||||||||||||||||||||
 287 CAAACTGCCCCAACAATCATACAACTTTGACCCAGACACCTGTGATGAGT 336

1851 CCGTTGACCCCTTTAAGACATCCTCTAAGACCCCCAGCTCACCTTCTAAA 1900
     ||||||||||||||||||||||||||||||||||||||||||||||||||
 337 CCGTTGACCCCTTTAAGACATCCTCTAAGACCCCCAGCTCACCTTCTAAA 386

1901 TCCCCAGCCTCCTTTGAGATCCCGGCCAGTGCTATGGAAGCCAATGGAGT 1950
     |||||||||||||||||||||| |||||||||||||||||||||||||||
 387 TCCCCAGCCTCCTTTGAGATCCCAGCCAGTGCTATGGAAGCCAATGGAGT 436

1951 GGACGGGGATGGGCTAAACAAGCCCGCCAAGAAGAAGAAGACGCCCTAA 2000
     ||||||||||||||||||||||||||||||||||||||||||||||||||
 437 GGACGGGGATGGGCTAAACAAGCCCGCCAAGAAGAAGAAGACGCCCTAA 486

2001 AGAC...........GGTGAAAAAGTCGCCAAAACGGTCTCCTCTCTCT 2038
     ||||           |||||||||||||||||||||||||||||||||||
 487 AGACTGACACATTTAGGGTGAAAAAGTCGCCAAAACGGTCTCCTCTCTCT 536

2039 GATCCACCTTCCCAGGACCCCACCCCAGCTGCTACACCAGAAACACCACC 2088
     ||||||||||||||||||||||||||||||||||||||||||||||||||
```

FIG. 19B

```
 537 GATCCACCTTCCCAGGACCCCACCCCAGCTGCTACACCAGAAACACCACC  586

2089 AGTGATCTCTGCGGTGGTCCACGCCACAGATGAGGAAAAGCTGGCGGTCA 2138
     ||||||||||||||||||||||||||||||||||||||||||||||||||
 587 AGTGATCTCTGCGGTGGTCCACGCCACAGATGAGGAAAAGCTGGCGGTCA  636

2139 CCAACCAGAAGTGGACGTGCATGACAGTGGACCTAGAGGCTGACAAACAG 2188
     ||||||||||||||||||||||||||||||||||||||||||||||||||
 637 CCAACCAGAAGTGGACGTGCATGACAGTGGACCTAGAGGCTGACAAACAG  686

2189 GACTACCCGCAGCCCTCGGACCTGTCCACCTTTGTAAACGAGACCAAATT 2238
     ||||||||||||||||||||||||||||||||||||||||||||||||||
 687 GACTACCCGCAGCCCTCGGACCTGTCCACCTTTGTAAACGAGACCAAATT  736

2239 CAGTTCACCCACTGAGGAGTTGGATTACAGAAACTCCTATGAAATTGAAT 2288
     ||||||||||||||||||||||||||||||||||||||||||||||||||
 737 CAGTTCACCCACTGAGGAGTTGGATTACAGAAACTCCTATGAAATTGAAT  786

2289 ATATGGAGAAAATTGGCTCCTCCTTACCTCAGGACGACGATGCCCCGAAG 2338
     ||||||||||||||||||||||||||||||||||||||||||||||||||
 787 ATATGGAGAAAATTGGCTCCTCCTTACCTCAGGACGACGATGCCCCGAAG  836

2339 AAGCAGGCCTTGTACCTTATGTTTGACACTTCTCAGGAGAGCCCTGTCAA 2388
     ||||||||||||||||||||||||||||||||||||||||||||||||||
 837 AAGCAGGCCTTGTACCTTATGTTTGACACTTCTCAGGAGAGCCCTGTCAA  886

2389 GTCATCTCCCGTCCGCATGTCAGAGTCCCCGACGCCGTGTTCAGGGTCAA 2438
     ||||||||||||||||||||||||||||||||||||||||||||||||||
 887 GTCATCTCCCGTCCGCATGTCAGAGTCCCCGACGCCGTGTTCAGGGTCAA  936

2439 GTTTTGAAGAGACTGAAGCCCTTGTGAACACTGCTGCGAAAAACCAGCAT 2488
     ||||||||||||||||||||||||||||||||||||||||||||||||||
 937 GTTTTGAAGAGACTGAAGCCCTTGTGAACACTGCTGCGAAAAACCAGCAT  986

2489 CCTGTCCCACGAGGACTGGCCCCTAACCAAGAGTCACACTTGCAGGTGCC 2538
     ||||||||||||||||||||||||||||||||||||||||||||||||||
 987 CCTGTCCCACGAGGACTGGCCCCTAACCAAGAGTCACACTTGCAGGTGCC 1036

2539 AGAGAAATCCTCCCAGAAGGAGCTGGAGGCCATGGGCTTGGGCACCCCTT 2588
     |||||||||||||||||||||||||||||||||||| |||||||||||||
1037 AGAGAAATCCTCCCAGAAGGAGCTGGAGGCCATGGGTTTGGGCACCCCTT 1086

2589 CAGAAGCGATTGAAATT................................ 2605
     |||||||||||||||||
1087 CAGAAGCGATTGAAATTACAGCTCCCGAGGGCTCCTTTGCCTCTGCTGAC 1136
```

FIG. 19C

```
2606 ........AGAGAGGCTGCTCACCCAACAGACGTCTCCATCTCCAAAACA 2647
             ||||||||| ||||||||||||||||||||||||||||||
1237 AACTCCAGAGAGAGGCTGTTCACCCAACAGACGTCTCCATCTCCAAAACA 1286

2648 GCCTTGTACTCCCGCATCGGGACCGCTGAGGTGGAGAAACCTGCAGGCCT 2697
     ||||||||||||||||||||||||||||||||||||||||||||||||||
1287 GCCTTGTACTCCCGCATCGGGACCGCTGAGGTGGAGAAACCTGCAGGCCT 1336

2698 TCTGTTCCAGCAGCCCGACCTGGACTCTGCCCTCCAGATCGCCAGAGCAG 2747
     ||||||||||||||||||||||||||||||||||||||||||||||||||
1337 TCTGTTCCAGCAGCCCGACCTGGACTCTGCCCTCCAGATCGCCAGAGCAG 1386

2748 AGATCATAACCAAGGAGAGAGAGGTCTCAGAATGGAAAGATAAATATGAA 2797
     ||||||||||||||||||||||||||||||||||||||||||||||||||
1387 AGATCATAACCAAGGAGAGAGAGGTCTCAGAATGGAAAGATAAATATGAA 1436

2798 GAAAGCAGGCGGGAAGTGATGGAAATGAGGAAAATAGTGGCCGAGTATGA 2847
     ||||||||||||||||||||||||||||||||||||||||||||||||||
1437 GAAAGCAGGCGGGAAGTGATGGAAATGAGGAAAATAGTGGCCGAGTATGA 1486

2848 GAAGACCATCGCTCAGATGATAGAGGACGAACAGAGAGAGAAGTCAGTCT 2897
     ||||||||||||||||||||||||||||||||||||||||||||||||||
1487 GAAGACCATCGCTCAGATGATAGAGGACGAACAGAGAGAGAAGTCAGTCT 1536

2898 CCCACCAGACGGTGCAGCAGCTGGTTCTGGAGAAGGAGCAAGCCCTGGCC 2947
     ||||||||||||||||||||||||||||||||||||||||||||||||||
1537 CCCACCAGACGGTGCAGCAGCTGGTTCTGGAGAAGGAGCAAGCCCTGGCC 1586

2948 GACCTGAACTCCGTGGAGAAGTCTCTGGCCGACCTCTTCAGAAGATATGA 2997
     ||||||||||||||||||||||||||||||||||||||||||||||||||
1587 GACCTGAACTCCGTGGAGAAGTCTCTGGCCGACCTCTTCAGAAGATATGA 1636

2998 GAAGATGAAGGAGGTCCTAGAAGGCTTCCGCAAGAATGAAGAGGTGTTGA 3047
     ||||||||||||||||||||||||||||||||||||||||||||||||||
1637 GAAGATGAAGGAGGTCCTAGAAGGCTTCCGCAAGAATGAAGAGGTGTTGA 1686

3048 AGAGATGTGCGCAGGAGTACCTGTCCCGGGTGAAGAAGGAGGAGCAGAGG 3097
     ||||||||||||||||||||||||||||||||||||||||||||||||||
1687 AGAGATGTGCGCAGGAGTACCTGTCCCGGGTGAAGAAGGAGGAGCAGAGG 1736

3098 TACCAGGCCCTGAAGGTGCACGCGGAGGAGAAACTGGACAGGGCCAATGC 3147
     ||||||||||||||||||||||||||||||||||||||||||||||||||
1737 TACCAGGCCCTGAAGGTGCACGCGGAGGAGAAACTGGACAGGGCCAATGC 1786
```

FIG. 19D

```
3148 TGAGATTGCTCAGGTTCGAGGCAAGGCCCAGCAGGAGCAAGCCGCCCACC 3197
     ||||||||||||||||||||||||||||||||||||||||||||||||||
1787 TGAGATTGCTCAGGTTCGAGGCAAGGCCCAGCAGGAGCAAGCCGCCCACC 1836

3198 AGGCCAGCCTGCGGAAGGAGCAGCTGCGAGTGGACGCCCTGGAAAGGACG 3247
     ||||||||||||||||||||||||||||||||||||||||||||||||||
1837 AGGCCAGCCTGCGGAAGGAGCAGCTGCGAGTGGACGCCCTGGAAAGGACG 1886

3248 CTGGAGCAGAAGAATAAAGAAATAGAAGAACTCACCAAGATTTGTGACGA 3297
     ||||||||||||||||||||||||||||||||||||||||||||||||||
1887 CTGGAGCAGAAGAATAAAGAAATAGAAGAACTCACCAAGATTTGTGACGA 1936

3298 ACTGATTGCCAAAATGGGGAAAAGCTAACTCTGAACCGAATGTTTTGGAC 3347
     ||||||||||||||||||||||||||||||||||||||||||||||||||
1937 ACTGATTGCCAAAATGGGGAAAAGCTAACTCTGAACCGAATGTTTTGGAC 1986

3348 TTAACTGTTGCGTGCAATATGACCGTCGGCACACTGCTGTTCCTCCAGTT 3397
     ||||||||||| ||||||||||||||||||||||||||||||||||||||
1987 TTAACTGTTGCG.GCAATATGACCGTCGGCACACTGCTGTTCCTCCAGTT 2035

3398 CCATGGACAGGTTCTGTTTTCACTTTTTCGTATGCACTACTGTATTTCCT 3447
     ||||||||||||||||||||||||||||||||||||||||||||||||||
2036 CCATGGACAGGTTCTGTTTTCACTTTTTCGTATGCACTACTGTATTTCCT 2085

3448 TTCTAAATAAAATTGATTTGATTGTATGCAGTACTAAGGAGACTATCAGA 3497
     ||||||||||||||||||||||||||||||||||||||||||||||||||
2086 TTCTAAATAAAATTGATTTGATTGTATGCAGTACTAAGGAGACTATCAGA 2135

3498 ATTTCTTGCTATTGGTTTGCATTTTCCTAGTATAATTCATAGCAAGTTGA 3547
     ||||||||||||||||||||||||||||||||||||||||||||||||||
2136 ATTTCTTGCTATTGGTTTGCATTTTCCTAGTATAATTCATAGCAAGTTGA 2185

3548 CCTCAGAGTTCCTGTATCAGGGAGATTGTCTGATTCTCTAATAAAAGACA 3597
     ||||||||||||||||||||||||||||||||||||||||||||||||||
2186 CCTCAGAGTTCCTGTATCAGGGAGATTGTCTGATTCTCTAATAAAAGACA 2235

3598 CATTGCTGACCTTGGCCTTGCCCTTTGTACACAAGTTCCCAGGGTGAGCA 3647
     ||||||||||||||||||||||||||||||||||||||||||||||||||
2236 CATTGCTGACCTTGGCCTTGCCCTTTGTACACAAGTTCCCAGGGTGAGCA 2285

3648 GCTTTTGGATTTAATATGAACATGTACAGCGTGCATAGGGACTCTTGCCT 3697
     ||||||||||||||||||||||||||||||||||||||||||||||||||
2286 GCTTTTGGATTTAATATGAACATGTACAGCGTGCATAGGGACTCTTGCCT 2335

3698 TAAGGAGTGTAAACTTGATCTGCATTTGCTGATTTGTTTTTAAAAAAACA 3747
     ||||||||||||||||||||||||||||||||||||||||||||||||||
```

FIG. 19E

```
2336 TAAGGAGTGTAAACTTGATCTGCATTTGCTGATTTGTTTTTAAAAAACA 2385

3748 AGAAATGCATGTTTCAAATAAAATTCTCTATTGTAAATAAAATTTTTTCT 3797
     ||||||||||||||||||||||||||||||||||||||||||||||||||
2386 AGAAATGCATGTTTCAAATAAAATTCTCTATTGTAAATAAAATTTTTTCT 2435

3798 TTGGATCTTGGCAATA 3813
     ||||||||||
2436 TTGGATCTTGA..... 2446
```

FIG. 20A

```
  1 ........................MPLRRPKMKKTPEKLDNTP  19
                            ||||||||||||||||||
  1 EFDYSEDKSSWDNQQENPPPTKKIGKKPVAKMPLRRPKMKKTPEKLDNTP  50

20 ASPPRSPAEPNDIPIAKGTYTFDIDKWDDPNFNPFSSTSKMQESPKLPQQ  69
    |||||||||||||||||||||||||||||||||||||||||||||||||
 51 ASPPRSPAEPNDIPIAKGTYTFDIDKWDDPNFNPFSSTSKMQESPKLPQQ 100

70 SYNFDPDTCDESVDPFKTSSKTPSSPSKSPASFEIPASAMEANGVDGDGL 119
    |||||||||||||||||||||||||||||||||||||||||||||||||
101 SYNFDPDTCDESVDPFKTSSKTPSSPSKSPASFEIPASAMEANGVDGDGL 150

120 NKPAKKKKTPLKT....VKKSPKRSPLSDPPSQDPTPAATPETPPVISAV 165
    |||||||||||||    ||||||||||||||||||||||||||||||||
151 NKPAKKKKTPLKTDTFRVKKSPKRSPLSDPPSQDPTPAATPETPPVISAV 200

166 VHATDEEKLAVTNQKWTCMTVDLEADKQDYPQPSDLSTFVNETKFSSPTE 215
    |||||||||||||||||||||||||||||||||||||||||||||||||
201 VHATDEEKLAVTNQKWTCMTVDLEADKQDYPQPSDLSTFVNETKFSSPTE 250

216 ELDYRNSYEIEYMEKIGSSLPQDDDAPKKQALYLMFDTSQESPVKSSPVR 265
    |||||||||||||||||||||||||||||||||||||||||||||||||
251 ELDYRNSYEIEYMEKIGSSLPQDDDAPKKQALYLMFDTSQESPVKSSPVR 300

266 MSESPTPCSGSSFEETEALVNTAAKNQHPVPRGLAPNQESHLQVPEKSSQ 315
    |||||||||||||||||||||||||||||||||||||||||||||||||
301 MSESPTPCSGSSFEETEALVNTAAKNQHPVPRGLAPNQESHLQVPEKSSQ 350

316 KELEAMGLGTPSEAIEI................................ 332
    |||||||||||||||||
351 KELEAMGLGTPSEAIEITAPEGSFASADALLSRLAHPVSLCGALDYLEPD 400

333 ..............REAAHPTDVSISKTALYSRIGTAEVEKPAGLLFQQP 368
                  ||| ||||||||||||||||||||||||||||||||
401 LAEKNPPLFAQKLQREAVHPTDVSISKTALYSRIGTAEVEKPAGLLFQQP 450

369 DLDSALQIARAEIITKEREVSEWKDKYEESRREVMEMRKIVAEYEKTIAQ 418
    |||||||||||||||||||||||||||||||||||||||||||||||||
451 DLDSALQIARAEIITKEREVSEWKDKYEESRREVMEMRKIVAEYEKTIAQ 500

419 MIEDEQREKSVSHQTVQQLVLEKEQALADLNSVEKSLADLFRRYEKMKEV 468
    |||||||||||||||||||||||||||||||||||||||||||||||||
501 MIEDEQREKSVSHQTVQQLVLEKEQALADLNSVEKSLADLFRRYEKMKEV 550

469 LEGFRKNEEVLKRCAQEYLSRVKKEEQRYQALKVHAEEKLDRANAEIAQV 518
    |||||||||||||||||||||||||||||||||||||||||||||||||
```

FIG. 20B

```
551 LEGFRKNEEVLKRCAQEYLSRVKKEEQRYQALKVHAEEKLDRANAEIAQV 600
         .         .         .         .         .
519 RGKAQQEQAAHQASLRKEQLRVDALERTLEQKNKEIEELTKICDELIAKM 568
    |||||||||||||||||||||||||||||||||||||||||||||||||
601 RGKAQQEQAAHQASLRKEQLRVDALERTLEQKNKEIEELTKICDELIAKM 650

569 GKS 571
    |||
651 GKS 653
```

HUMAN AZU-1 GENE, VARIANTS THEREOF AND EXPRESSED GENE PRODUCTS

This application is based on the provisional application, Serial No. 60/090,747, filed Jun. 26, 1998.

The United States Government has certain rights in this invention pursuant to Contract DE-AC03-76SF00098 between the United States Department of Energy and the University of California.

BACKGROUND OF THE INVENTION

Field of the Invention

This invention concerns a novel human AZU-1 gene, mutants, variants and fragments thereof, and protein products encoded by the AZU-1 gene and homologs encoded by the variants of AZU-1 gene acting as tumor suppressors or markers of malignancy progression and tumorigenicity reversion. In particular, this invention concerns identifying, isolation and characterization of novel AZU-1 and AZU-2 genes localized to a tumor suppressive locus at chromosome 10q26, highly expressed in nonmalignant and premalignant cells derived from a human breast tumor progression model. Additionally, the invention concerns findings that AZU-1 and AZU-2 genes exhibit tissue-specific expression profiles and that AZU-1 gene expression in tumor cells is low or absent. The invention further concerns recombinant full length protein sequences encoded by the AZU-1 gene and nucleotide sequences of AZU-1 and AZU-2 genes. The invention also concerns monoclonal or polyclonal antibodies specific to AZU-1, AZU-2 encoded protein and to AZU-1, or AZU-2 encoded protein homologs.

BACKGROUND AND RELATED DISCLOSURE

The evolvement of breast cancer is a multistep and cumulative process and understanding of the genetic and phenotypic alterations in successive steps is essential for designing therapeutic interventions and diagnostic assays.

In the human body, the epithelial component of the breast is embedded in the stroma and forms a branching ductal structure that emanates from the nipple, repeatedly bifurcates, and terminates in lobules, alveoli, and end buds. Although stroma accounts for >80% of the breast volume, approximately 95% of the cancers produced in the breast are of epithelial origin. To elucidate the advancement of human breast cancer, a functionally relevant cell culture model is required. The differences in breast tissue compartmentalization, phenotypic characteristics, and the mutagenic frequency between human and rodents underline the need to develop a human breast cell model.

An unconventional spontaneously-transformed HMT-3522 cell lines was described recently in *Cancer Research*, 56:2039 (1996) where the immortalized human mammary epithelial cells (S1) established from fibrocystic breast tissue was propagated in chemically defined medium described in *In Vitro Call. Dev. Biol.*, 23:181 (1987). S1 cells were near-diploid and expressed luminal epithelial cell differentiation markers cytokeratin-18 and sialomucin. Genetic changes such as p53 point mutation (*Exp. Cell. Res.*, 215:380 (1994)) and c-myc amplification (*Cancer Research*, 52:1210 (1992)) have already been noted in later passages, i.e., >50 of the nonmalignant S1 cells. In passage 118, cells were adapted to grow in epidermal growth factor (EGF)-free medium and a new EGF-independent subline (S2, premalignant) was isolated (ibid).

Alterations in gene expression of EGF receptor, transforming growth factor (TGF)-α and c-erb-B2 were seen in S2 cells. The established S2 cell line underwent cytogenetic evolution and exhibited genomic instability and heterogeneity (*Cancer Genetics and Cytogenetics*, 78:189 (1994)). Nevertheless, S2 cells remained nontumorigenic until passage 238. At that time, it was able to induce tumor growth in nude mice. Following second round of mouse transplantation, another subline (T4-2, tumorigenic) existed as a relatively homogenous malignantly-transformed cell population. One extra copy of chromosome 7p which harbors EGF receptor gene was found in the T4-2 cells (*Cancer Res.*, 56:2039 (1996)).

Detection and suppression of cancerous tissue growth is of extreme interest and importance. It is, therefore, a primary objective of this invention to provide means for identification, detection and suppression of cancerous growth in breast tissue.

All patents, patent applications and publications cited herein are hereby incorporated by reference.

SUMMARY

One aspect of the current invention is a human AZU-1 gene or a variant, mutant, or fragment thereof.

Another aspect of the current invention is a nucleotide sequence of AZU-1 and AZU-2 genes, identified as SEQ ID NO: 1 and SEQ ID NO: 2.

Another aspect of the current invention is a DNA sequence identified as SEQ ID NO: 1 encoding a protein comprising the amino acid sequence identified as SEQ ID NO: 3.

Still another aspect of the current invention is a protein of the amino acid sequence identified as SEQ ID NO: 3.

Still yet another aspect of the current invention is a protein encoded by AZU-1 gene, or by a variant, mutant or fragment thereof, or any protein containing said protein encoded by AZU-1 gene, variant, mutant, or fragment thereof, or any protein which shares homology with AZU-1 encoded protein or AZU-2 encoded protein, variant, mutant or fragment thereof.

Still another aspect of the current invention is a protein encoded by the AZU-1 gene, variant, mutant, analog or fragment thereof acting as a tumor suppressor or a marker of malignancy progression and tumorigenic reversion.

Still yet another aspect of the current invention is a method for diagnosis and detection of progression of human breast cancer by detecting presence and quantity of a protein identified as SEQ ID NO: 3 or a homolog thereof in human breast cells or tissue or by detecting expression of AZU-1 gene, mutant, variant, fragment thereof by in situ hybridization or RT-PCR.

Still yet another aspect of the current invention is a diagnostic method for detection of the presence of AZU-1 protein in human breast cancer by treating a biopsy sample of a subject patient with a polyclonal or monoclonal AZU-1 antibodies or detection of the level of AZU-1 message.

Yet another aspect of the current invention is a method for prevention or treatment of human breast cancer by providing a subject in need thereof a therapeutically effective amount of a protein identified as SEQ ID NO: 3 or homolog thereof, able to act as a tumor suppressor of human breast cancer cells.

Still yet another aspect of the current invention is a tissue targeted gene therapy for treatment of human breast tumor.

Still another aspect of the current invention is an ELISA kit for detection of expression of AZU-1 gene or a variant thereof by detecting presence or absence of AZU-1 encoded protein with AZU-1 monoclonal or polyclonal antibodies.

Still another aspect of the current invention is a message detection kit for detection of expression of AZU-1 gene or a variant thereof by bDNA technology (Quantigene Gene Expression Assay, Chiron Corp., Emeryville, Calif., in situ hybridization or RT-PCR by detecting presence or absence of AZU-1 message.

BRIEF DESCRIPTION OF THE FIGURES

The patent or application file contains at least one drawing executed in color. Copies of this patent or patent application publication with color drawing(s) will be provided by the office upon request and payment of necessary fee.

FIG. 3 shows characterization of HMT-3522 progression series.

FIGS. 4A–4B is the cDNA sequence (SEQ ID NO: 1) of AZU-1 gene showing a divergent site between nucleotides 429–430.

FIGS. 5A–5B is the cDNA sequence (SEQ ID NO: 2) of AZU-2 gene showing a divergent site between nucleotide 764–765.

FIG. 6 is an amino acid sequence (SEQ ID NO: 3) of the protein encoded by AZU-1 gene. FIG. 6A shows SPAZI (SEQ ID NO: 7), REGION I (SEQ ID NO: 13), REGION II (SEQUENCE ID NO: 14) and Coiled-Coil (CCD) (SEQ ID NO: 8) domains. FIG. 6B is a schematic diagram of all AZU-1 and TACC1 domains. FIG. 6C shows SPAZI domain homology for AZU-1 (SEQ ID NO: 3), TACC1 (A) (SEQ ID NO: 9), TACC2 (B) (SEQ ID NO: 15), TACC3 (SEQ ID NO: 16), and BCK1 (SEQ ID NO: 10) protein. FIG. 6D shows homology regions for coiled-coil domain (CCD) in AZU-1 (SEQ ID NO: 8), TACC1 (SEQ ID NO: 11), TACC3 (SEQ ID NO: 17) and SB1.8 (SEQ ID NO: 12) genes.

FIG. 9 illustrates differential expression of AZU-1 gene in premalignant and breast tumor cell lines. FIG. 9A shows differential display analysis in premalignant S2 and T4 tumor cells. FIG. 9B shows Northern blot analysis in premalignant S2 and T4 tumor cells.

FIG. 10 shows downregulation of AZU-1 in breast tumor cell lines and biopsies. FIG. 10A shows expression of AZU-1 in S1 and MCF10A nonmalignant cell lines and in luminal epithelial and myoepithelial nonmalignant primary cells. FIG. 10B shows downregulation of AZU-1 gene in premalignant S2 and malignant T4, HMT 3909, MCF-7, CAMA-1, NDA-MB 468, SKBR-3, T47D, MDA-MB 231, Hs578T and BT 549 cells. FIG. 10C shows downregulation of AZU-1 gene in in situ carcinoma.

FIG. 11 shows tissue specific expression of AZU-1 in various normal human tissues.

FIG. 13 is a color image which shows the association of AZU-1 with cytoskeletal complexes in nonmalignant breast cells.

FIG. 14 is a color image of in situ staining of AZU-1 in normal breast acinus (FIG. 14A) and breast duct (FIG. 14B).

FIG. 15 illustrates the presence of E-cadherin and β-catenin in AZU-1 immunocomplexes.

FIG. 16 shows that ectopically-expressed AZU-1 gene reduces tumorigenicity and invasiveness.

FIG. 1B shows basement membrane staining of T4-2 (mock) and T4-2+AZU-1 cells.

FIGS. 19A–19B shows a sequence alignment of AZU-1 and its variant TACC2 cDNAs. Sequence insertions are indicated by dots.

FIGS. 20A–20B shows an amino acid sequence alignment of AZU-1 and its variant TACC2 proteins. Sequence insertions are indicated by dots.

DEFINITIONS

Figure 1:
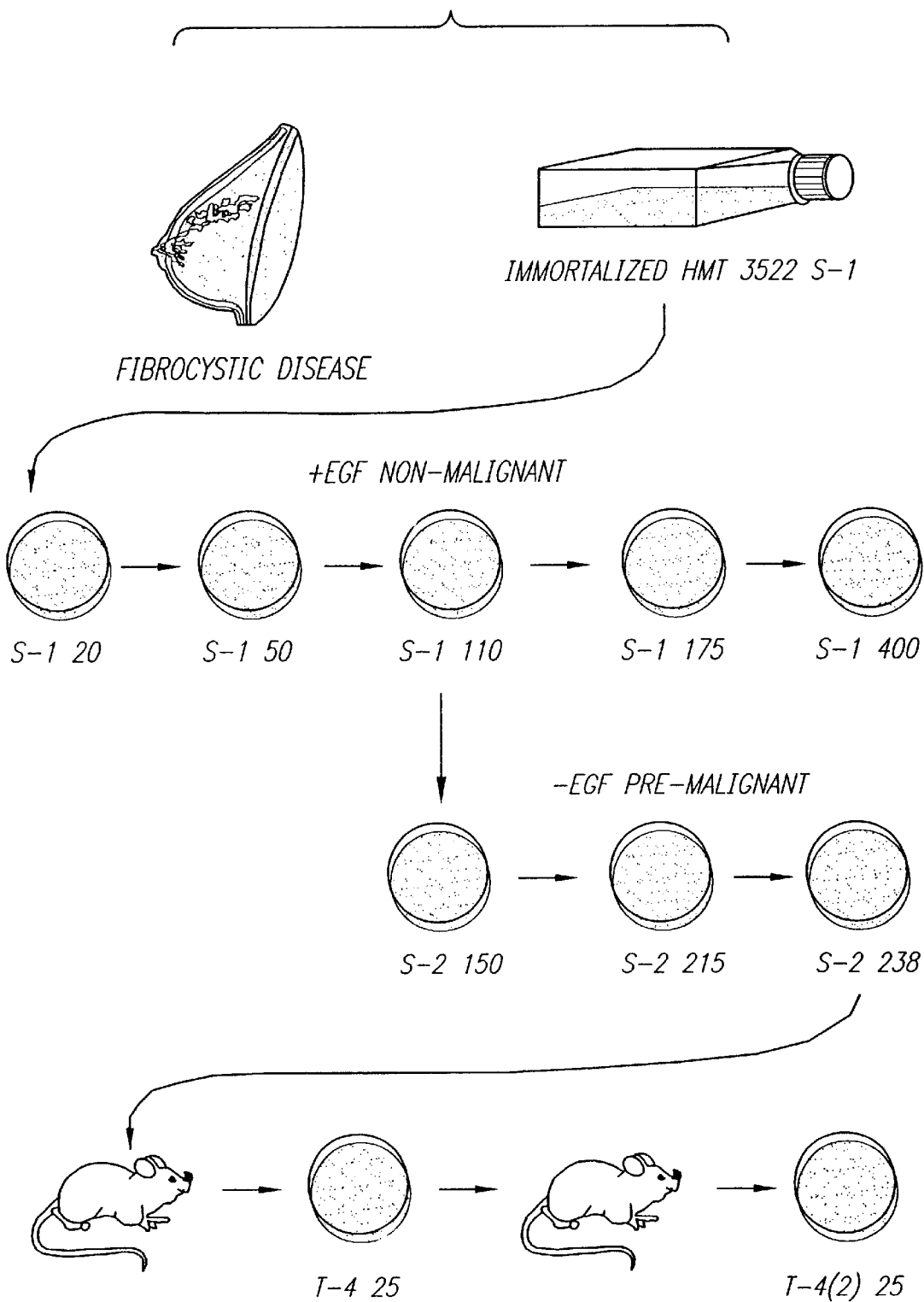
FIG. 1 is a schematic diagram of malignant transformation of HMT3522 human breast epithelial cells.

As used herein,

"CCD" means coiled-coil domain.

"ER" means estrogen receptor.

"RACE" means rapid amplification of cDNA ends.

"AZU-1" or "AZU-1 gene" means antizuai-1 gene. AZU-1 refers to the entire AZU-1 genomic sequence, including enhancers, promoter sequences, introns and exons.

"AZU-1 mutant", "AZU-1 variant" or "AZU-1 fragment" mean all AZU-1 gene products, such as all potential splice variants derived from the gene and their protein products. Their associated 5' and 3' untranslated regions are also included. Also included are all mutant forms of AZU-1, whether spontaneously arising or specifically engineered. All known AZU-1-related genes, such as TACC-1, TACC-2 and TACC-3 are also included under this definition as long as they share about 25% of homology.

"AZU-1 gene encoded protein" means and includes all protein coding sequences encoded by AZU-1 gene, variant or mutant thereof, as well as 5' and 3' untranslated sequences identified here and in other AZU-1 splice variants.

"HMT-3522" means human mammary tumor cell line 3522.

"Ki-67" means a marker for proliferating cells.

"Cadherin" means cell-adherens junction protein.

"E-cadherin" means epithelial cadherin.

"β-catenin" means an adherens junction protein.

"GAPDH" means a metabolic protein GAPDH (glyceraldehyde phosphate dehydrogenase) expressed by a common gene in metabolic pathway. In this application, the message level of GADPH is used as control for RNA loading in Northern blot.

"S1" or "S-1" means a nonmalignant breast cell line.

"S2" or "S-2" means a premalignant breast cell line.

"MCF10A" means a nonmalignant breast cell line.

"Luminal epithelial cells" means normal cells present in the breast tissue.

"Myoepithelial cells" means normal cells present in the breast tissue.

"T4", "MCF-7", "CAMA-1", "BT-20", "MDA-MB 468", "SKBR-3", "T47D", "MDA-MB 231", "Hs578T", and "BT 549" means breast tumor cell lines specifically so identified.

"HMT 3909" means a breast tumor cell line contaminated with normal myoepithelial cells.

"T4-2 (mock)" means breast tumor cells transfected with empty expression vector.

"Ectopically expressed AZU-1" means artificially expressed or overexpressed AZU-1 gene.

"Upregulation of AZU-1 gene" means observed increased expression of AZU-1 gene.

"Variant" means any variant derived from splicing, exon shuffling, deletion or insertion causing frame shifting. Variant is exemplarized by AZU-2 gene and TACC2 gene where TACC2 gene is a variant of AZU-1 gene.

"Mutant" means AZU-1 gene containing a point mutation, deletion, insertion, or truncation.

"Fragment" means a functional domain, such as SPAZI or coiled-coil domain involved in protein-protein interaction.

"Homolog" means any homologous protein sharing a substantial sequence similarity (about 25% or more) with AZU-1 expressed protein. Exemplary proteins are proteins expressed by TACC1 or TACC3 or a variant thereof expressed by TACC2.

"TACC1" means embryonically expressed TACC1 gene from the 8p11 breast cancer amplicon.

"TACC2" means expressed TACC2 gene from the 10q25-q26 locus.

"TACC3" means expressed TACC3 gene from the 4p16.3 locus.

"SPAZI" means serine-proline rich AZU-1 domain.

"Coiled-coil" means heptad repeats participating in protein-protein interactions.

"BCK1" means a *Saccharomyces cerevisiae* yeast gene.

"BLAST" means basic local alignment sequence tool. BLAST is a service available from the National Center for Biotechnology Information which compares and matches a nucleotide or protein sequence against databases at the NCBI.

DETAILED DESCRIPTION OF THE INVENTION

This invention relates to a cancer-related gene AZU-1. AZU-1 gene is novel and has never before been described or disclosed. AZU-1 gene and its encoded protein have been found to be present in normal breast cells. The expression of AZU-1 gene in tumor cells, however, has been found to be significantly decreased in ten human breast cancer cell lines and carcinoma cells in situ. The level of the AZU-1 encoded protein is significantly decreased in these cell lines.

A protein encoded by AZU-1 gene is believed to act as a protective agent against cancer by suppressing a tumor growth and the detection of its level in breast cells is useful as a marker of malignancy progression and tumorigenic reversion. The invention is useful for diagnosis, prognosis and treatment of breast cancer.

The invention also relates to identification, isolation and sequencing of the human AZU-1 gene and its variant AZU-2 gene encoding proteins acting as tumor suppressors and markers for tumor progression and tumorigenicity reversion.

AZU-1 gene was isolated and sequenced (SEQ ID NO: 1) and the amino acid sequence of AZU-1 encoded protein was deduced (SEQ ID NO: 3). The protein was additionally identified by specific AZU-1 antibodies. Functional significance of the loss of AZU-1 expression in tumor cells has been investigated in vitro and in vivo and linked to tumorigenic and invasion suppressive roles.

Additionally, the invention relates to a method for treatment, detection and prognosis of breast cancer by providing a patient in need of such treatment a therapeutically effective amount of a recombinant protein, by detecting the level of native protein encoded by AZU-1 gene in the breast tissue biopsy sample or by determining a degree of expression of AZU-1 gene and/or levels of expressed AZU-1 protein.

I. Tumorigenic Cell Line Progression Model

The current invention was developed and tested on various models of normal or breast tumor cell lines which were developed and are described below. Progression model for tumorigenic cell line T4-2 was developed by malignant transformation of human breast epithelial cells.

Presence or absence of AZU-1 gene expression was tested in normal epithelial or myoepithelial cells, nonmalignant S1 cell line, premalignant S2 cell line and in T4-2 breast tumor cell line.

Malignant T4-2 breast tumor cell line was derived from nonmalignant fibrocystic breast cells. Malignant transformation of nonmalignant HMT3522-S1 cell line into malignant T4-2 cells is illustrated in FIG. 1.

The nonmalignant cells were obtained as a cell mixture from a patient suffering from fibrocystic disease. The cells were cultured to specifically promote the growth of epithelial cells. The epithelial cells were then immortalized as a nonmalignant HMT 3522-S1 cell line. The HMT 3522-S1 cells were repeatedly passaged 20 (S-1 20), 50 (S-1 50), 110 (S-1 110), 175 (S-1 175) up to 400 passages (S-1 400) in the presence of EGF (+EGF) and were found to be nonmalignant. When, after 110 passages, epidermal growth factor (EGF) was removed from the culture, at about 150 passages, the EGF deprived cells turned into premalignant S-2 cell line. After the S-2 cell line was further propagated up to S-2 215, the S-2 cells at every 10-passage intervals from 150 passages up were injected into nude mice. None of the S-2 cells up to passage 238 were found to produce tumors. After about 8 weeks, approximately 50% of the S2-238 injected nude mice were found to produce tumors. Their tumor nodules were then removed and the cells were further propagated and these cells were again injected into the nude mice. After 8 weeks, more than 90% of nude mice were found to have tumors. The tumor nodules were removed again and the cells were propagated as T4-2 cells. T4-2 cells were tested for AZU-1 gene expression and/or for the presence or absence of AZU-1 encoded protein in assays described below.

Figure 2:
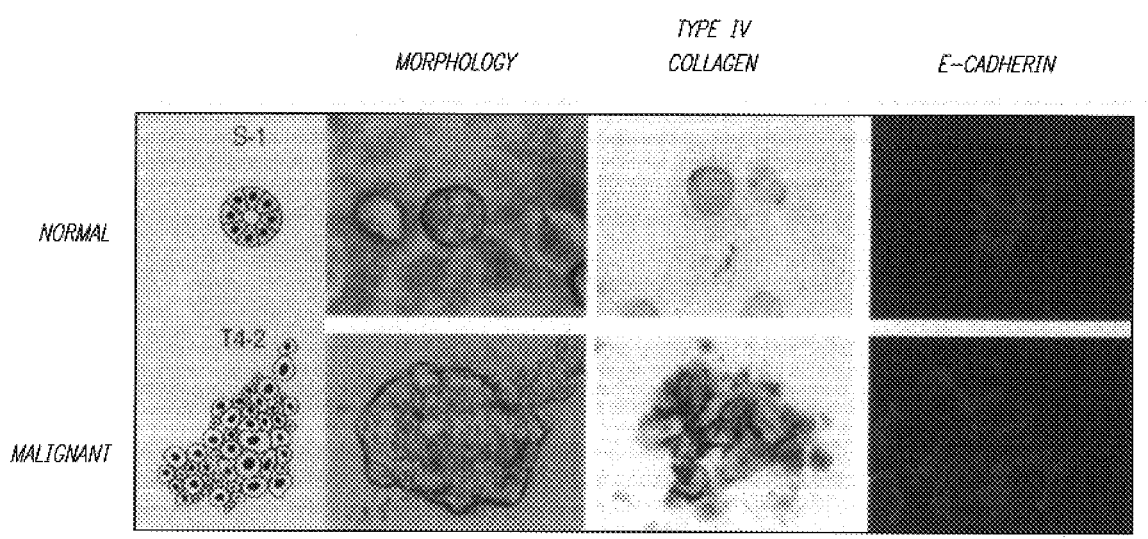
FIG. 2 shows phenotypic recapitulation of tissue morphology in 3-D reconstituted basement membrane (rBM) culture assay for S1 and T4-2 cells.

Normal cells, cell lines and malignant cell lines were then tested in a series of morphological, structural and adhesion studies and differences between normal S-1 and malignant T4-2 cell lines observed in these studies are seen in FIG. 2. FIG. 2 is a comparative phenotypic recapitulation of normal S-1 cell line and malignant T4-2 cell line in 3-D basement membrane culture assay.

As seen in FIG. 2, a schematic diagram of S-1 and T4-2 cell lines (extreme left) shows S-1 cells are organized in a sphere, which corresponds to its morphological organization seen in morphology subset (middle left). In morphology subset, normal S-1 cell are seen to be organized in spherical manner. The malignant T4-2 cells on the other hand, are shown to form disorganized colonies, seen in both schematic and morphology subsets.

The normal S-1 cells were seen having a smooth spherical shape basement membrane when tested in a 3-D laminin-rich reconstituted basement membrane culture assay and immunostained with human type IV collagen (middle right). When the malignant cells were analyzed by human type IV collagen immunostaining, they revealed a disorganized pattern. Staining with E-cadherin (E-cadherin subset, extreme right) shows intact cell-cell adhesion network in S1 cells and disrupted organization in T4-2 cells.

Differences between the normal nonmalignant, premalignant and malignant cells which were obtained in progression series of HMT 3522, seen in FIG. 1, are further illustrated in FIG. 3, which shows characterization of the HMT 3522 progression series. All types of cells, that is the normal S-1 (S1-50, S1-110 and 51-175) cells, premalignant 82 (S2-215) cells and malignant T4-2 (T4-2-25) cells obtained as described in FIG. 1 were analyzed by comparative genomic hybridization, phase contrast microscopy, and immunostaining with F-actin phalloidin staining, and with E-cadherin.

The HMT-3522 human breast tumor progression series is comprised of a continuum of genetically related cell populations that range in phenotypic behavior from non-malignant to tumorigenic. In order to identify genes that play a crucial role in the final stages of breast tumor progression, a differential display strategy was utilized to compare the gene expression patterns of the model's tumorigenic cell population (called T4-2) with that of its pre-malignant progenitor (called S2). One of the genes identified using this approach is abundantly expressed in non-malignant luminal epithelial cells but is expressed at significantly lower levels in a variety of breast tumor cell types. Because of this expression pattern, which is commonly observed with tumor suppressors of the Type II class, this gene is referred to as anti-zuai-1 (or AZU-1, with "zuai" meaning breast cancer in Chinese).

Figures 3A, 3B, 3C, 3D, 3E:
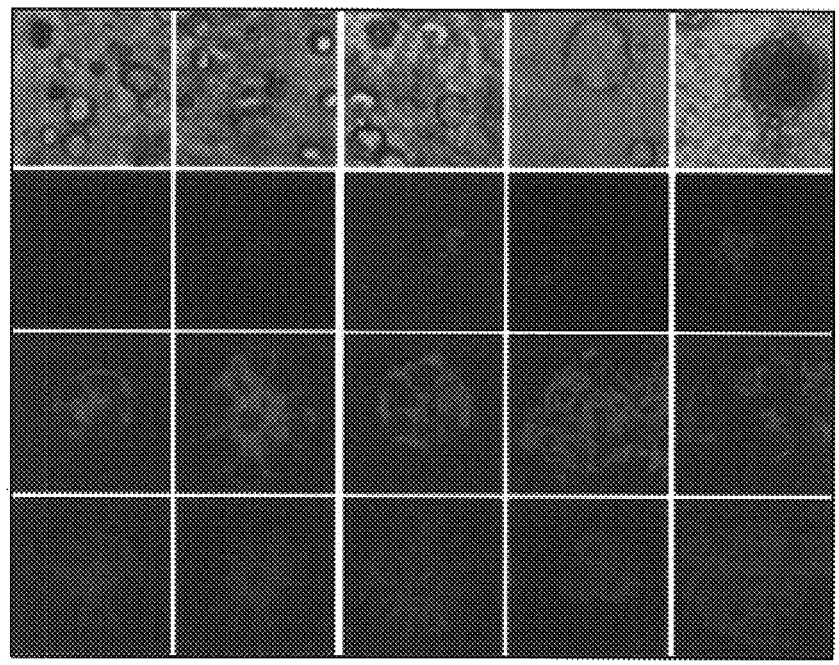
FIG. 3A shows comparative genomic hybridization (CGH) performed to determine genomic content and alteration in cells throughout the HMT-3522 progression series.
FIG. 3B are phase contrast micrographs showing the morphology of mammary epithelial cells (MECs) recapitulated in 3-D rBM assay.
FIG. 3C shows immunostaining with Ki-67 marker.
FIG. 3D shows organized cortical F-actin in S-1 acini and disorganized F-actin filaments in S-2 and T4-2 tumor colonies.
FIG. 3E shows E-cadherin staining pattern in S1, S2 and T4-2 cells.

To determine genomic content and alteration in cells throughout the HMT-3522 progression series, comparative genomic hybridization was performed. Results are seen in FIG. 3A. As shown in FIG. 3A, genetic alteration, e.g., chromosomal amplification and deletion, were accumulated in HMT 3522 cells during tumorigenic progression.

FIG. 3B are phase contrast micrographs showing the morphology of mammary epithelial cells (MECs) as identified at the top of the FIG. 3, i.e., nonmalignant S1 cells (S1-50, S1-110 and S1-175), premalignant S-2 cells (S2-215) and malignant T4-2 passage 25. In this study, cells were grown embedded in a (3-D) laminin-rich basement membrane (BM) for 10 days. At that time, S1 cells formed growth-arrested structures reminiscent of true acini and S2 premalignant and T4-2 tumor cells formed large, irregular colonies.

FIG. 3C shows immunostaining of tested cells for Ki-67, a marker of cell cycle entry. S1 passages 50 and 110 were negative, that is, they did not show any Ki-67 immunostaining, while the percentage of Ki-67 positive cells increased from S1-175 to the T4-2 tumor cells. These results show a loss of growth-arrest control in response to the BM occurs in progression to malignancy. S1-175 cells remained organized, but the acini were larger.

FIG. 3D shows results of staining the cells with F-actin. F-actin phalloidin staining shows organized cortical F-actin in the S1 cells while both S2 premalignant and T4-2 tumor colonies are seen to contain only disorganized actin filaments.

FIG. 3E illustrates E-cadherin studies. E-cadherin immunofluoresence, seen in FIG. 3E, shows organized cell-cell contact staining in the S1 cells, while in both the S2 premalignant and T4-2 tumor colonies, the cells had punctate, dispersed membrane and intracellular stainings.

II. AZU-1 Gene and AZU-1 Encoded Protein

AZU-1 gene has been discovered to be present and expressed in abundance in normal nonmalignant breast cells.

Functional studies indicate that overexpression of the AZU-1 message in tumorigenic T4-2 cells is sufficient to reduce their tumorigenic phenotype as measured by growth in soft agar, invasion assays and by tumor formation in nude mice. Moreover, overexpression of AZU-1 restores T4-2 cells with a normal polarized phenotype when cultured in a 3-dimensional reconstituted basement membrane.

Collectively, these results indicate that AZU-1 gene and/or its protein product is a candidate breast tumor suppressor that may play a role in attenuating cell growth controlling disorganized malignant growth and maintaining appropriate tissue architecture.

A. Isolation, Identification and Sequencing of AZU-1 Gene

The AZU-1 gene has been now identified, isolated, sequenced (SEQ ID NO: 1) and its variant AZU-2 gene (SEQ ID NO: 2) nucleotide sequence has been determined. The sequence of AZU-1 gene is shown in FIG. 4 as SEQ ID NO: 1. The sequence of AZU-2 gene is shown in FIG. 5. Sequences of the related gene TACC2 gene is identified as SEQ ID NO: 5. Other homologs of AZU-1 protein, TACC1 (A), TACC1 (B), TACC3, BCK1 and SB1.8 are identified as SEQ ID NO: 9, SEQ ID NO: 15, SEQ ID NO: 21, SEQ ID NO: 10 and SEQ ID NO: 12, respectively.

1. Sequences of AZU-1 Gene and Variants

AZU-1 gene is localized to a tumor suppressive locus at chromosome 10q 26 genomic locus. AZU-1 is a novel gene whose sequence gives rise to an AZU-1 protein product (SEQ ID NO: 3). The AZU-1 protein comprises 571 amino acids and is comprised of 4 distinct structural/sequence domains, two of which, namely coiled-coil and SPAZI domains, represent conserved motifs. The protein, its amino acid sequence and the four domains as seen in FIG. 6.

AZU-1 gene, of which cDNA is shown in FIG. 4, comprises a nucleotide sequence of 3813 nucleotides. The sequence is identified as SEQ ID NO: 1. The sequence of one of the AZU-1 gene variants, namely, AZU-2 gene is shown in FIG. 5. AZU-2 cDNA sequence is identified as SEQ ID NO: 2. AZU-2 cDNA is longer and contains 4148 nucleotides. The divergent site is between nucleotide 764 and 765. The cDNA of AZU-1 gene variant TACC-2 is identified as SEQ ID NO: 5. Two genes which expressed homologous proteins to AZU-1 protein, namely, TACC-1 and TACC-3 gene, are identified as SEQ ID NO: 18 and SEQ ID NO: 20.

AZU-1 and AZU-2 genes are diverged at a location marked in FIGS. 4 and 5 as "T//T", positioned at nucleotides 429 and 430 of AZU-1 gene and at nucleotides 764 and 765 of AZU-2 gene, respectively. AZU-1 and AZU-2 genes share identical sequence downstream of the divergent site indicated above.

1. AZU-1 Encoded Protein

AZU-1 sequence encodes a protein of 571 amino-acids. Sequence of AZU-1 encoded protein is identified as SEQ ID NO.:3. The AZU-1 variant AZU-2 encodes a protein of 1219 amino acids. Sequence of AZU-2 encoded protein is identified as SEQ ID NO: 4. Another AZU-1 variant TACC1 gene encodes protein identified as SEQ ID NO: 19.

FIG. 6 shows amino acid sequence of the protein encoded by AZU-1 gene (SEQ ID NO: 3).

FIG. 6A identifies amino acids in the sequence and separates them into four domains. The SPAZI domain contains amino acids 1–107 (SEQ ID NO: 7). REGION I (SEQ ID NO: 14) contains amino acids 109–248 (SEQ ID NO: 13). REGION II contains amino acids 250–360. The last and largest coiled-coil domain (CCD) contains amino acids 362–571 (SEQ ID NO: 8).

FIG. 6B is a schematic diagram comparing AZU-1 gene with TACC-1 gene. As seen, there are different degrees of homology in the SPAZI REGION I and coiled-coil domain of AZU-1 and TACC-1. There is a deletion in TACC-1 in the region corresponding to REGION II of AZU-1 gene. FIG. 6C shows point of homology between AZU-1 (SEQ ID NO: 7), TACC-1 (A) (SEQ ID NO: 9), TACC-1 (B) (SEQ ID NO: 15), TACC-3 (SEQ ID NO: 16) and BCK1 (SEQ ID NO: 10) in the SPAZI domain.

Figure 6D:
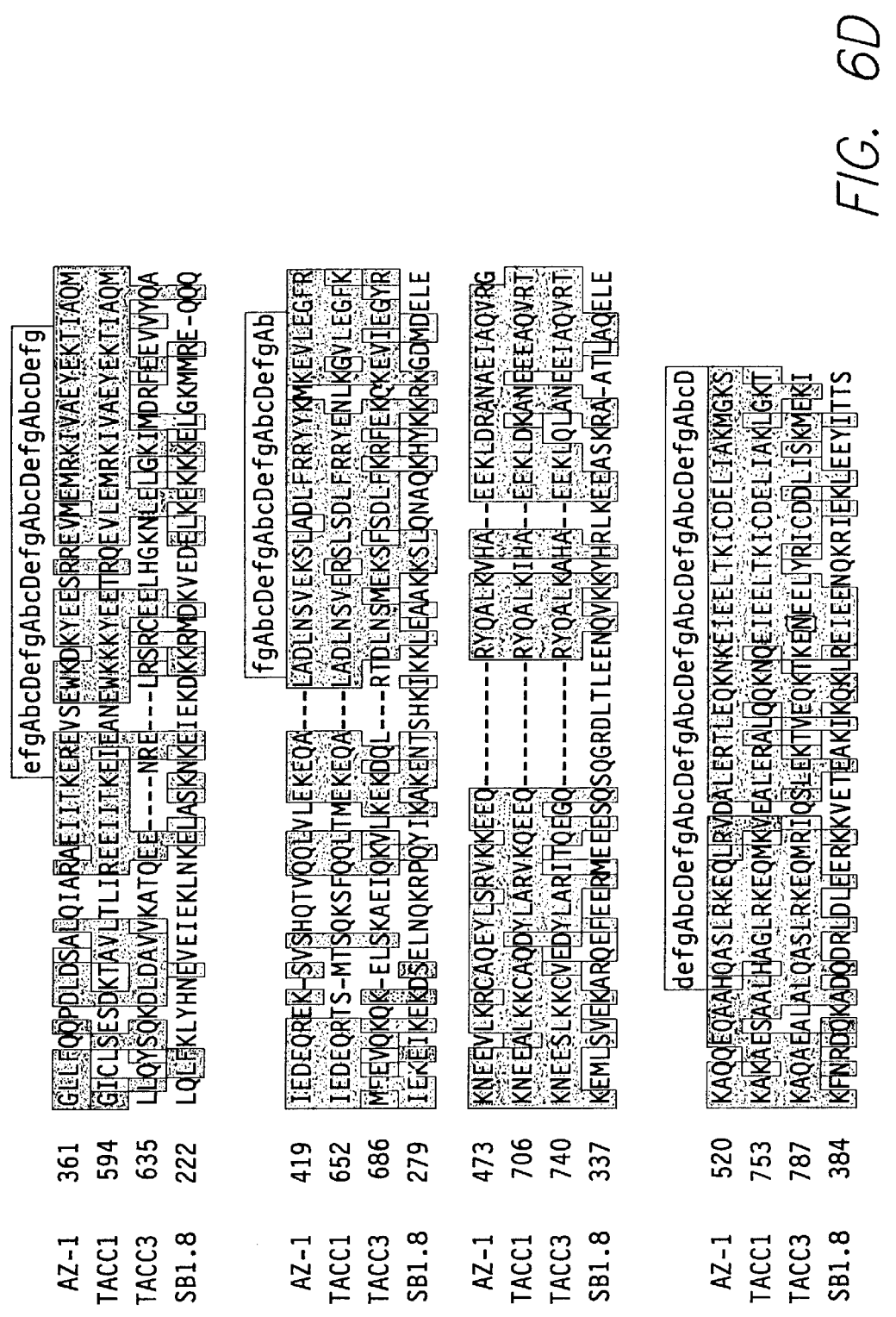

FIG. 6D shows points of homology between AZU-1 (SEQ ID NO: 8), TACC-1 (SEQ ID NO: 11), TACC-3 (SEQ ID NO: 17) and SB1.8 (SEQ ID NO: 12) in coiled-coil domain.

Sequence analysis of the full-length AZU-1 cDNA clone reveals an open reading frame that translates to a protein product of 571 amino acids (FIG. 6A). At its N-terminus AZU-1 contains a novel serine and proline-rich domain, called a SPAZI domain, that is evolutionarily conserved and is predicted to exhibit an Ig-domain like fold. The C-terminal region of AZU-1 displays a series of heptad repeats consistent with the presence of an extensive, but discontinuous, coiled-coil domain.

Using this protein product sequence as the query for a PSI-BLAST database search (*Nucleic Acids Res.*, 25:3389 (1997)), AZU-1 was found to share significant sequence similarity, particularly at its N- and C-termini, to TACC1 gene (Genbank locus AF049910) cDNA (SEQ ID NO: 18), the unpublished product of a gene cloned from the breast cancer amplicon 8p11. A second, unpublished gene product, TACC2 (AF095791) cDNA (SEQ ID NO: 5), seems to be a splice variant of AZU-1 gene since, apart from two insertions, it is identical to AZU-1 at both the nucleic acid and protein levels (FIGS. 19 and 20).

Inspection of the alignment of AZU-1 and TACC1 summarized in FIG. 6B suggests that AZU-1 can be partitioned into four domains. At its N-terminus, AZU-1 exhibits serine- and proline-rich "SPAZI" domain. SPAZI domain is shown in FIG. 6C. The SPAZI domain of AZU-1 is compared to corresponding TACC1 (A), TACC2 (B), TACC3 and BCK1 domains. The serine and proline residues, which are distributed throughout this protein region, each comprise 18% of the AZU-1 sequence content for an overall proline/serine content of 36%. SPAZI domains are present once in AZU-1, twice in TACC1 and once in the *Saccharomyces cerevisiae* gene product BCK1, a member of the MAPKKK (mitigen activator protein kinase kinase kinase) family of serine/threonine kinases. In many instances, the abundant serine and proline residues are conserved in 2 or more of these sequences; 2 serine residues in the second half of the motif are invariant.

Fold recognition studies, using the GenTHREADER program (*J. Mol. Biol.*, 287:797 (1999)), indicate that the SPAZI domain is likely to display an Ig-like beta-sandwich fold. For each SPAZI domain, at least one protein having a known, immunoglobulin-like (Ig-like) structure was reported. The most reliable prediction with estimated probability of correct match=0.59, was for the BCK1 SPAZI domain which matched an Ig-like domain in human Cd2, T lymphocyte adhesion glycoprotein, PDB (Protein Data Bank) identifier 1hnf. Based on these structural predictions, the SPAZI domain seems to be a new member of the hnf or C2-set superfamily.

The SPAZI domain of AZU-1 as seen in FIG. 6B, is followed by two domains, referred to as REGION I and REGION II, that are defined by virtue of their relationship to TACC1. REGION I of AZU-1 shows 20% identity with parallel amino acids of the TACC1 sequence. REGION II corresponds to those sequences of AZU-1 that are absent from TACC1 gene product. Fold recognition analyses of REGION I and REGION II predict that they too have Ig-like folds. AZU-1's REGION I matches known immunoglobulin structures, namely, PDB 1pfc, a fragment of an IgG1 with estimated probability of match=0.32, and PDB 1psk, an antibody Fab fragment, with estimated probability of match=0.51. Analysis of the third region present only in AZU-1 indicates a beta barrel fold, namely, PDB 1htp, H-protein with estimated probability of match=0.27.

The fourth and C-terminal region of AZU-1 displays a series of heptad repeats consistent with the presence of an extensive, but discontinuous, coiled-coil domain seen in FIG. 6D. Structural studies have demonstrated that coiled-coil domains, like the one found in AZU-1, form amphipathic helices that associate with other like domains to form superhelical bundles comprised of anywhere from 2 to 4 helices. The seven structural positions of a heptad repeat are named a–g. Positions a and d, occupied by hydrophobic residues, form the helix interface whereas the remainder are hydrophilic and form the solvent-exposed part of the helix surface.

Apart from the closely related TACC1 coiled-coil domain, the highest scoring sequence from a PSI-BLAST search is the human SB1.8/DXS423E protein, a putative homologue of the *Saccharomyces cerevisiae* SMC-1 protein that is essential for proper chromosomal segregation during mitosis (PIR locus I54383). Alignments generated using the Multicoil program (*Protein Sci.*, 6:1179 (1997)) indicate three major regions where the characteristic heptad repeats fall into register in all three proteins (FIG. 6D). These regions in AZU-1, TACC1 and SB1.8 correspond to regions that the Multicoil program predicts to form dimers (probability >0.90). The two d positions towards the end of the coiled coil are occupied by notably charged residues E and K.

Cellular localization predictions generated using the PSORT program indicate that AZU-1 contains two putative nuclear localization sequences (NLSs). One NLS is positioned N-terminally in the SPAZI domain, while the second NLS starts at amino acid 122 in AZU-1's REGION I shown in FIG. 6A as underlined.

2. AZU-1 Gene Cloning

AZU-1 gene was identified, sequenced and cloned using methods known in the art.

Specifically, the nucleotide sequence of the 180 bp differential display cDNA fragment was determined and compared to existing Genbank sequences. The sequence of the 180 bp fragment was identical to three ESTs. All three sequences contained the 180 bp sequence plus additional 5' and/or 3' sequences; two of these clones exhibited polyadenylation sites. None displayed significant open reading frames, thereby indicating that the 180 bp fragment resided in the 3' untranslated region of the gene product. This information indicated that the remainder of the gene product would be positioned 5' to the isolated fragment and could be cloned by performing multiple rounds of 5' RACE (rapid amplification of cDNA ends), according to protocols from Life Technologies, Inc. Grand Island, N.Y.).

Primers corresponding to the 180 bp differential display fragment were used to initiate the 5' RACE cloning procedure according to the manufacturer's instructions. Ultimately the protocol was repeated 12 times to obtain 3.8 kb of AZU-1 sequence. In each cycle, 500–800 bp of additional overlapping 5'-end sequence was obtained. Sequencing of the 5' RACE PCR products was conducted using cycle sequencing (Amersham Life Science, Cleveland, Ohio). Upon final analysis, the 3.8 kb of AZU-1 sequence contained a candidate translational start codon consistent with the Kozak consensus rules and an inframe stop codon (*Cell*, 34:471 (1983); *Nature*, 308:241 (1984)).

To confirm the composition of the 3.8 kb AZU-1 sequence, and to generate a cDNA containing the entire AZU-1 open reading frame (ORF), primers corresponding to each end of the AZU-1 gene product were utilized in long template PCR (Boehringer Mannheim Corp. Indianapolis, Ind.). In two independent experiments, each using distinct pools of total S1 RNA, the RT-PCR resulted in the amplification 3.8 kb gene products whose sequences were identical to the AZU-1 sequence originally derived using 5' RACE technology. The resulting cDNAs were subcloned into pCR 2.1 (Invitrogen, Carlsbad, Calif.) for further amplification and use.

Other AZU-1 constructs were also prepared. AZU-1 coding region sequences were amplified in polymerase-chain reactions using AZU-1-specific primers supplemented with EcoRI and XhoI restriction sites.

Forward primer: 5' CTGAATTCATGGACCTG-GACTCTGCCCTCCAG 3' (SEQ ID NO: 22).

Reverse primer: 5' GCCTCGAGTTAGGGCTGCTG-GAACAGAAGGCC 3' (SEQ ID NO: 23).

Amplified fragments, once digested with the appropriate enzymes, were ligated into the retroviral expression vector pLXSN (Clontech Inc., Palo Alto, Calif.). Cycle sequencing was performed to verify the sequence fidelity of each AZU-1 construct.

Probable sequence similarities between protein encoded by AZU-1 and other proteins were determined using BLAST computer-driven algorithm that calculates the sequence similarities. Based on the BLAST search results, the sequence of AZU-1 cDNA fragment did not match the cDNA sequences of any known proteins.

To determine whether any one of the GTGs or CTGs located upstream of the first ATG of the AZU-1 open reading frame can be used as an alternate initiator, long and short AZU-1 constructs, pCR-LAZU-1, (nucleotides 403–3325) and pCR-SAZU-1 (nucleotides 1610–3325) were generated. The major products of the in vitro synthesized proteins, using the rabbit reticulocyte lysates (Promega, Inc., Madison, Wis.) of these constructs exhibited a similar size predicated for the short construct (data not shown) suggesting that the first ATG in the deduced open reading frame was likely the translation start site. Based on these results, AZU-1 was predicted to encode a protein spanning 571 amino acids in length.

The BLAST search discovered that a splice variant of AZU-1, TACC2, has been cloned. TACC2 appeared to be isolated as a homolog of TACC1 which was located at 8p11, a breast cancer amplicon. The alignment differences between AZU-1 and TACC2 are shown in FIGS. 19 and 20. TACC2 contains 31 additional upstream residues but no defined translation start site has been indicated. Two sequence insertions were located in the TACC2 protein (FIG. 20). The shorter insertion of DTFR residues was also noted in a small fraction of cDNAs transcribed from the premalignant S2 cell line RNA. The presence of these insertions seems to be characteristic of the premalignant cells and may serve as a marker for detection of premalignancy.

B. Antibody Characterization of Protein Encoded by AZU-1 Gene

This invention demonstrated that polyclonal antibodies directed against AZU-1 specific peptide specifically recognized the protein encoded by the cloned AZU-1 cDNA.

Polyclonal or monoclonal anti-AZU-1 antibodies were prepared using methods known in the art by raising the antibodies against either AZU-1 fusion proteins (full-length or N-terminus, as described below) or immunogenic AZU-1 peptides (amino acids 1–20 or amino acids 131–145). The studies performed during the development of this invention demonstrated the results obtained from using an affinity-purified polyclonal antibody directed against the AZU-1 peptide (amino acids 131–145), hereafter called the anti-AZU-1 antibody. This AZU-1 antibody specifically recognized the protein encoded by the cloned AZU-1 cDNA.

Figure 7:
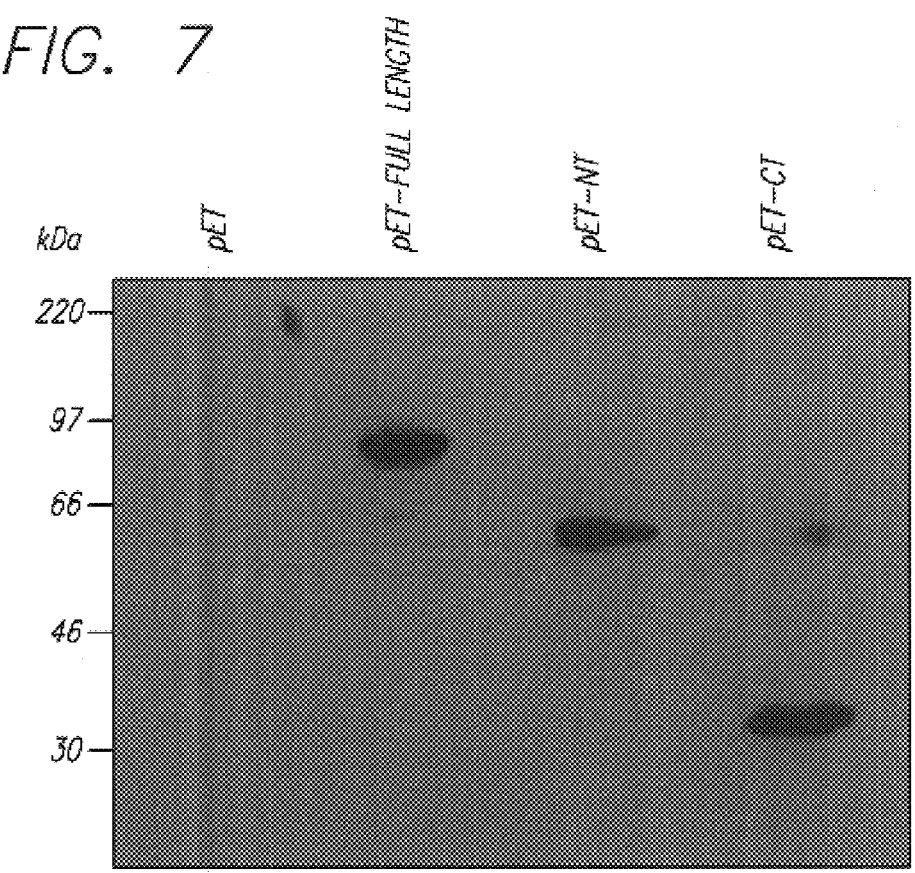
FIG. 7 shows Western blot analysis of AZU-1 recombinant proteins.

For these studies, different AZU-1 cDNA fragments, e.g., full length (pET-full length, nucleotides 1610–3325), N-terminus (pET-NT, nucleotides 1610–2692) and C-terminus (pET-CT, nucleotides 2693–3325) were subcloned into the pET28a+ bacterial expression vector (Novagen, Madison, Wis.) and were expressed in bacteria as a fusion protein containing an N-terminal T7 tag and a polyhistidine epitope. Bacterially-expressed AZU-1 fusion proteins isolated by His-Bind chromatography were analyzed by SDS-PAGE and Western blot hybridization. For each expressed fusion protein, antibody against T7 tag recognized a band corresponding to the protein size predicted for AZU-1 peptide and the N-terminally added T7 and his tag fragments (FIG. 7). On a parallel blot, the affinity-purified AZU-1 antibody (raised against AZU-1 amino acids 131–145) also recognized similar sizes of the full length and N-terminus AZU-1 bacterially expressed products (data not shown). Altogether, these experiments demonstrate that the anti-AZU-1 antibody recognizes the protein encoded by the AZU-1 cDNA.

Figure 8:
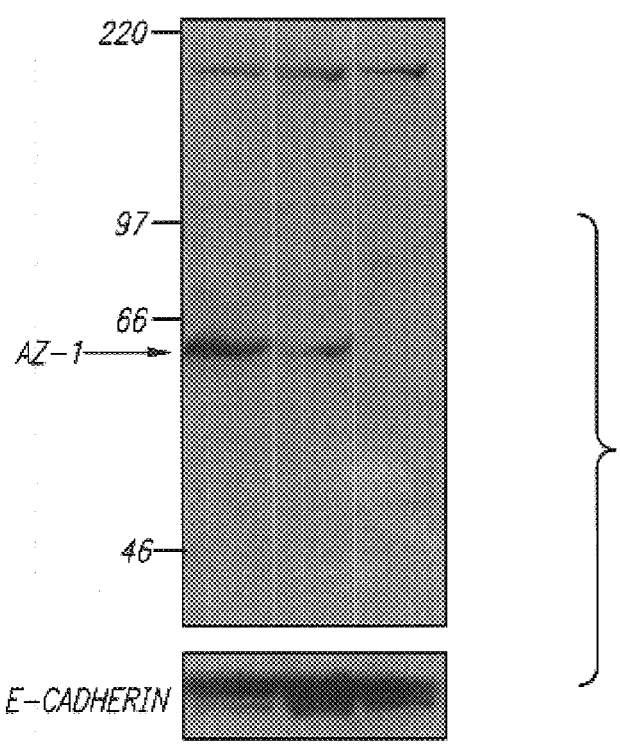
FIG. 8 is a Western blot illustrating recognition of a 64 kD protein by AZU-1 antibody.

Protein encoded by AZU-1 gene in the breast epithelial cells was also characterized by this AZU-1 antibody. FIG. 8 shows the Western blot analysis of AZU-1 protein in the S1 cell lysate with the AZU-1 antibody. Arrow indicates a 64-kd protein recognized by the AZU-1 antibody. To further test its specificity, the antibody was preincubaed with either 15 $\mu$g "+" or 30 $\mu$g "++" or AZU-1 immunogenic peptide before use in hybridization. In the presence of the antigenic peptide, the 64 kDa band was effectively competed away. On the other hand, the intensities of two minor bands (of higher molecular weight), were not diminished by the peptide competition. The results confirm that the 64 kDa band corresponds to the cellular AZU-1 protein.

III. Functionality of AZU-1 Gene

AZU-1 gene was found in abundance in the breast cells and its expression appears to be correlated with breast cell malignancy. The function of AZU-1 gene and its protein was, therefore, investigated.

A. Function of AZU-1 Gene in Breast Cells

Function of the AZU-1 gene was investigated in normal nonmalignant S1 breast cells, in premalignant S2 cells and in breast tumor cells T4-2 obtained as shown in FIG. 1. Results show that a novel gene AZU-1 is expressed in nonmalignant breast cells and the expression is downregulated in malignant breast cells.

First, functionality studies were directed to identifying determinants of tumor progression by differential display.

The HMT-3522 breast culture model has the potential to provide significant insight into the molecular basis of tumor progression. By comparing the gene expression pattern of the model's tumorigenic cell population (HMT-3522-T4-2) with the nonmalignant S1 cell line and with that of its premalignant progenitor (HMT-3522-S2), genes that play a crucial role in the final stages of tumorigenic conversion were identified. Results of these studies are seen in FIG. 9.

FIG. 9 illustrates differential expression of AZU-1 in premalignant and tumor breast cells where FIG. 9A shows differential display of gene messages in premalignant (S2) and tumor (T4-2) cells on a sequencing gel. The arrow indicates a band representing a more intense AZU-1 cDNA fragment in S2 cells than in T4-2 cells, in the absence (−), or in the presence (+) of a reverse transcription reaction (RT).

A PCR-based differential display seen in FIG. 9A strategy was used to screen for genes whose expression varies between S2 and T4-2 cell populations. Using this approach, a 180 bp partial cDNA that was reproducibly present at higher levels in the pre-malignant cell samples than in their tumorigenic counterparts was detected.

To confirm the expression pattern observed in the different display experiments, the cDNA fragment was isolated and used as a probe in Northern blot analyses of total RNA derived from S2 and T4-2 cell cultures seen in FIG. 9B.

FIG. 9B shows Northern blot analysis where the top panel shows that the 4.4-kb AZU-1 message was highly abundant in S2 cells. In contrast, the similar mRNA was greatly reduced in the T4-2 cells. In the bottom panel, the GAPDH probe was used as a control for the amounts of RNA used. Two additional transcripts, 7-kb and 10-kb sizes, present in much less intensity, were also observed. The minor bands may correspond to RNA splice variants or unprocessed RNA species. Consistent with the differential display results, the tumor cell samples displayed a dramatic, more than 10-fold, reduction in the expression of the 4.4 kb message in comparison with the pre-malignant S2 cells.

Using the 180 bp cDNA fragment as starting material, 5' RACE technology was used to recover a full-length cDNA clone. Additional probes derived from the complete cDNA sequence were used to establish the expression pattern of these gene product in the HMT-3522 human breast cell series and in other human breast cells. Results, shown in FIGS. 10A–C, indicate a consistent expression pattern using probes derived from different regions of AZU-1 cDNA sequence.

FIG. 10 shows expression of AZU-1 in nonmalignant breast epithelial cells and downregulation of AZU-1 in breast tumor cells and biopsies. AZU-1 expression patterns in nonmalignant and malignant breast cells were shown by Northern blot analysis.

FIG. 10A shows expression of AZU-1 gene in nonmalignant breast cells, namely, in S1 and MCF10A nonmalignant breast epithelial cell lines, and in primary luminal epithelial (luminal epi) and myoepithelial (myoepi) cells. As seen in FIG. 10A, the 4.4-kb message of AZU-1 gene was present in all nonmalignant breast epithelial cells examined.

Results seen in FIG. 10A show that an abundant and specific 4.4 kb message corresponding to AZU-1 expression was detected not only in the non-malignant human epithelial cell lines, HMT-3522-S1 and MCF10A, but also in primary cultures of human luminal epithelial and myoepithelial cells.

FIG. 10B shows the presence or absence of AZU-1 observed in premalignant S2 and in ten malignant breast epithelial cell lines. T4-1 (T4), HMT3909, MCF-7, CAMA-1, BT-20, MDA-MB-468, SKBR-3, T47D, MDA-MB-231, Hs578t, and BT549 cell lines. The 4.4-kb message of AZU-1 gene was absent in ten breast tumor cell lines examined. The low level of AZU-1 message in HMT3909 cells is probably due to the presence of some contaminating nonmalignant myoepithelial cells (personal communication, Ole Petersen, unpublished data). The RNA from premalignant cells (S2) was used as a positive control and, as expected, shows higher levels of AZU-1 expression.

Results seen in FIG. 10B show that the 4.4 kb message was significantly reduced in the 10 of the 11 breast carcinoma cell lines which were examined.

Gene message level was also examined in in situ ductal breast carcinoma cells. RNAs were isolated from in situ carcinoma in the breast and normal tissue from reduction mammaplasty. Three out of four samples taken from breast cancer patients exhibited a lower level of AZU-1 mRNA than the normal tissue. One sample exhibited a higher AZU-1 message level, presumably from a patient at the premalignant stage. Collectively, the gene expression profiles obtained above for the 4.4 kb transcript are consistent with a role for the identified gene product as a Class II tumor suppressor in breast epithelia.

In order to determine whether AZU-1 gene is tissue specific, that is if it is solely expressed in the breast cells or also in other tissues, expression of AZU-1 in normal human tissues was studied. Results are seen in FIG. 11.

FIG. 11 shows Northern analysis of multiple human tissue RNA blot (Clontech, Inc., Palo alto, Calif.) probed with AZU-1 cDNA fragment. The 4.4-kb AZU-1 message was shown to be expressed in heart, brain, lung, kidney, and pancreas, whereas it was low or absent in placenta, liver, and skeletal muscle. The β-actin probe was used to indicate the amounts of RNA loaded. On a separate multiple human tissue RNA blot from the same source, similar AZU-1 message was shown to be expressed in prostate, testes, and colon. The message was absent or in very low abundance in spleen, thymus, ovary, small intestine, and peripheral blood leukocyte (data not shown).

B. Chromosomal Localization of AZU-1 Gene

Mapping of AZU-1 gene placed AZU-1 gene to chromosome 10q26. Localization of AZU-1 gene to chromosome 10q26 is seen in FIG. 12.

Figure 12:
FIG. 12 is a color image showing localization of AZU-1 gene to chromosome 10q26.

FIG. 12 shows the chromosomal localization of AZU-1 gene by fluorescence in situ hybridization (FISH). The arrows indicate AZU-1 gene is located at chromosome 10q26. Deletions at 10q26, such as by loss of heterozygosity (LOH) correlated with the occurrence of a variety of human cancers, including brain tumors, endometrial carcinoma, and gliobastomas.

C. AZU-1 Association with Cytoskeletal Complexes

Association of AZU-1 with cytoskeletal complexes and its localization in nonmalignant HMT-3522 S1 cells were also studied. Results are shown in FIG. 13.

Figure 13A:
FIG. 13A is the image taken before.

FIG. 13 shows subcellular localization of AZU-1 protein. The immunostaining and fluorescent images were analyzed by confocal microscopy. FIG. 13A shows immunofluorescence images of AZU-1 in S1 cells grown on tissue culture plastic detected by the AZU-1 polyclonal antibody. AZU-1 was found to be present primarily in the cytoplasm and it existed as punctate, occasionally revealed in intense aggregates.

Figure 13B:
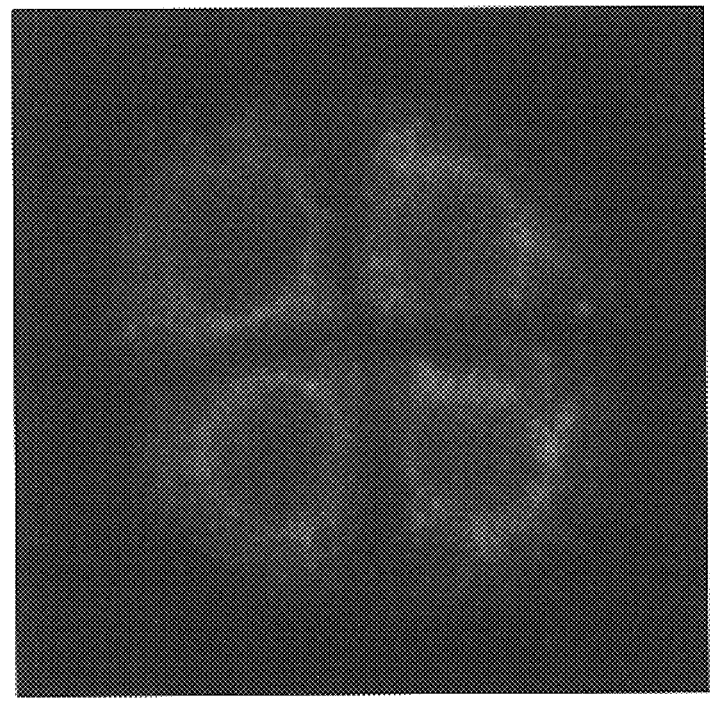
FIG. 13B is the image taken after, treatment with triton X-100 to remove soluble proteins.

FIG. 13B shows that upon treatment with detergent such as Triton X-100, known to remove soluble components in the cytoplasm and nucleus, AZU-1 staining pattern remained, albeit having somewhat lower intensity. These results indicates that AZU-1 may be associated with cytoskeletal complexes.

In situ staining of AZU-1 in human breast tissues is shown in FIG. 14. In these studies, localization of AZU-1 in normal human breast tissues was determined by AZU-1 antibody. FIG. 14, top panel shows the control without the antibody. FIG. 14, middle panel shows that AZU-1 is primarily present in the myoepithelial cells and in low abundance in the luminal epithelial cells of breast acini. Bottom panel shows AZU-1 to be present primarily in the myoepithelial cells of breast ductal tissues. Some AZU-1 protein could also be observed in the luminal epithelial cells.

D. AZU-1 Interaction with E-Cadherin and β-Catenin

AZU-1 interaction with the cell functional proteins, E-cadherin and β-catenin was also explored.

E-cadherin and β-catenin proteins function at cell-cell junctional complexes called adherens junctions. The adherens junctions are localized to sites of cell-cell contact along the lateral surface of epithelial cells. At this site, the adherens junctions interact with the active cytoskeleton and are believed to be crucial for maintaining the integrity of the cell structure. Loss of E-cadherin function correlates with increased cell invasion in many cell types, including the breast cells.

Interactions between adherens junction proteins E-cadherin (E-Cad), β-catenin (β-Cat) and AZU-1 were investigated by coimmunoprecipitation shown in FIG. 15.

AZU-1 polyclonal antibody was used to immunoprecipitate AZU-1 protein in S1 and T4-2 cell lysates. The immunocomplexes were analyzed by SDS-PAGE and detected by Western analysis with AZU-1, β-catenin and E-cadherin antibodies. Left panel shows that the 64-kd AZU-1 protein was immunoprecipitated with AZU-1 antibody. The rabbit IgG (IgG) was used as a control. The same blot when probed with either β-catenin or E-cadherin antibody also detected the presence of both antigens. E-cadherin (lower panel) was used as a control for the amounts of cell lysates loaded. These results suggested the plausible interactions of AZU-1 with adherens junctional complexes, either through E-cadherin or β-catenin.

IV. Suppression and Reversion of Tumorigenicity of T4-2 Cells In Vitro and In Vivo To determine the regulatory function of AZU-1 gene in suppression of tumorigenicity, T4-2 cancer cells were investigated in both in vitro and in vivo assays.

AZU-1 tumor suppression function in vivo and in vitro was assayed using a retroviral gene delivery system to introduce a full length AZU-1 transgene into the HMT-3522 T4-2 tumor cells.

The expression pattern of AZU-1 in non-malignant and tumorigenic cells suggests that AZU-1 may function as a Class II tumor suppressor and that, as such, AZU-1 may affect changes in cellular phenotype by virtue of its expression level.

A. Tumorigenicity Suppression In Vitro

Overexpression of AZU-1 gene in the HMT-3522 tumor cells (T4-2) was tested in order to confirm that such overexpression is sufficient to attenuate their tumorigenic phenotype. Results are seen in FIG. 16.

FIG. 16 illustrates the findings that ectopically-expressed AZU-1 reduces invasiveness in vitro.

Figure 16A:
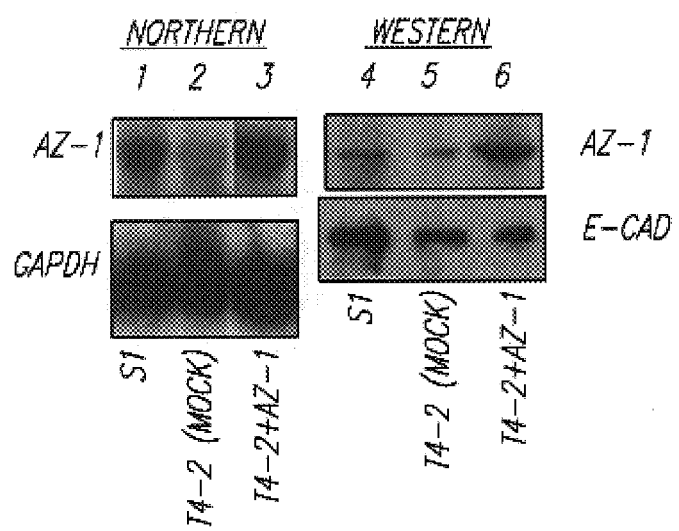
FIG. 16A shows Northern blot of AZU-1 and Western blot of AZU-1 in S1, T4-2 (mock) and T4-2+AZU-1 cells.

In. FIG. 16A, two pooled populations of cells containing stably incorporated DNA were screened for AZU-1 expression by performing Northern analysis of total cellular RNA. In both cases, exogenous expression of the AZU-1 gene in T4-2 cells resulted in the accumulation of AZU-1 message at levels comparable to those observed in the nonmalignant S1 cells. The levels observed in the AZU-1 overexpressed T4-2 cells were 2 to 3-fold higher than AZU-1 mRNA and protein expression in the mock-infected T4-2 cells.

Because the transcript derived from the AZU-1 transgene comigrates on gels with the endogenous AZU-1 gene product (at 4.4 kb), the expressed species were further characterized using transcript specific probes. Results obtained in these studies show that the increased expression observed in the T4-2+AZU-1 cells is entirely attributable to expression from the AZU-1 transgene (data not shown).

Figure 16B:
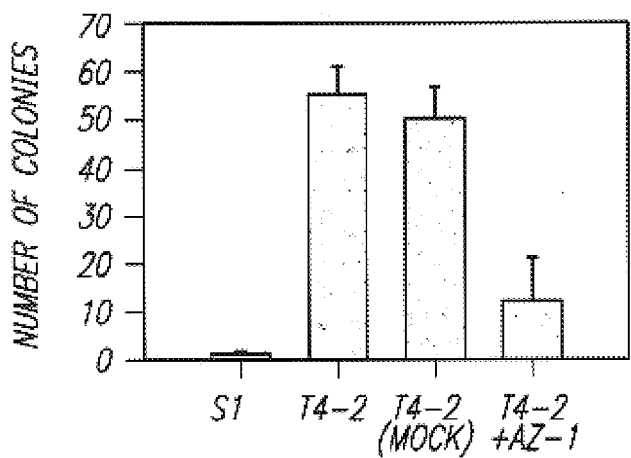
FIG. 16B shows the number of colonies of S1, T4-2, T4-2 (mock) cells and reduction in number of colonies in T4-2 cells in the presence of AZU-1 (T4-2+AZU-1) grown in soft agar.

To test the potential tumor suppressor function of the AZU-1 gene product, assays of anchorage-independent growth, a generally accepted indicator of tumorigenicity in vitro, were performed on the AZU-1-overexpressing T4-2 cells and their unmodified counterparts. Results are seen in FIG. 16B where equal numbers of S1, T4-2, mock-infected T4-2 or T4-2+AZU-1 cells were embedded in semi-solid-agar and, after 4 weeks in culture, the number of viable colonies (>40 μm) was counted.

As expected, non-malignant S1 cells did not support growth in soft agar, whereas their tumorigenic T4-2 cell counterparts (both naive and mock-transfected) exhibited a markedly higher capacity for colony formation and anchorage-independent growth. Consistent with a role for the AZU-1 gene product in tumor suppression, the T4-2 cells overexpressing AZU-1 have shown an 80% diminished potential for growth capacity in soft agar assay, whereas the mock transfectants has around 10% reduction in its growth capacity. Ectopically expressed AZU-1 significantly suppressed tumorigenicity of T4-2 cells in vitro.

Figure 16C:
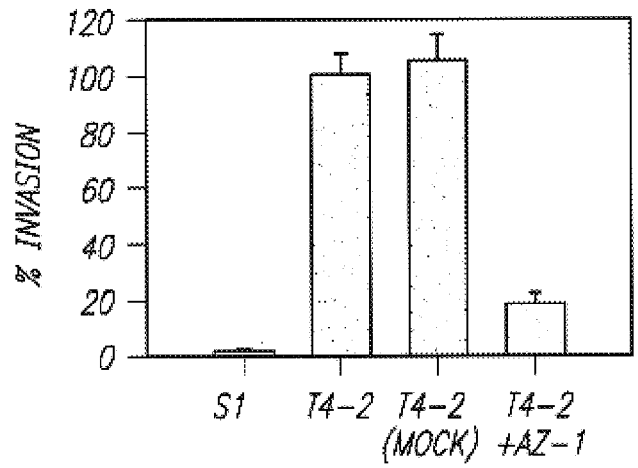
FIG. 16C shows in vitro invasiveness in S1, T4-2, T4-2 (mock) and T4-2+AZU-1 cells.

As an additional test of the tumorigenic cell phenotype, the capacity of the T4-2+AZU-1 cells to invade through basement membrane-coated filters in a modified Boyden chamber assay was performed. Using this approach, HMT-3522-S1 cells were found to be largely non-invasive (Invasion Metastasis, 9:192 (1989)), whereas the tumorigenic T4-2 cells displayed the capacity to migrate effectively through the matrix-coated filters. AZU-1 overexpression diminished the tumor-like behavior of the T4-2 cells, in this case, by attenuating their invasive tendencies to 18% of that displayed by the mock-transfected T4-2 cells (FIG. 16C).

B. Tumorigenicity Suppression In Vivo

In vivo tumorigenicity of T4-A2+AZU-1 cells was examined by injecting the cells subcutaneously into the rear flanks of nude mice. After 6–8 wks post-injection, the mice were inspected for palpable tumors. Results are seen in Table 1.

TABLE 1

| Cell Type | Number of Injected[1] site | Number of Sites with Tumors[2] | Mean Tumor Size (mm$^3$) ± S.E. (n) |
|---|---|---|---|
| S1 | 32 | 0 | 0 (0) |
| T4-2 | 32 | 28 | 250 ± 80 (28) |
| T4-2 + vector | 32 | 28 | 265 ± 95 (28) |
| T4-2 + AZU-1 | 32 | 4 | 38 ± 19 (4) |

[1]Two injection sites per mouse
[2]Lump > 10 mm$^3$

As seen in Table 1, the non-malignant S1 cells failed to give rise to tumors, while the T4-2 cells (naive or mock infected) gave rise to obvious tumor growth in 90% of the injected sites. Mice injected with T4-2 cells overexpressing AZU-1 gave a diminished tumorigenic response with only 4 of the 28 inoculated sites giving rise to detectable tumors. Moreover, the sizes of the T4-2+AZU-1 tumors were much smaller than those observed with the mock-transfected T4-2 cells.

These observations indicate that AZU-1 overexpression in human T4-2 cells is sufficient to reduce the tumorigenic behavior of these cells, both in vivo and in vitro.

C. AZU-1 Upregulation of Expression

Upregulation of AZU-1 expression or overexpression in phenotypically-reverted T4-2 cells was also investigated and AZU-1 overexpression was found to be sufficient to restore normal tissue architecture to tumorigenic MEC cells in culture.

According to *PNAS*, 89:9064 (1992), the behavioral phenotype of non-malignant and tumorigenic primary cultures or immortalized cell lines can be effectively reproduced in the context of a 3-dimensional reconstituted basement membrane assay.

Figure 17A:
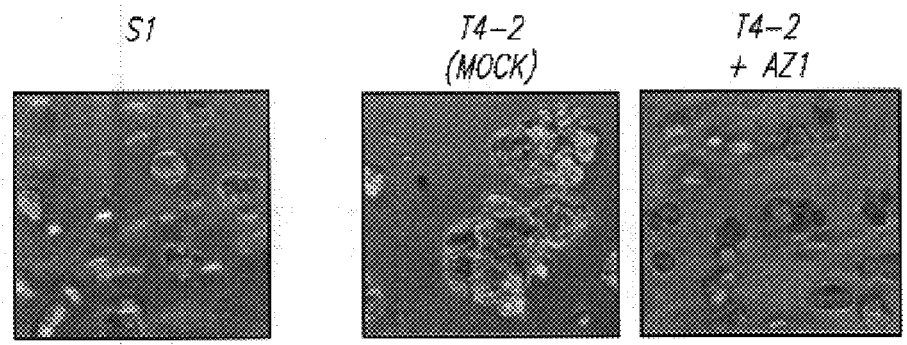
FIG. 17A shows phase contrast images for S1, T4-2 (mock) and T4-2+AZU-1 cells.

Consequently, an additional test of AZU-1's tumor suppressor function was designed to investigate whether overexpression of AZU-1 in T4-2 cells would be sufficient to induce such phenotypic reversion of the HMEC tumor cells in the 3D basement membrane assay. These studies are illustrated in FIG. 17.

Figure 17B:
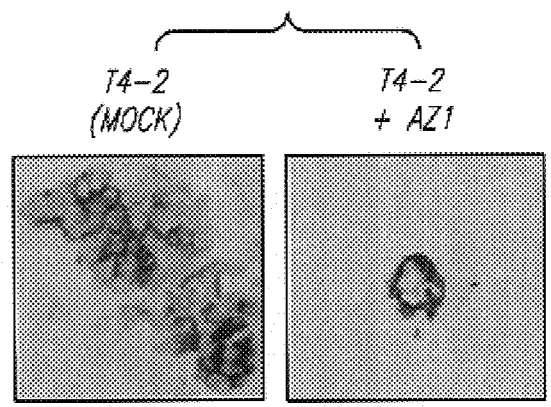
FIG. 17 shows ectopically-expressed AZU-1 induces tissue morphogenesis in three-dimensional cultures.
FIG. 17C shows the colony size in $\mu$m for S1, T4-2 (mock) and T4-2+AZU-1 cells.

S1 cells, the mock-infected cells and AZU-1 expressing-T4-2 cells were embedded in 3-dimensional basement membrane gels. After 10 days in culture, the cell colonies were measured for size and tested with immunofluorescence microscopy. Results show that the S1 cells formed polarized, growth-arrested acinar structures with organized endogenous basement membranes. The mock infected T4-2 cells continued to grow and formed large irregular colonies, as seen in FIG. 17B, that failed to deposit an organized (polarized) endogenous basement membrane. Tumorigenic T4-2 cells, grown under the same conditions, formed large disorganized cell colonies that continued to grow.

When the overexpression of AZU-1 gene was induced in T4-2 cells, the T4-2+AZU-1 colonies underwent phenotypic reversion. They adopted sizes comparable to the S1 cell colonies and were capable of depositing an organized basement membrane at the basal perimeter of the acinar structures. These results, seen in FIG. 17, indicate that AZU-1 overexpression was sufficient not only to reduce the size of the tumor colonies, but also to facilitate the structural reorganization that is required to give rise to polarized, organotypic acinar structures of malignant cells.

Figure 17C:
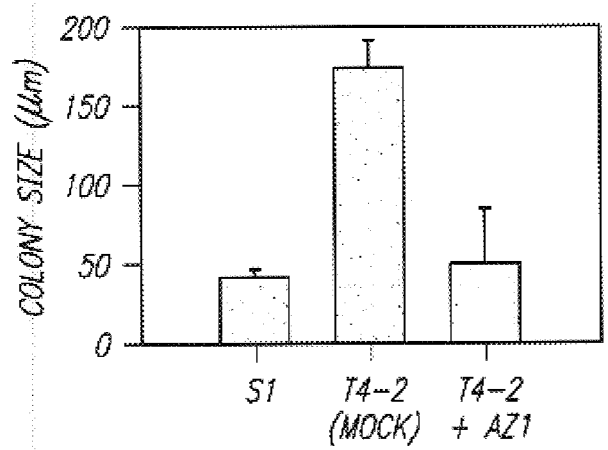

When the colony size was measured in the three above groups, as seen in FIG. 17C, the size of T4-2+AZU-1 colonies reverted to the size of the normal nonmalignant cells.

The acinus-like structure of T4-2+AZU-1 cells in the 3D culture were reminiscent of the morphologically-reverted T4-2 cells in the presence of an inhibitor anti-β1 integrin (A2BII) or an EGFR specific inhibitor (tyrphostin AG1478).

Accordingly, studies were performed to examine whether the AZU-1 message level was modulated in the reverted T4-2 cells.

Phenotypic reversion of T4-2 cells in the 3D rBM assay is dependent on the establishment of bi-direction reciprocal cross-talk between at least three intracellular signal mediators, including β1 integrin, EGFR and MAP kinase (ibid) (*PNAS*, 95:14821 (1998)). Functional inhibition of any one of these elements abrogates the signaling activity of the other two and results in the reduction of total β1 integrin and EGFR protein levels. The AZU-1 gene product might also play a role in the observed cross-talk phenomenon, and its expression might be modulated in the presence of the previously described reverting agents (*J. Of Cell. Biol.*, 137:231 (1997), *PNAS*, 95:14821 (1998)).

Figure 18A:
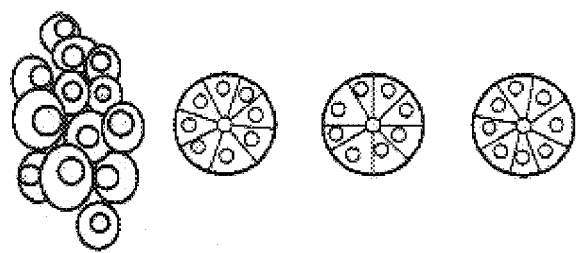
FIG. 18A is a schematic diagram of morphology of T4, S1, T4β1 and T4tyr, phase contrast microscopy (FIG. 18B), AZU-1 message (FIG. 18C) and GADPH message (FIG. 18D).
Figure 18B:
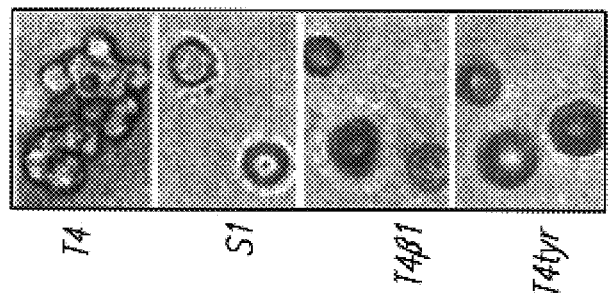
FIG. 18 illustrates upregulation of AZU-1 in morphologically reorganized breast tumor cells.
Figure 18C:
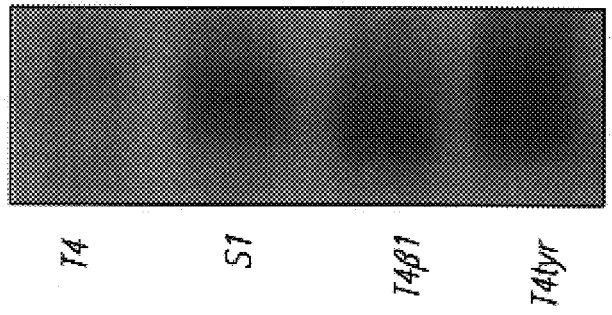
Figure 18D:
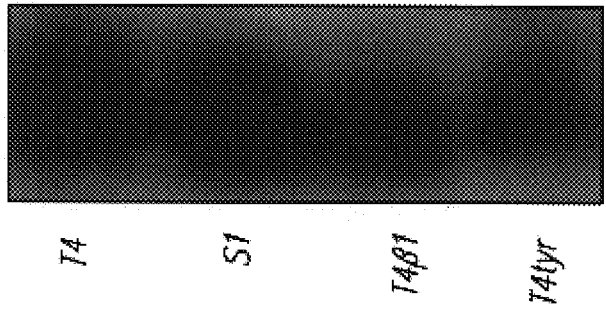

To test this, total RNA was extracted from 3D rBM cultures of S1 cells and T4-2 cells treated with or without inhibitors of either β1 integrin (mAb AIIB2) or EGFR (Tyrphostin). Results are seen in FIG. 18. Northern blot analysis seen in FIG. 18 revealed that AZU-1 levels, while significantly down-modulated in untreated T4-2 cells (FIG. 18C), were restored to S1-like levels in cultures treated with either inhibitors of β1 integrin (T4β1) or EGFR (T4tyr) (FIG. 18C, two right panels). When T4-2 cells were cultured in 3D rBM in the presence of functional inhibitors of β1 integrin or EGFR, the T4-2 cells become "phenotypically reverted", that is they became reorganized to form S1-like organotypic spheres. Collectively, these findings suggest that AZU-1 expression is coupled to β1 integrin and EGFR activity. By virtue of its connections with β1 integrin and EGFR, AZU-1 may provide essential cellular information that dictates cellular structure and phenotype.

In this regard, the 3D rBM assay served as another assay in testing tumor suppression, not only with respect to inhibition of cell growth, but also with respect to restoration of the appropriate tissue polarity and architecture.

D. Detection of AZU-1 Protein in Breast Tumor Biopsies

In order to determine the degree of malignancy in relation to the presence or absence of AZU-1 expressed protein and to determine whether the protein may be useful for detection of malignancy and tumorigenic progression, biopsies were obtained from 19 patients with confirmed stages of breast cancer progression. Results are seen in Table 2.

TABLE 2

| Carcinomas | Malignancy Stage | No. of Samples Tested | No. of AZU-1 Positive |
|---|---|---|---|
| Infiltrating ductal carcinoma | 1 | 6 | 3 |
| Mucinous carcinoma | 1 | 1 | 1 |
| Infiltrating ductal carcinoma | 2 | 6 | 1 |
| Infiltrating ductal carcinoma | 3 | 3 | 0 |
| Medullary carcinoma | 3 | 1 | 0 |
| Metaplastic carcinoma | 3 | 2 | 0 |

Table 2 shows in situ staining of AZU-1 protein in breast tumor biopsies. Nineteen in situ breast carcinoma biopsies with diagnosed mucinous carcinoma (stage 1), infiltrating ductal carcinoma (stage 1, stage 2 and stage 3), medullary carcinoma (stage 3) and metaplastic carcinoma (stage 3), were investigated to determine relative abundance of AZU-1 protein by immunostaining with AZU-1 antibody. The malignancy state of the carcinomas was-graded by a scale of 1 to 3. Number 1 indicates more differentiated and an early stage of malignancy, whereas number 3 indicates samples at a more advanced stage.

The results show that AZU-1 protein was present in 60% (4/7) of breast tumors at early stage 1 of malignancy whereas it was nearly absent (1/12) in the biopsies taken at more advanced state. Specifically, 1 out of 6 samples in the malignancy stage 2 showed the presence of AZU-1 protein. None of the six samples of the advanced stage 3 showed the presence of AZU-1 protein.

V. Methods for Detection, Diagnosis, Treatment, Prophylaxis and a Kit for Diagnosis The current invention further concerns methods for detection of breast cancer, for its treatment and prophylaxis and kits suitable for diagnostic detection of breast cancer growth.

A. A Method For Treatment of Breast Cancer

The proteins encoded by AZU-1 gene or its variants AZU-2 or TACC2 genes were found to be present in large amounts in the normal nonmalignant epithelial breast cells. Its level was found to be significantly decreased or nonexistent in the breast malignant cells.

AZU-1 gene or its variants, which express the protein, are thus actively expressing the protein in nonmalignant cells. Such expression, however, is decreased or absent in malignant breast cells.

The presence of protein expressed by AZU-1 gene, therefore, affects tumorigenicity of the breast tissue and is believed to act, and the findings described herein support its function, as the tumor suppressor.

The method for treatment of breast tumor, thus, comprises providing the subject patient with either the tumor suppressing protein directly targeted to the breast tissue or with genetic material able to express such protein. The protein may be delivered to a patient encapsulated within liposomes or formulated for target delivery using any other targeting means known in the art and used for targeted delivery of drugs to specific organs and tissue.

The second mode for treatment provides the subject patient with genetic material able to express AZU-1 protein. This is typically achieved through gene therapy.

A method for treatment comprises in vivo and ex vivo therapeutic approaches as well as in vivo gene therapy and ex vivo methods.

The gene therapy according to the invention utilizes two approaches. One approach comprises genetic modifications of the tumorigenic cells of a subject to be treated. Such modifications may be induced in the cells in vivo by, for example, developing and transferring a genetic material for expression of the specific protein, or the genetic manipulation may be performed in the subject's own cells or other mammalian cells outside of the body, under ex vivo conditions. The resulting protein then may be imported and delivered to the cells or tissue of the treated subject.

In vivo gene therapy consists of transferring the genetic material directly into the subject's cells.

Ex vivo gene therapy consists of removing cells from the subject and inserting the genetic material into these cells in vitro, prior to replacing the cells in the treated subject.

In the in vivo treatment, cDNA and the expression vectors are prepared. The plasmid encoding the AZU-1 protein is prepared and used to transfect subject's cells. In the cells, the plasmid is transcribed into mRNA and the protein is expressed.

In vivo, thus, the genetic material encoding the protein is transferred directly into the subject's cells or tissue. To ensure the efficiency of the method and expression of the AZU-1 protein at suitably high levels, the coding DNA sequence is engineered to be flanked by an appropriate regulatory sequence such as a viral promoter for ensuring high level expression or tissue specific promoter for ensuring specific organ target.

The transfer of genetic material according to the invention is designed to incorporate AZU-1 gene into breast cells by integrating it into chromosome 10q26. The genetic treatment is intended to permanently alter patient's genetic apparatus ensuring continuous long-term expression of AZU-1 gene.

The method for transfer of genetic material in vivo utilizes, for example, adenovirus vectors, herpes simplex vectors, receptor mediated endocytosis and liposomes, among others, as well as nonviral systems or replication incompetent viruses. Genetic material transfer is achieved, for example, by direct injection, electroporation, particle bombardment, receptor-mediated endocytosis or using liposomes targeted for specific cells or tissues.

In the ex vivo approach, the genetic material, that is AZU-1 cDNA, are built into the expression vector, for example plasmid, cloned and transferred into cells, preferably subject's tumorigenic breast cells, grown in culture, that is grown in vitro and extracorporally. These cells are then transformed and expanded by cell culture in vitro and only then introduced into the subject. To avoid immune system rejection the autologous cells are normally used. For this purpose, the cells are collected initially from the subject to be treated, grown in culture, transformed and reintroduced by implantation into the same subject.

The ex vivo transfer of genetic material is achieved by and utilizes, for example, retrovirus vectors, adeno-associated virus vectors, and to a lesser degree, adenovirus vectors, herpes simplex vectors and liposomes.

The ex vivo transfer of genetic material involves essentially four steps:

(a) cloning a dual-function genetic material into a vector, such as retroviral vector;

(b) transfecting the subject's cells where the targeted AZU-1 protein synthesis is to occur with the genetic material encoding recombinant AZU-1 protein;

(c) verifying the expression of the AZU-1 protein in the cells; and (d) reimplanting these cells in the patient.

The methods used for in vivo gene therapy applicable to the breast cancer therapy according to the invention are known in the art and are described, for example, in *Molecular Biotechnology: Therapeutic Applications and Strategies*, Sunil Maulik, Solil D. Patel, WILEY-LISS, A JOHN WILEY & SONS, Inc., New York, (1997); *Medical Genetics*, pp. 252–257, George H. Sack, McGraw-Hill, New York (1999); *Human Molecular Genetics*, 551–588, T. Strachan, A. P. Read, Bios Scientific Publishers, WILEY-LISS, A JOHN WILEY & SONS, Inc., New York (1998); and *Clinical Trials of Genetic Therapy with Antisense DNA and DNA Vectors*, Ed. Enc Wickstrom, Marcell Decker, Inc., New York (1998), all the above hereby incorporated by reference.

The administration of the genetic material, such as DNA, to the subject is done by means of a composition comprising the cDNA expressing the AZU-1 protein and a pharmaceutically-acceptable carrier and/or other agents such as recombinase enzymes, a lipid agent, a lipid and protein agent, and the like.

Typically, the carrier may comprise solid, liquid or gaseous carriers. Examples of carriers are aqueous solutions, including water, buffered, aqueous solutions and the like.

While it is possible for the cDNA to be administered alone it is preferable to administer it as a pharmaceutical formulation.

In the preferred embodiment of the invention, the DNA of the above composition comprises AZU-1 gene cDNA sequence (SEQ ID NO: 1) encoding the AZU-1 protein.

The delivery of the cDNA into the cell may be conducted by a variety of techniques discussed above. These encompass providing the DNA enveloped by a lipid layer (liposomes), further complexed with a protein and a lipid or a dendrimer.

The complexing the cDNA encoding the protein with lipid, lipid-protein, or dendrimer is especially applicable to in vivo transfection since less cell lethality is encountered, the DNA is protected from DNase degradation and the method is compatible with intracorporeal injection or administration.

One concern about the direct intravenous delivery of genetic material in vivo is the ability of the polynucleotide to survive in circulation long enough to arrive at the desired cellular destination.

In this respect, the coating or masking of the DNA is of extreme utility. The utilization of liposomes, a lipoproteic, or a dendrimer coating is extremely useful. In addition, a successful liposome system uses the cationic lipid reagent dioleyloxytrimethalammonium (DOTMA). DOTMA may be mixed with phosphatidyl ethanolamine (PE) to form the reagent LIPOFECTIN®. When this reagent is utilized to carry the polynucleotides the liposomes are mixed with the DNA and readied for administration.

The DNA may be conveniently enveloped by a lipid layer (liposomes), encapsulated by a lipid and a protein layer, or is complexed to dendrimer. The choice of the foregoing preparations will vary depending on the cell type used, the in vitro, ex vivo or in vivo conditions and the inherent limitations of each transfection method. Preferred conditions for enveloping the cDNA with a lipid layer are as follows. The cDNA is admixed with a lipid such as dioleophosphatidyl ethanolamine, dipalmitoylphosphatidylethanolamine (dipalmitoyl PtdEtn), palmitoyloleoylphosphatidylethanolamine (palmitoyloleoyl PtdEtn), dioleoylphosphatidylcholine (PtdCho), dimyristoylphospatidylethanolamine (dimyristoyl PtdEtn), diphytanoylgeycerophosphatidylethanolamine (diphytanoyl PtdEtn), N-monomethyl PtdEtn, and N-dimethyl PtdEtn in a proportion of about 1 $\mu$g: 1 nmole to 1 $\mu$g: 500 nmoles, in an aqueous solution. Other components and proportions are permissible when this technology is applied to the in vivo method. The pH of the solution may be adjusted to about 8 to 10, and more preferably about 9. In addition to the above, ingredients such as a buffer and other known components may also be added to this composition. The amounts in which these components may be added are standard in the art and need not be further described herein.

In addition to the above, efficient transfer of genetic material requires the targeting of the genetic material encoding the AZU-1 protein to the breast cells. This can be attained by procedures based upon receptor mediated endocytosis according to *J. Biol. Chem.*, 262:4429(1987) or *J. Biol. Chem.*, 263:14, 621 (1988)). This technology utilizes a cell-specific ligand-polylysine complex bound to the DNA polynucleotide sequence through charge interactions. This complex is taken up by the target cells. The successful transfection of a similar hepatoma cell line resulting in stable expression of enzymatic activity following directed targeting was reported in *Biochem. Pharmacol.*, 40:253 (1985)). *PNAS*, (USA), 87:3410 (1990) and *PNAS*, (USA) 88:4255 (1991) utilized a transferrin-polycation to attain the delivery of a plasmid into a human leukemic cell line and observed expression of the encoded luciferase gene. These proteins require attachment to the polynucleotide via, for example, a polylysine linker.

Moreover, in many receptor-mediated systems as chloroquine or other disrupters of intracellular trafficking may be required for high levels of transfection. Adenovirus, for instance, has been used to enhance the delivery of polynucleotides in receptor-mediated systems (*PNAS* (USA), 88:8850 (1991)).

Alternatively, the genetic material may be masked through association with lipids. In one embodiment, the DNA is encased in standard liposomes as described, for example, in U.S. Pat. No. 4,394,448, the relevant portion of the specification of which is hereby incorporated by reference. In another embodiment, the DNA is incubated with a synthetic cationic lipid similar to those described in U.S. Pat. No. 4,897,355. The above-described synthetic cationic lipid effectively mask the DNA when associated therewith. The methods described in the above and below references are hereby incorporated by reference.

The cell recognition element is a molecule capable of recognizing a component on the surface of a targeted cell, covalently linked with a DNA-associating moiety by conventional methods. Cell recognition components include antibodies to cell surface antigens, ligands for cell surface receptors including those involved in receptor-mediated endocytosis, peptide hormones, etc.

Specific ligands contemplated by this invention include carbohydrate ligands such as galactose, mannose, mannosyl 5-phosphate, fucose, sialic groups, N-acetylglucosamine or combinations of these groups as complex carbohydrates such as those found on glycolipids of the blood groups or on various secreted proteins. Other ligands include folate, biotin, various peptides that can interact with cell surface or intracellular receptors such as the chemoattractants peptide containing N-formyl peptides that contain a cystine residue or that interact with cell surface protein such as the human immunodeficiency virus GP-120, and peptides that interact with CD-4.

Other ligands include antibodies or antibody fragments. The specificity of the antibodies can be directed against a variety of epitopes that can be expressed on cell surfaces including histocompatibility, macromolecules, autoimmune antigens, viral, parasitic or bacterial proteins. Other protein ligands include hormones such as growth hormone and insulin or protein growth factors such as GM-CSF, G-CSF, erythropoietin, epidermal growth factor, basic and acidic fibroblast growth factor and the like. Other protein ligands would include various cytokines that work through cell surface receptors such as interleukin 2, interleukin 1, tumor necrosis factor and suitable peptide fragments from such macromolecules.

The membrane-permeabilizing element of this system is a molecule that aids in the passage of a polynucleotide across a membrane. The liposomes, synthetic cationic lipids, lipidproteins, and dendrimer described above as DNA-masking components also may function as membrane-permeabilization components.

Additional membrane-permeabilizing components that will facilitate delivery of the genetic material of this invention also include polycations that neutralize the large negative charge on polynucleotides. Polycations of this invention include polylysine, polyarginine, poly (lysine-arginine) and similar polypeptides, and the polyamines and the polycationic dendrimers.

The membrane-permeabilizing component that facilitates transfer of the protein or DNA of this invention may be an amphiphathic cationic peptide. Amphipathic cationic peptides are peptides whose native configuration is such that the peptide is considered to have a cationic face and a neutral, hydrophobic face. In a preferred embodiment, the peptide is a cyclic peptide. Examples of the amphipathic cationic cyclic peptizes of this invention are gramicidin S, and tyrocidines. The peptide may also contain some or all of the amino acids in the D configuration as opposed to the naturally occurring L configuration.

The membrane permeabilizing elements, i.e., the cyclic peptide and optional phospholipid and polyamine, may be added to the composition simultaneously or consecutively. Preferably, the cyclic peptide is added first, and the phospholipid or polyamine is added later. The molar ratio of added cyclic peptide to added polyamine is preferably from about 1:1 to about 1:3. The molar ratio of added cyclic peptide to added phospholipid is preferably from about 1:1 to about 1:20.

The subcellular-localization element of this system is a molecule capable of recognizing a subcellular component in a targeted cell, covalently linked with a DNA-associating moiety by conventional methods. Particular subcellular components include the nucleus, ribosomes, mitochondria, and chloroplasts. In a preferred embodiment of this invention, the subcellular-localization component is a nuclear-localization component.

The nuclear-localization components include known peptides of defined amino acid sequences, and longer sequences containing these peptides.

For the conventional therapy, the patient is provided with the recombinant AZU-1 protein.

Using either in vitro or ex vivo methods described above and in examples, the AZU-1 recombinant protein is prepared and delivered in the conventional way using pharmaceutically acceptable delivery vehicles and routes. This type of delivery needs to assure that the protein is properly protected from the destruction by digestive proteases when administered orally, or destroyed in the body before it reaches the target breast cells or tissue.

In this mode, the AZU-1 protein may be delivered orally, intravenously, intramuscularly, intraperitoneally, subcutaneously, as aerosol, or using any other mode of delivery known in the art.

In order to avoid the major drawbacks of delivery of proteins, such as instability in the proteolytic environment of the GI tract and poor absorbability through the mucosa, AZU-1 protein containing compositions are preferably prepared as sterile solutions and administered to patients by daily injection. In this particular instance, the protein is prepared ex vivo, isolated, purified and administered to a subject. However, this form of drug delivery could cause pain and inconvenience to patients and thus could be poorly accepted. Many novel delivery systems have been developed to address these problems (*Trends Biotech;*, 16(8): 343–9, (1998), *J. Pharmaceut. Sci*, 87(11): 1331:1334, (1998)). Examples of such deliveries of proteins include, but are not limited to combinations of:

1. Targeted delivery of the protein to cells or tissues to be treated or administered orally, nasally, as injectable, etc., as alternate sites of delivery to a site where the target protein should be delivered.
2. Formulations containing the AZU-1 protein for sustained release.
3. Formulations for administration of concentrated AZU-1 protein into cells at the mucosal surface.
4. Formulations modified for enhanced absorption of the protein into breast cells.
5. Formulation for inhibition of proteolysis including protease inhibitors, chemical modification of the peptide molecule to produce prodrugs and analogs (*Nippon Rinsho. Jap. J. Clin. Med.*, 56(3): 601–7 (1998) and genetic engineering of proteolytically resistant forms.

A number of novel delivery systems have been approved by the FDA (*J. Pharmaceut. Sci.*, 87:1331–4 (1998)). In many cases, a given formulation incorporates elements of several of the above mentioned approaches. Development and optimization of an oral drug delivery systems tends to be specific for each protein or peptide drug. (*J. Pharmaceut. Sci.*, 85:1282–5 (1996)).

Examples of formulations which prevents proteolytic degradation of the AZU-1 protein, sustained release and enhanced absorption follow.

The AZU-1 protein may be delivered via microparticles or microsphere. Gelatin capsules coated with various concentrations of sodium alginate, for example, 20% w/v, and cross-linked with appropriate concentrations of calcium chloride, are resistant to the harsh environment of the stomach and deliver the drug to the distal gastrointestinal tract where drug absorption occurs. (*J. Biomaterials Sci., Polymer Ed.*, 7(1): 39–48 (1995).

The protein can also be incorporated into biodegradable microparticles to reduce the effect of gut secretions and to enable the absorption of the protein in an unaltered form. The uptake of micropartidulates through the gut wall is accepted as a true biological phenomenon but the mechanism and route of uptake have not been established.

Lipid delivery vehicles enhance microparticle uptake and the selective transport of microspheres across M cells (*J. Anatomy*, 189 (Pt3): 487–90 (1996)). Microparticles and microspheres also allow sustained release. Gelatin nanoparticle-poly(lactic-co-glycolic acid) (PLGA) microsphere composites can be prepared by encapsulating protein-loaded gelatin nanoparticles in PLGA microspheres. This encapsulation is conducted by using a phase separation method and a solvent extraction method.

Protein release experiments described in *J. Pharmaceut. Sci.*, 86(8): 891–5 (1997), indicate that this composite system possesses sustained release characteristics. This system also demonstrates the capability of preventing the denaturation of the AZU-1 protein.

Poly(vinyl alcohol) (PVA) hydrogel nanoparticles may be prepared by using a water-in-oil emulsion technology plus cyclic freezing-thawing process. The PVA hydrogel nanoparticles prepared by this method are suitable for the AZU-1 protein drug delivery since formation of the hydrogel does not require crosslinking agents or other adjuvants and does not involve any residual monomer. The PVA hydrogel nanoparticles swell in an aqueous solution and the swelling degree increases with the increase of temperature.

Another route of delivery for AZU-1 protein is through mucoadhesives. Mucoadhesives are polymeric delivery systems for use to concentrate protein and peptide pharmaceuticals at the mucosal surface. Some of the mucoadhesive polymers were found to display other important biological activities, i.e., inhibition of proteolytic enzymes and or modulation of the permeability of usually tight epithelial tissue barriers. Rather than being just adhesives, mucoadhesive polymers may therefore be considered as a novel class of multifunctional macromolecules with a number of desirable properties for their use as biologically active drug delivery adjuvants which are particularly useful in the context of peptide and protein drug delivery.

Carbopol (polyacrylic) polymers with strong bioadhesive properties also can inhibit lumenal degradation of peptide or proteins, offering multiple advantages for their uses in oral drug delivery (*J. Pharm. Pharmacol.*, 48(1): 17–21, (1996), *Pharmaceut. Res*, 12(9): 1293–8 (1995). The mucoadhesive polymers carbomer 934P and chitosan hydrochloride are able to enhance the intestinal absorption of some agents such as buserelin in vivo, and are therefore suitable excipients in peroral delivery system for AZU-1 protein.

Mucoadhesives include monolithic type devices in which the drug is dispersed throughout the polymer and protein-polymer conjugates where the drug is covalently bound to the polymer. Advanced delivery systems include systems containing mucoadhesive polymers providing an intimate contact to the mucosa, thereby reducing the drug degradation between delivery system and absorbing membrane. They also may contain controlled release systems which provide a simultaneous release of protein and inhibitor or inhibitor prodrug or the immobilization of enzyme inhibitors on delivery systems (*J. Controlled Release*, 52(1–2):1–16 (1998); *J. Med. Chem*, 41(13): 2339–44 (1998).

For treatment of the breast cancer, the patient will be provided either with the gene therapy or with the AZU-1 protein formulated as described above.

Treatment regimen would be 1–3 times a day, daily, 1–2 times a week or as needed and will be continued until the normal levels of AZU-1 protein are detectable, until the AZU-1 gene expression is restored and until the tumorigenicity reversion is achieved and confirmed by immunostaining morphological micrography or any other means.

B. A Method For Prophylaxis of Breast Cancer

The method for prophylaxis of cancer growth in the breast cells is achieved in the same way as described above for the treatment.

A patient to be prophylactically treated would have either a family history of the breast cancer or the low level of expression of AZU-1 gene, or the low level of AZU-1 protein will be detected in the biopsy, although there will not yet be any visible, palpable observable or detectable tumor growth.

For prophylaxis, the dosages of the protein will typically be lower than for treatment, treatment will be administered 1–2 times weekly and the patient will be monitored weekly or monthly for AZU-1 gene expression or for the levels of AZU-1 protein in the breast tissue biopsies.

C. A Method For Detection of Breast Cancer

Detection and diagnosis of the breast cancer comprises determining a level of expression of AZU-1 message or detecting a level of protein expressed in breast biopsies.

The level of AZU-1 expression is determined by, for example, in situ hybridization of AZU-1 RNA using a complimentary DNA probe or by RT-PCR assay using gene specific primers according to Example 5.

The level of AZU-1 expressed protein is determined, for example, by detecting with polyclonal or monoclonal AZU-1 antibodies specifically prepared (Example 8) against AZU-1 protein or peptide using indirect immunofluorescence assay as described in Example 18.

D. Kits for Detection and Diagnosis of Breast Cancer

Kits for detection and diagnosis of breast cancer are based on two approaches outlined in Section C, namely, on detecting the AZU-1 protein or on detecting AZU-1 gene message.

1. The Kit for Detection of AZU-1 Protein

The kit for detection of AZU-1 protein in breast biopsies (either cryosections or parafilm embedded blocks) for diagnosis of breast cancer-comprises:

(a) polyclonal or monoclonal anti AZU-1 antibodies;
(b) secondary antibody, e.g. FITC or Texas Red conjugated;
(c) permeabilizing/fixing reagent (optional);
(d) blocking/hybridization solution;
(e) means of tabulating detected AZU-1 protein in the breast tissue samples and correlating the level with the presence, absence, or the stage of breast tumorigenicity.

Examples of results using this kit are shown in FIG. 14 and Table II following the method described in Example 18.

2. The Kit for Detection of AZU-1 Message

The kit for detection of AZU-1 message in breast biopsies for diagnosis of breast cancer comprises components needed for in situ hybridization or for detection of the message by RT reverse transcription PCR.

(A) In situ hybridization kit comprises:
(a) means for preparing intact breast biopsies, e.g., cryosection and mounting condition;
(b) AZU-1 gene specific cDNA probe;
(c) P-actin cDNA as a positive control;
(d) means for labeling of cDNA probes;
(e) means for hybridization/blocking; and
(f) means for tabulating and correlating the detected AZU-1 message levels with the malignant stages of breast cancer patients.

(B) RT-PCR kit comprises:
(a) means for preparing intact breast biopsies, e.g., cryosection and preservation of fresh tissues;
(b) means for RNA extraction from breast biopsies;
(c) AZU-1 gene specific cDNA primers;
(d) means for RT-PCR amplification of RNA extracts;
(e) means for detection of amplified cDNA product, e.g., by ethidium bromide staining/agarose gels;
(f) means for quantification of detected cDNA products; and
(g) means for correlation of obtained values to a degree of tumorigenicity.

UTILITY

The current invention is useful for diagnostic and therapeutic purposes for detection and treatment of human breast cancer. For diagnostic purposes, the level of AZU-1 gene encoded protein is determined in the breast biopsy from the patient. When the amount of AZU-1 protein is high, then there are no tumor cells present in the biopsy. When the AZU-1 encoded protein is absent or at a low level, then there are breast tumor cells present. The protein is useful also as a marker for the malignancy progression. The protein is also useful as a diagnostic marker for tumorigenic reversion in cancer patients undergoing conventional cancer therapy.

The invention is also useful for therapy, particularly gene therapy of breast tumors wherein the specifically targeted AZU-1 gene is introduced into the breast cells, using, for example, retrovial delivery system for gene therapy or the AZU-1 protein is administered in tissue targeted formulation.

EXAMPLE 1

Cell Separation

This example describes the procedure used for cell separation.

Human breast luminal epithelial and myoepithelial cells were purified from organoids after these had spread out to form monolayers in primary culture or had been passaged once. Cells were trypsinized and resuspended in N-(2-hydroxyethyl)piperazine-N'-2-ethanesulfonic acid (HEPES) buffer with 0.5% (W/V) bovine serum albumin (BSA, fraction V, A4919, Sigma) and filtered through a 100 mM nylon mesh (Millipore, Hedehusene, Denmark) to remove residual cell clumps. The cell suspension was incubated 30 minutes at 4° C. with the primary mAb, 115D8, directed against sialomucin (provided by Jo Hilgers, Amsterdam, The Netherlands) or J5 directed against common acute lymphoblastic leukemia antigen (CALLA) or CD10 antigen (Coulter Clone, Struers Kebo Lab., Albertslund, Denmark) diluted 1:100 and 1:10, respectively in HEPES/BSA. The cells were then washed twice in HEPES/BSA and incubated 15 minutes at 4° C. with goat anti-mouse IgG microbeads (AH Diagnostics, Århus, Denmark) diluted 1:5 in HEPES/BSA and washed twice in HEPES/BSA. Cell separation was carried out by use of the MiniMACS magnetic cell separation system obtained from AH Diagnostics according to the kit instructions.

EXAMPLE 2

Cell Culture and Human Luminal Epithelial Cells

This example describes cell culture conditions used for culturing human luminal epithelial cells.

The HMT-3522 human mammary epithelial cells were grown in H14 medium consisting of DMEM/F12 medium (GIBCO/BRL, St. Louis, Mo.) and additives including 250 ng/ml insulin, 10 µg/ml transferrin, 2.6 ng/ml sodium selenite, $10^{-10}$ M estradiol, $1.4\times10^{-6}$ M hydrocortisone, and 5 µg/ml prolactin. The S-1 and MCF10A cells were propagated in H14 medium as monolayers on plastic in the presence of 10 ng/ml epidermal growth factor (EGF) whereas the S2 and T4-2 cells were cultured as monolayers on flasks coated with collagen Type I (Vitrogen 100, Celtrix Laboratories, Palo Alto, Calif.) in the absence of EGF. HMT3909 and MCF-7 cells were cultured as monolayers on collagen type I in DMEM/F12 medium supplemented with $1.4\times10^{-6}$ M hydrocortisone and 2 µM glutamine, respectively. Breast tumor cell lines, e.g., CAMA-1, BT-20, MDA-MB468, SKBR3, T47D, MDA-MB231, Hs578T and BT549, were cultured as monolayers in DMEM/F12 with 5% bovine serum.

Human breast luminal epithelial cells were purified organoids grown as monolayers in primary culture. Three dimensional (3D) cultures were prepared by growing S1, T4-2 cells, and T4-2 transfectants to confluence as monolayers, followed by trypsinization and embedding ($8.5\times10^5$ cells/ml) as single cells into a commercially prepared reconstituted basement membrane (Matrigel, Collaborative Research, Waltham, Mass.) from Englebreth-Holm-Swarm mouse tumors.

EXAMPLE 3

Probe Mapping on Metaphase Chromosome

This example describes probe mapping on metaphore chromosome and primers and procedure used for chromosome localization of AZU-1 gene.

U4 (CGTATGCACTACTGTATTTCCTTTC) (SEQ ID NO: 24) and L3 (GGGCAAGGGCCAAGGTCCAGCAATG) (SEQ ID NO: 25) primers were used to generate 199-bp genomic DNA to screen for P1/BAC/PAC clones to determine location of AZU-1 on human chromosome by fluorescence in situ hybridization (FISH).

P1/BAC/PAC clone was used to determine the location of AZU-1 on human chromosomes. DNA was extracted from an overnight culture using alkaline lysis technique. Probe DNA was labeled with digoxigenin-11-dUTP by nick translation. Hybridization was carried out in the presence of human Cot 1 DNA to suppress the background signal and hybridized to metaphase chromosomes overnight. The hybridized signal was detected by anti-digoxigenin conjugated with FITC. The location of the probes was determined by digital image microscopy following FISH and localized by the fractional length from the p-terminus (FLpter) described previously in *Human Genet*. 83: 335 (1989).

EXAMPLE 4

RNA Extraction, Quantification and Northern Blot Analysis

This example describes conditions and procedures used for RNA isolation and Northern blot analysis.

Total RNA was extracted from cells cultured as monolayers or in 3D rBM or cells from normal tissues or in situ carcinoma with TRIzol reagent (Life Technologies, Inc. Grand Island, N.Y.). For Northern blots, total RNA (20 µg/lane) was resolved on denaturing agarose gels and transferred to Hybond-$N^+$ membranes (Amersham). Resulting blots were hybridized with $^{32}$P-labeled cDNA probes and analyzed by autoradiography. A GAPDH probe was used to normalize variations in loading.

EXAMPLE 5

Differential Display

This example describes conditions used for differential display and RACE cDNA amplification.

Differential display was performed using the RNA image protocol (GenHunter Corp., Nashville, Tenn.) following manufacturer's instructions.

The total RNA (DNA-free) from S2 and T4-2 cell lines was reverse transcribed and the cDNA products were amplified by polymerase chain reaction using the anchored (H-$T_{11}$M, M=A,C,G) and arbitrary primers (H-AP and H-$T_{11}$A) provided in the kit. Amplified products were resolved on 6% acrylamide gels and differential expression of the amplified species was evaluated by autoradiography.

The expression patterns of these two cell lines were observed on the sequencing gel. The differences in the intensity of bands representing differential gene expression were further confirmed by agarose gel electrophoresis analysis of the reamplified cDNA fragments that had been eluted from the gel. To confirm observed differential expression patterns, cDNA fragments of interest were excised from the gel, subject to a second PCR amplification and analyzed on agarose gels. Gene identification of the cDNA products and differences in the message levels were then verified by northern blot analysis.

One of the DNA fragments from the PCR products of H-$T_{11}$A (5-AAGCTTTTTTTTTTTA) SEQ ID NO: 28 and H-AP1 (5'-AAGCTTGATTGCC) SEQ ID NO: 29 primers showed a significantly higher intense band in S2 than in T4-2 cells on both sequencing and agarose gel analyses. Northern blot analysis using this cDNA fragment as a probe confirmed its gene product was greatly more abundant in the S2 cells than in T4-2 cells. Sequence analysis revealed it was novel. This gene has been named AZU-1.

EXAMPLE 6

Rapid Amplification of 5' cDNA Ends (RACE)

This example describes methods used for rapid amplification of 5' cDNA end.

5' RACE system (Life Technologies, Inc. Grand Island, N.Y.) was performed according to the manufacturer's protocol to extend the 5' end of the cDNA length. The procedure was repeated approximately twelve times to map a total length of 3.8 kb of AZU-1 sequence. In each run, 500–800 bp of additional 5'-end sequence was obtained. To further determine the contiquousness and accuracy of AZU-1 sequence, 3.8 kb AZU-1 cDNA fragments were prepared from two separate reverse transcription products using Expand Long Template PCR System (Boehringer Mannheim Corp., Indianapolis, Ind.). A complete match of the sequence of these two cDNA clones confirmed AZU-1 cDNA sequence.

EXAMPLE 7

Sequencing of 5' RACE PCR Products

This example describes sequencing of 5' RACE PCR product.

Sequencing of the 5' RACE PCR products was conducted by thermo sequenase radiolabeled terminator cycle sequencing kit (Amersham Life Science, Cleveland, Ohio). AZU-1 cDNA clones described in Example 6 were sequenced by the sequencing facility in the University of California at Berkeley.

EXAMPLE 8

Preparation of Anti AZU-1 Antibodies

This example describes procedures used for preparation of antibodies against AZU-1 peptides, AZU-1 N-terminal (fragment 1–368), and full length AZU-1 protein.

Polyclonal Antibodies:

AZU-1 polyclonal antibody was raised against an immunogenic peptide AZU-1-A (residues 121–135, KPAKKKKTPLKTVKK) (SEQ ID NO: 26) in rabbits by Animal Pharm Services, Inc. (Healdsburg, Calif.). The immunoglobulin G fraction of the antiserum was further purified by AZU-1 peptide-linked affinity chromatography.

AZU-1 polyclonal antibodies are raised against immunogenic peptides AZU-1-B (residues 1–20, MPLRPPKMKKTPEKLDNTPA) (SEQ ID NO: 27), and purified His-tagged fusion protein containing residues 1–368 of AZU-1 protein fragment in rabbits by ImmunoVision Inc., (Daly City, Calif.). The immunoglobulin G fractions of the antisera are further purified by AZU-1 peptide or purified protein-linked affinity chromatography. The antibody is further purified by affinity chromatography and analyzed by enzyme-linked immunosorbent assay (ELISA).

Monoclonal antibody:

AZU-1 monoclonal antibody is raised against purified His-tagged full length AZU-1 fusion protein in mice by ImmunoVision Inc. The antibody is further purified by affinity chromatography and analyzed by enzyme-linked immunosorbent assay (ELISA).

EXAMPLE 9

Reversion Assays

This example describes reversion assays.

The β1-integrin function-blocking mAb AIIB2 (C. Damsky, UCSF) was introduced into the cell-embedded substratum at a concentration of 100 µg/ml ascites protein (which corresponds to 4–10 µg/ml purified rat IgG1) at the time of Matrigel gelation. Tyrphostin AG 1478 (Calbiochem) dissolved in dimethyl sulfoxide was added to the medium at a concentration of 100 nM on alternate days. Control cultures were treated with mouse IgG and vehicle only for AIIB2 antibody and inhibitor experiments, respectively.

EXAMPLE 10

Immunoblotting and Immunoprecipitation

This example describes immunoblotting and immunoprecipitation methods.

Cells grown as monolayers were lysed in situ in RIPA buffer [1% Nonidet P-40, 0.5% deoxycholate, 0.2% SDS, 150 mM sodium chloride, 50 mM Tris-HCl (pH 7.4) containing 2 mM sodium fluoride, 1 mM sodium orthovanadate, 10 µg/ml E64, and 1 mM Pefabloc]. Cells grown in 3D rBM cultures for 10 days were isolated as colonies with ice-cold PBS/EDTA [0.01 M sodium phosphate (pH 7.2) containing 138 mM sodium chloride and 5 mM EDTA] and thereafter were lysed in RIPA buffer. Protein lysates were resolved upon 7.5% SDS-PAGE gels, electrotransferred to immobilon-P blots (Millipore Corp.) And the blots were then subjected to Western analyses and enhanced chemiluminescence (ECL) (Amersham Corp., Arlington Heights, Ill.) detection. For reprobing, the blots were stripped by incubating in 2% SDS, 62.5 mM Tris-HCl, (pH 6.7), 2-mercaptoethanol, at 50° C. for 30 minutes.

For immunoprecipitation of AZU-1, the RIPA lysates were first precleared by incubating with rabbit IgG and protein A coupled to Sepharose 4B beads (Pharmacia LKB Biotechnology, Inc., Piscataway, N.J.) before immunoprecipitation. The precleared lysates were incubated with affinity-purified polyclonal anti AZU-1 antibodies, monoclonal antibody, or normal rabbit IgG antibodies (negative control) together with protein A coupled to Sepharose-4B beads. Immunoprecipitates were washed five times in RIPA buffer and dissolved in equal volume of 2×SDS sample buffer (0.125M Tris-HCl, 4% SDS, 20% glycerol, 0.02% bromophenol blue, 4% β-mercaptoethanol) for SDS-PAGE analysis and subsequent Western analyses.

EXAMPLE 11

AZU-1 Plasmid Construct

This example describes preparation of plasmid AZU-1 constructs.

pCR-LAZU-1, pCR-SAZU-1, pET- full length AZU-1 pET-NT, pET-CT, and pLXSN-AZU-1 constructs were used. Full length AZU-1 open reading frame (nucleotides 1610–3325) was inserted into SacI-SalI sites of pET28 a(+) vector (Noragen), and EcoRI-XhoI sites of pLXSN vector (Clontech Inc.) to generate pET- full length AZU-1 and pLXSN-AZU-1 constructs.

N-terminus (nucleotides 1610–2692) and C-terminus (nucleotides 2693–3325) of AZU-1 protein sequences were inserted into SacI-SalI sites of pET28 vector to generate pET-NT and pET-CT constructs. Two AZU-1 cDNA sequences, positioned at nucleotides 403–3325 and nucleotides 1610–3325 were inserted into pCR 2.1 vector (Invitrogen) to generate pCR-LAZU-1 and pCR-SAZU-1 constructs.

EXAMPLE 12

Transfection Assay

This example describes methods used for transfection.

PLXSN vector and pLXSN-AZU-1 were transfected into PT60 cells provided in the Retro-X system (Clontech Laboratories, Inc., Palo Alto, Calif.) and the stable virus-packaging PT60 cells were generated by selection with 500 µg/ml G418 (Genetisen; Gibco Inc.). The retrovirus particles collected from the growth media selection of the stably transfected PT67 cells were then used to infect T4-2 cells and stable transfectants were selected in 50 µg/ml G418.

EXAMPLE 13

In Vitro Transcription and Translation

This example describes transcription and translation methods.

The CR-LAZU-1 and pCR-SAZU-1 constructs were used to generate in vitro translated product by a TNT coupled reticulocyte lysate system (Promega, Madison, Wis.).

EXAMPLE 14

Soft Agar Assay

This example describes anchorage-independent growth assay.

S1, T4-2, T4-2 (mock) and T4-2 +AZU-1 cells were seeded at $1\times10^5$ cells/well in 0.35% soft agar on 12-well plate for 4 weeks and the size of the colony was measured by eyepiece. Colonies greater than 40 μm was scored as positive and counted. Four repeats were performed on each cell and the experiments performed in triplicate.

EXAMPLE 15

In Vivo Tumorigenicity

This example describes assay used for testing in vivo tumorigenicity.

S1, T4-2, T4-2 (mock) and T4-2+AZU-1 cells propagated as monolayers were trypsinized and dispersed in DMEM:F12 medium at a concentration of $2.5 \times 10^7$/ml. An aliquot of 100 μl ($2.5 \times 10^6$ cells) was subcutaneously injected into each flank of 4–6 week old BalbC nu/nu mice. The size of nodule on the flank was measured by a caliper and recorded at 6–8 weeks after injection.

EXAMPLE 16

In Vitro Invasion Assay

This example describes assay used for testing in vitro invasion.

8 μM Falcon cell culture PET inserts (Becton Dickinson Labware, Franklin Lakes, N.J.) were coated with 10 μl of 1:2 dilution (50 μg/filter) of matrigel in DMEM/E12. $1 \times 10^5$ of S1, T4-2, T4-2 (mock), T4-2-AZU-1 cells resuspended in 200 μl H14 medium were grown on top of coated insert in 24 well plate. After 18–24 hours, the cells migrated through the matrigel was fixed in glutaldehyde, stained with toluidine blue and counted. Four repeats were performed for each cell line and the experiment was repeated three times.

EXAMPLE 17

Morphogenesis Assessment and Criteria

This example describes assays used for assessment of morphogenesis.

Morphology was assessed in situ by examining the degree of colony organization visually by phase contrast microscopy, and by measuring colony diameter using an eyepiece equipped with a micrometer spindle. Polarity was indicated by the presence of a basally organized basement membrane (BM) as determined by collagen IV and β4-integrin immunostaining.

EXAMPLE 18

Indirect Immunofluorescence

This example describes the procedure used for measurement of indirect immunofluorescence.

Cells or breast tissues were permeabilized in situ (0.5% Triton X-100 in 100 mM NaCl/300 mM sucrose/10 mM PIPES, pH 6.8/5 mM $MgCl_2$ containing 1 mM Pefabloc Sc (AEBSF) (Boehringer Mannheim)/10 g/ml leupeptin/10 μg/ml aprotinin/10 μg trypsin inhibitor type II/250 μM NaF), fixed in 2% paraformaldehyde, and immunostained in the presence or absence of AZU-1 antibody using essentially the assay as described in *J. of Cell Biology*, 137:231 (1997).

EXAMPLE 19

Homology Search and Secondary Structure Prediction Programs

This example describes methods and programs used for homology search and secondary structure prediction.

The gapped BLAST (National Center for Biotechnology Information, NCBI), BEAUTY+BLAST (Baylor College of Medicine), and TFASTA (University of Wisconsin) were the used sequence homology search programs.

Website was used to predict coiled coil structure and to calculate the probability that AZU-1 sequence adopts a coiled-coil conformation.

EXAMPLE 20

AZU-1 Recombinant Proteins

This example describes production of AZU-1 recombinant proteins.

Different AZU-1 cDNA fragments, e.g., full length (pET-full length, nucleotides 1610–3325), N-terminus (pET-NT, nucleotides 1610–2692) and C-terminus (pET-CT, nucleotides 2693–3325) were subcloned into pET 28 bacterial expression vector (Novagen, Madison, Wis.) and were expressed in bacteria as a fusion protein containing an N-terminus T7 tag and a polyhistidine epitope. The expressed proteins in the solubilized bacterial cell lysates were purified by His Bind column chromatography and following the manufacturer's procedures. The AZU-1 recombinant proteins were eluted with 1×elute buffer (150 mM imidazole, 500 mM NaCl, 20 mM Tris-HCl, pH 7.9).

What is claimed is:

1. A method for diagnosis of breast cell malignancy comprising steps of:

(a) detecting, in a patient's tissue, a degree of expression of AZU-1 gene or a level of a protein encoded therein; and (b) correlating the degree of expression of AZU-1 gene with breast cells malignancy wherein the high expression of AZU-1 gene and high level of the protein encoded therein is correlated with nonmalignancy and the low or nonexistent AZU-1 gene expression and a low or nonexistent level of the protein encoded by AZU-1 gene is correlated with malignancy;

(c) wherein the detection of the degree of expression of AZU-1 gene comprises determination of the presence and quantity of a protein depicted by SEQ ID NO: 3.

2. The method of claim 1 wherein a diagnostic detection according to claim 1 is repeated every month to determine malignancy progression.

3. The method of claim 1 wherein the degree of expression of AZU-1 gene is detected by the determination of a presence of AZU-1 DNA sequence depicted by SEQ ID NO: 1.

4. The method of claim 3 wherein the presence of DNA sequence depicted by SEQ ID NO: 1 is determined by in situ hybridization or by reverse transcription polymerase chain reaction (RT-PCR).

5. The method of claim 4 wherein the presence of DNA sequence depicted by SEQ ID NO: 1 is determined by RT-PCR using gene specific primers depicted by the SEQ ID NO: 28 and SEQ ID NO: 29.

6. The method of claim 4 wherein the presence of DNA sequence depicted by SEQ ID NO: 1 is determined by in situ hybridization of AZU-1 RNA using a complimentary DNA probe.

7. The method of claim 2 wherein the detected protein is the protein depicted by SEQ ID NO: 3 encoded by the nucleotide sequence depicted by the sequence SEQ ID NO: 1.

8. The method of claim 2 wherein the presence and quantity of the protein depicted by SEQ ID NO: 3 is detected with a polyclonal or monoclonal anti-AZU-1 antibodies.

9. The method of claim 8 wherein the antibodies are polyclonal.

10. The method of claim 9 wherein the polyclonal anti-AZU-1 antibodies are raised against a protein depicted by SEQ ID NO: 26 or SEQ ID NO: 27.

11. The method of claim 8 wherein the antibodies are monoclonal.

12. The method of claim 11 wherein the monoclonal anti-AZU-1 antibodies are raised against a purified His-tagged full length AZ-1 fusion protein.

13. The method of claim 8 wherein said protein is detected in breast biopsies by contacting a breast tissue with the anti AZU-1 antibody and detecting the presence or absence of the protein by immunostaining.

* * * * *

SEQUENCE LISTING

<160> NUMBER OF SEQ ID NOS: 29

<210> SEQ ID NO 1
<211> LENGTH: 3813
<212> TYPE: DNA
<213> ORGANISM: Homo sapiens

<400> SEQUENCE: 1

```
ggaaagccct ttgcacacat cggcctattg aagcactttg cttgattcag ctattctcct      60
ctcaggacct gcctggatca tcccagcctg tagaatcctg ggtttctgtg gcagtttgtt     120
cttctggtat cacctgctat gctctgaatg tttgtatccc tctcagcccc gaaattcctg     180
tgttgaaatc ctaaccccta aggtgatggt atgaggaggt ggggccttcg ggaggtgatt     240
```

```
aggccataag ggcggagcct ttgtgaatgg gattagtgcc cttataaaaa gaggccccac    300
agcactgcct tgcctcttct gccacgtgaa gatgcagtga gaaggagctg tctgtgaact    360
tggaagggt  cctcatgaga cactgaacct gctggtgcct tgatcttgga cttcccagcc    420
tccagaactt tcacctgtgg cagatgatat catccagccc gctgcccctg cagacctgga    480
aagcccaacc ttagctgcct cttcctacca cagtgatgtt gttggccagg tctctacgga    540
tctgatagcc cagaggagtt ccgattctga agaggcattt gagacccgg  agtcaacgac    600
ccctgtcaaa gctccgccag ctccaccccc accaccccc  gaagtcatcc agaacccga    660
ggtcagcaca cagccacccc cggaagaacc aggatgtggt tctgagacag tccctgtccc    720
tgatggccca cggagcgact cggtggaagg aagtcccttc cgtcccccgt cacacccctt    780
ctctgccgtc ttcgatgaag accagccgat agccagcagt gggacttaca acttggactt    840
tgacaacatt gagcttgtgg ataccttca  gaccttggag cctcgtgcct cagacgctaa    900
gaatcaggag ggcaaagtga acacacggag gaagtccacg gattccgtcc ccatctctaa    960
gtctacactg tcccggtcgc tcagcctgca agccagtgac tttgatggtg cttcttcctc   1020
aggcaatccc gaggccgtgg cccttgcccc agatgcatat agcacgggtt ccagcagtgc   1080
ttctagtacc cttaagcgaa ctaaaaaacc gaggccgcct tccttaaaaa agaaacagac   1140
caccaagaaa cccacagaga cccccccagt gaaggagacg caacaggagc cagatgaaga   1200
gagccttgtc cccagtgggg agaatctagc atctgagacg aaaacggaat ctgccaagac   1260
ggaaggtcct agcccagcct tattggagga cacgcccctt gagcccgctg tggggcccaa   1320
agctgcctgc cctctggact cagagagtgc agaaggggtt gtcccccgg  cttctggagg   1380
tggcagagtg cagaactcac cccctgtcgg gaggaaaacg ctgcctctta ccacggcccc   1440
ggaggcaggg gaggtaaccc catcggatag cgggggggcaa gaggactctc cagccaaagg   1500
gctctccgta aggctggagt ttgactattc tgaggacaag agtagttggg acaaccagca   1560
ggaaaacccc cctcctacca aaaagatagg caaaaagcca gttgccaaaa tgccccctgag   1620
gaggccaaag atgaaaaaga cacccgagaa acttgacaac actcctgcct cacctcccag   1680
atcccctgct gaacccaatg acatccccat tgctaaaggt acttacacct ttgatattga   1740
caagtgggat gaccccaatt ttaaccctt  ttctcccac  tcaaaaatgc aggagtctcc   1800
caaactgccc caacaatcat acaactttga cccagacacc tgtgatgagt ccgttgaccc   1860
ctttaagaca tcctctaaga cccccagctc accttctaaa tccccagcct cctttgagat   1920
cccggccagt gctatggaag ccaatggagt ggacggggat gggctaaaca gcccgccaa    1980
gaagaagaag acgcccctaa agacggtgaa aaagtcgcca aaacggtctc ctctctctga   2040
tccaccttcc caggaccca  ccccagctgc tacaccagaa acaccaccag tgatctctgc   2100
ggtggtccac gccacagatg aggaaaaagct ggcggtcacc aaccagaagt ggacgtgcat   2160
gacagtggac ctagaggctg acaaacagga ctacccgcag ccctcggacc tgtccacctt   2220
tgtaaacgag accaaattca gttcacccac tgaggagttg gattacagaa actcctatga   2280
aattgaatat atggagaaaa ttggctcctc cttacctcag gacgacgatg ccccgaagaa   2340
gcaggccttg taccttatgt ttgacacttc tcaggagagc cctgtcaagt catctcccgt   2400
ccgcatgtca gagtccccga cgccgtgttc agggtcaagt tttgaagaga ctgaagccct   2460
tgtgaacact gctgcgaaaa accagcatcc tgtcccacga ggactggccc ctaaccaaga   2520
gtcacacttg caggtgccag agaaatcctc ccagaaggag ctggaggcca tgggcttggg   2580
```

-continued

```
caccccttca gaagcgattg aaattagaga ggctgctcac ccaacagacg tctccatctc    2640
caaaacagcc ttgtactccc gcatcgggac cgctgaggtg gagaaacctg caggccttct    2700
gttccagcag cccgacctgg actctgccct ccagatcgcc agagcagaga tcataaccaa    2760
ggagagagag gtctcagaat ggaaagataa atatgaagaa agcaggcggg aagtgatgga    2820
aatgaggaaa atagtggccg agtatgaaga gaccatcgct cagatgatag aggacgaaca    2880
gagagagaag tcagtctccc accagacggt gcagcagctg gttctggaga aggagcaagc    2940
cctggccgac ctgaactccg tggagaagtc tctggccgac ctcttcagaa gatatgagaa    3000
gatgaaggag gtcctagaag gcttccgcaa gaatgaagag gtgttgaaga gatgtgcgca    3060
ggagtacctg tcccgggtga agaaggagga gcagaggtac caggccctga aggtgcacgc    3120
ggaggagaaa ctggacaggg ccaatgctga gattgctcag gttcgaggca aggcccagca    3180
ggagcaagcc gcccaccagg ccagcctgcg gaaggagcag ctgcgagtgg acgccctgga    3240
aaggacgctg gagcagaaga ataaagaaat agaagaactc accaagattt gtgacgaact    3300
gattgccaaa atggggaaaa gctaactctg aaccgaatgt tttggactta actgttgcgt    3360
gcaatatgac cgtcggcaca ctgctgttcc tccagttcca tggacaggtt ctgttttcac    3420
tttttcgtat gcactactgt atttcctttc taaataaaat tgatttgatt gtatgcagta    3480
ctaaggagac tatcagaatt tcttgctatt ggtttgcatt ttcctagtat aattcatagc    3540
aagttgacct cagagttcct gtatcaggga gattgtctga ttctctaata aaagacacat    3600
tgctgacctt ggccttgccc tttgtacaca agttcccagg gtgagcagct tttggattta    3660
atatgaacat gtacagcgtg catagggact cttgccttaa ggagtgtaaa cttgatctgc    3720
atttgctgat tgtttttaa aaaaacaaga atgcatgtt tcaaataaaa ttctctattg    3780
taaataaaat ttttctttg gatcttggca ata                                  3813
```

<210> SEQ ID NO 2
<211> LENGTH: 4148
<212> TYPE: DNA
<213> ORGANISM: Homo sapiens

<400> SEQUENCE: 2

```
ggcacgagcg acagtccaca tggtagaaga tggtcctggg actttgctca cacaggggtt     60
ccaggacatg tgccaaggtc cacgtgtgcc ccttctcctc agagggaggt tttgactgtg    120
cctgaggcca acagtgagcc ctggacccct gacacgcttg ggggtgaaag gagacccgga    180
gtcactgctg gcatcttgga aatgcgaaat gccctgggca accagagcac ccctgcacca    240
ccaactggag aagtggcaga cactcccctg gagcctggca aggtggcagg cgctgctggg    300
gaagcagagg gtgacatcac cctgagcaca gctgagacac aggcatgtgc gtccggtgat    360
ctgcctgaag caggtactac gaggacattc tccgttgtgg caggtgactt ggtgctgcca    420
ggaagctgtc aggacccagc ctgctctgac aaggctccgg ggatggaggg tacagctgcc    480
cttcatgggg acagcccagc caggccccag caggataagg agcagccagg acctgagcgc    540
cccattccag ctggggatgg aaggtgtgc gtctcctcac ctccagagcc tgacgaaact    600
cacgacccga agctgcaaca tttggctcca gaagagctcc acactgacag agagagcccc    660
aggcctggcc catccatgtt accttcggtt cctaagaagg atgctccaag agtcatggat    720
aaagtcactt cagatgagac cagaggtgcg gaaggaacag aaagttcacc tgtggcagat    780
gatatcatcc agcccgctgc ccctgcagac ctggaaagcc caaccttagc tgcctcttcc    840
taccacagtg atgttgttgg ccaggtctct acggatctga tagcccagag gagttccgat    900
```

-continued

```
tctgaagagg catttgagac cccggagtca acgacccctg tcaaagctcc gccagctcca    960
cccccaccac cccccgaagt catcccagaa cccgaggtca gcacacagcc acccccggaa   1020
gaaccaggat gtggttctga cacagtccct gtccctgatg gccacggag cgactcggtg    1080
gaaggaagtc ccttccgtcc cccgtcacac cccttctctg ccgtcttcga tgaagaccag   1140
ccgatagcca gcagtgggac ttacaacttg gactttgaca acattgagct tgtggatacc   1200
tttcagacct tggagcctcg tgcctcagac gctaagaatc aggagggcaa agtgaacaca   1260
cggaggaagt ccacggattc cgtccccatc tctaagtcta cactgtcccg gtcgctcagc   1320
ctgcaagcca gtgactttga tggtgcttct tcctcaggca atcccgaggc cgtggccctt   1380
gccccagatg catatagcac gggttccagc agtgcttcta gtaccttaa gcgaactaaa    1440
aaaccgaggc cgccttcctt aaaaaagaaa cagaccacca gaaacccac agagaccccc    1500
ccagtgaagg agacgcaaca ggagccagat gaagagagcc ttgtcccag tggggagaat    1560
ctagcatctg agacgaaaac ggaatctgcc aagacggaag gtcctagccc agccttattg   1620
gaggagacgc cccttgagcc cgctgtgggg cccaaagctg cctgccctct ggactcagag   1680
agtgcagaag gggttgtccc cccggcttct ggaggtggca gagtgcagaa ctcaccccct   1740
gtcgggagga aaacgctgcc tcttaccacg gccccgagg cagggaggt aaccccatcg    1800
gatagcgggg ggcaagagga ctctccagcc aaagggctct ccgtaaggct ggagtttgac   1860
tattctgagg acaagagtag ttgggacaac cagcaggaaa accccctcc taccaaaaag    1920
ataggcaaaa agccagttgc caaaatgccc ctgaggaggc caaagatgaa aaagacaccc   1980
gagaaacttg acaacactcc tgcctcacct cccagatccc ctgctgaacc caatgacatc   2040
cccattgcta aagtactta cacctttgat attgacaagt gggatgaccc caattttaac   2100
cctttttctt ccacctcaaa aatgcaggag tctcccaaac tgccccaaca atcatacaac   2160
tttgacccag acacctgtga tgagtccgtt gaccccttta agacatcctc taagaccccc   2220
agctcacctt ctaaatcccc agcctccttt gagatcccgg ccagtgctat ggaagccaat   2280
ggagtggacg gggatgggct aaacaagccc gccaagaaga agaagacgcc cctaaagacg   2340
gtgaaaaagt cgccaaaacg gtctcctctc tctgatccac cttcccagga ccccacccca   2400
gctgctacac cagaaacacc accagtgatc tctgcggtgg tccacgccac agatgaggaa   2460
aagctggcgg tcaccaacca gaagtggacg tgcatgacag tggacctaga ggctgacaaa   2520
caggactacc cgcagccctc ggacctgtcc acctttgtaa acgagaccaa attcagttca   2580
cccactgagg agttggatta cagaaactcc tatgaaattg aatatatgga gaaaattggc   2640
tcctccttac ctcaggacga cgatgccccg aagaagcagg ccttgtacct tatgtttgac   2700
acttctcagg agagccctgt caagtcatct cccgtccgca tgtcagagtc cccgacgccg   2760
tgttcagggt caagttttga agagactgaa gcccttgtga acactgctgc gaaaaaccag   2820
catcctgtcc cacgaggact ggcccctaac caagagtcac acttgcaggt gccagagaaa   2880
tcctcccaga aggagctgga ggccatgggc ttgggcaccc cttcagaagc gattgaaatt   2940
agagaggctg ctcacccaac agacgtctcc atctccaaaa cagccttgta ctcccgcatc   3000
gggaccgctg aggtggagaa acctgcaggc cttctgttcc agcagcccga cctggactct   3060
gccctccaga tcgccagagc agagatcata accaaggaga gagaggtctc agaatggaaa   3120
gataaatatg aagaaagcag gcgggaagtg atggaaatga ggaaaatagt ggccgagtat   3180
gagaagacca tcgctcagat gatagaggac gaacagagag agaagtcagt ctcccaccag   3240
```

-continued

```
acggtgcagc agctggttct ggagaaggag caagccctgg ccgacctgaa ctccgtggag    3300
aagtctctgg ccgacctctt cagaagatat gagaagatga aggaggtcct agaaggcttc    3360
cgcaagaatg aagaggtgtt gaagagatgt gcgcaggagt acctgtcccg ggtgaagaag    3420
gaggagcaga ggtaccaggc cctgaaggtg cacgcggagg agaaactgga cagggccaat    3480
gctgagattg ctcaggttcg aggcaaggcc cagcaggagc aagccgccca ccaggccagc    3540
ctgcggaagg agcagctgcg agtggacgcc ctggaaagga cgctggagca agaataaa     3600 gaaatagaag aactcaccaa gatttgtgac gaactgattg ccaaaatggg gaaaagctaa    3660
ctctgaaccg aatgttttgg acttaactgt tgcgtgcaat atgaccgtcg gcacactgct    3720
gttcctccag ttccatggac aggttctgtt ttcactttt cgtatgcact actgtatttc     3780 cttttctaaat aaaattgatt tgattgtatg cagtactaag gagactatca gaatttcttg    3840
ctattggttt gcattttcct agtataattc atagcaagtt gacctcagag ttcctgtatc    3900
agggagattg tctgattctc taataaaaga cacattgctg accttggcct tgcccttgt     3960 acacaagttc ccagggtgag cagcttttgg atttaatatg aacatgtaca gcgtgcatag    4020
ggactcttgc cttaaggagt gtaaacttga tctgcatttg ctgatttgtt tttaaaaaaa    4080
caagaaatgc atgtttcaaa taaaattctc tattgtaaat aaaatttttt ctttggatct    4140
tggcaata                                                            4148
```

<210> SEQ ID NO 3
<211> LENGTH: 571
<212> TYPE: PRT
<213> ORGANISM: Homo sapiens

<400> SEQUENCE: 3

```
Met Pro Leu Arg Arg Pro Lys Met Lys Lys Thr Pro Glu Lys Leu Asp
  1               5                  10                  15

Asn Thr Pro Ala Ser Pro Pro Arg Ser Pro Ala Glu Pro Asn Asp Ile
             20                  25                  30

Pro Ile Ala Lys Gly Thr Tyr Thr Phe Asp Ile Asp Lys Trp Asp Asp
         35                  40                  45

Pro Asn Phe Asn Pro Phe Ser Ser Thr Ser Lys Met Gln Glu Ser Pro
     50                  55                  60

Lys Leu Pro Gln Gln Ser Tyr Asn Phe Asp Pro Asp Thr Cys Asp Glu
 65                  70                  75                  80

Ser Val Asp Pro Phe Lys Thr Ser Ser Lys Thr Pro Ser Ser Pro Ser
                 85                  90                  95

Lys Ser Pro Ala Ser Phe Glu Ile Pro Ala Ser Ala Met Glu Ala Asn
            100                 105                 110

Gly Val Asp Gly Asp Gly Leu Asn Lys Pro Ala Lys Lys Lys Lys Thr
        115                 120                 125

Pro Leu Lys Thr Val Lys Lys Ser Pro Lys Arg Ser Pro Leu Ser Asp
    130                 135                 140

Pro Pro Ser Gln Asp Pro Thr Pro Ala Ala Thr Pro Glu Thr Pro Pro
145                 150                 155                 160

Val Ile Ser Ala Val Val His Ala Thr Asp Glu Glu Lys Leu Ala Val
                165                 170                 175

Thr Asn Gln Lys Trp Thr Cys Met Thr Val Asp Leu Glu Ala Asp Lys
            180                 185                 190

Gln Asp Tyr Pro Gln Pro Ser Asp Leu Ser Thr Phe Val Asn Glu Thr
        195                 200                 205
```

-continued

```
Lys Phe Ser Ser Pro Thr Glu Leu Asp Tyr Arg Asn Ser Tyr Glu
    210                 215                 220

Ile Glu Tyr Met Glu Lys Ile Gly Ser Ser Leu Pro Gln Asp Asp
225                 230                 235                 240

Ala Pro Lys Lys Gln Ala Leu Tyr Leu Met Phe Asp Thr Ser Gln Glu
                245                 250                 255

Ser Pro Val Lys Ser Ser Pro Val Arg Met Ser Glu Ser Pro Thr Pro
            260                 265                 270

Cys Ser Gly Ser Ser Phe Glu Glu Thr Glu Ala Leu Val Asn Thr Ala
        275                 280                 285

Ala Lys Asn Gln His Pro Val Pro Arg Gly Leu Ala Pro Asn Gln Glu
    290                 295                 300

Ser His Leu Gln Val Pro Glu Lys Ser Gln Lys Glu Leu Glu Ala
305                 310                 315                 320

Met Gly Leu Gly Thr Pro Ser Glu Ala Ile Glu Ile Arg Glu Ala Ala
                325                 330                 335

His Pro Thr Asp Val Ser Ile Ser Lys Thr Ala Leu Tyr Ser Arg Ile
                340                 345                 350

Gly Thr Ala Glu Val Glu Lys Pro Ala Gly Leu Leu Phe Gln Gln Pro
            355                 360                 365

Asp Leu Asp Ser Ala Leu Gln Ile Ala Arg Ala Glu Ile Ile Thr Lys
370                 375                 380

Glu Arg Glu Val Ser Glu Trp Lys Asp Lys Tyr Glu Glu Ser Arg Arg
385                 390                 395                 400

Glu Val Met Glu Met Arg Lys Ile Val Ala Glu Tyr Glu Lys Thr Ile
                405                 410                 415

Ala Gln Met Ile Glu Asp Glu Gln Arg Glu Lys Ser Val Ser His Gln
            420                 425                 430

Thr Val Gln Gln Leu Val Leu Glu Lys Glu Gln Ala Leu Ala Asp Leu
        435                 440                 445

Asn Ser Val Glu Lys Ser Leu Ala Asp Leu Phe Arg Arg Tyr Glu Lys
    450                 455                 460

Met Lys Glu Val Leu Glu Gly Phe Arg Lys Asn Glu Glu Val Leu Lys
465                 470                 475                 480

Arg Cys Ala Gln Glu Tyr Leu Ser Arg Val Lys Lys Glu Glu Gln Arg
                485                 490                 495

Tyr Gln Ala Leu Lys Val His Ala Glu Glu Lys Leu Asp Arg Ala Asn
            500                 505                 510

Ala Glu Ile Ala Gln Val Arg Gly Lys Ala Gln Gln Glu Gln Ala Ala
        515                 520                 525

His Gln Ala Ser Leu Arg Lys Glu Gln Leu Arg Val Asp Ala Leu Glu
    530                 535                 540

Arg Thr Leu Glu Gln Lys Asn Lys Glu Ile Glu Glu Leu Thr Lys Ile
545                 550                 555                 560

Cys Asp Glu Leu Ile Ala Lys Met Gly Lys Ser
                565                 570
```

<210> SEQ ID NO 4
<211> LENGTH: 1219
<212> TYPE: PRT
<213> ORGANISM: Homo sapiens

<400> SEQUENCE: 4

```
Gly Thr Ser Asp Ser Pro His Gly Arg Arg Trp Ser Trp Asp Phe Ala
1               5                   10                  15
```

His Thr Gly Val Pro Gly His Val Pro Arg Ser Thr Cys Ala Pro Ser
            20                  25                  30

Pro Gln Arg Glu Val Leu Thr Val Pro Glu Ala Asn Ser Glu Pro Trp
        35                  40                  45

Thr Leu Asp Thr Leu Gly Gly Glu Arg Arg Pro Gly Val Thr Ala Gly
    50                  55                  60

Ile Leu Glu Met Arg Asn Ala Leu Gly Asn Gln Ser Thr Pro Ala Pro
65                  70                  75                  80

Pro Thr Gly Glu Val Ala Asp Thr Pro Leu Glu Pro Gly Lys Val Ala
                85                  90                  95

Gly Ala Ala Gly Glu Ala Glu Gly Asp Ile Thr Leu Ser Thr Ala Glu
            100                 105                 110

Thr Gln Ala Cys Ala Ser Gly Asp Leu Pro Glu Ala Gly Thr Thr Arg
        115                 120                 125

Thr Phe Ser Val Val Ala Gly Asp Leu Val Leu Pro Gly Ser Cys Gln
    130                 135                 140

Asp Pro Ala Cys Ser Asp Lys Ala Pro Gly Met Glu Gly Thr Ala Ala
145                 150                 155                 160

Leu His Gly Asp Ser Pro Ala Arg Pro Gln Gln Asp Lys Glu Gln Pro
                165                 170                 175

Gly Pro Glu Arg Pro Ile Pro Ala Gly Asp Gly Lys Val Cys Val Ser
            180                 185                 190

Ser Pro Pro Glu Pro Asp Glu Thr His Asp Pro Lys Leu Gln His Leu
        195                 200                 205

Ala Pro Glu Glu Leu His Thr Asp Arg Glu Ser Pro Arg Pro Gly Pro
    210                 215                 220

Ser Met Leu Pro Ser Val Pro Lys Lys Asp Ala Pro Arg Val Met Asp
225                 230                 235                 240

Lys Val Thr Ser Asp Glu Thr Arg Gly Ala Glu Gly Thr Glu Ser Ser
                245                 250                 255

Pro Val Ala Asp Asp Ile Ile Gln Pro Ala Ala Pro Ala Asp Leu Glu
            260                 265                 270

Ser Pro Thr Leu Ala Ala Ser Ser Tyr His Ser Asp Val Val Gly Gln
        275                 280                 285

Val Ser Thr Asp Leu Ile Ala Gln Arg Ser Ser Asp Ser Glu Glu Ala
    290                 295                 300

Phe Glu Thr Pro Glu Ser Thr Thr Pro Val Lys Ala Pro Pro Ala Pro
305                 310                 315                 320

Pro Pro Pro Pro Glu Val Ile Pro Glu Pro Glu Val Ser Thr Gln
                325                 330                 335

Pro Pro Pro Glu Glu Pro Gly Cys Gly Ser Glu Thr Val Pro Val Pro
            340                 345                 350

Asp Gly Pro Arg Ser Asp Ser Val Glu Gly Ser Pro Phe Arg Pro Pro
        355                 360                 365

Ser His Pro Phe Ser Ala Val Phe Asp Glu Asp Gln Pro Ile Ala Ser
    370                 375                 380

Ser Gly Thr Tyr Asn Leu Asp Phe Asp Asn Ile Glu Leu Val Asp Thr
385                 390                 395                 400

Phe Gln Thr Leu Glu Pro Arg Ala Ser Asp Ala Lys Asn Gln Glu Gly
                405                 410                 415

Lys Val Asn Thr Arg Arg Lys Ser Thr Asp Ser Val Pro Ile Ser Lys
            420                 425                 430

-continued

Ser Thr Leu Ser Arg Ser Leu Ser Leu Gln Ala Ser Asp Phe Asp Gly
       435                 440                 445

Ala Ser Ser Ser Gly Asn Pro Glu Ala Val Ala Leu Ala Pro Asp Ala
        450                 455                 460

Tyr Ser Thr Gly Ser Ser Ala Ser Ser Thr Leu Lys Arg Thr Lys
465                 470                 475                 480

Lys Pro Arg Pro Pro Ser Leu Lys Lys Lys Gln Thr Thr Lys Pro
                485                 490                 495

Thr Glu Thr Pro Pro Val Lys Glu Thr Gln Gln Pro Asp Glu Glu
            500                 505                 510

Ser Leu Val Pro Ser Gly Glu Asn Leu Ala Ser Glu Thr Lys Thr Glu
        515                 520                 525

Ser Ala Lys Thr Glu Gly Pro Ser Pro Ala Leu Leu Glu Glu Thr Pro
    530                 535                 540

Leu Glu Pro Ala Val Gly Pro Lys Ala Ala Cys Pro Leu Asp Ser Glu
545                 550                 555                 560

Ser Ala Glu Gly Val Val Pro Ala Ser Gly Gly Arg Val Gln
                565                 570                 575

Asn Ser Pro Pro Val Gly Arg Lys Thr Leu Pro Leu Thr Thr Ala Pro
                580                 585                 590

Glu Ala Gly Glu Val Thr Pro Ser Asp Ser Gly Gly Gln Glu Asp Ser
    595                 600                 605

Pro Ala Lys Gly Leu Ser Val Arg Leu Glu Phe Asp Tyr Ser Glu Asp
    610                 615                 620

Lys Ser Ser Trp Asp Asn Gln Gln Glu Asn Pro Pro Thr Lys Lys
625                 630                 635                 640

Ile Gly Lys Lys Pro Val Ala Lys Met Pro Leu Arg Arg Pro Lys Met
                645                 650                 655

Lys Lys Thr Pro Glu Lys Leu Asp Asn Thr Pro Ala Ser Pro Pro Arg
                660                 665                 670

Ser Pro Ala Glu Pro Asn Asp Ile Pro Ile Ala Lys Gly Thr Tyr Thr
            675                 680                 685

Phe Asp Ile Asp Lys Trp Asp Asp Pro Asn Phe Asn Pro Phe Ser Ser
    690                 695                 700

Thr Ser Lys Met Gln Glu Ser Pro Lys Leu Pro Gln Gln Ser Tyr Asn
705                 710                 715                 720

Phe Asp Pro Asp Thr Cys Asp Glu Ser Val Asp Pro Phe Lys Thr Ser
                725                 730                 735

Ser Lys Thr Pro Ser Ser Pro Ser Lys Ser Pro Ala Ser Phe Glu Ile
            740                 745                 750

Pro Ala Ser Ala Met Glu Ala Asn Gly Val Asp Gly Asp Gly Leu Asn
    755                 760                 765

Lys Pro Ala Lys Lys Lys Thr Pro Leu Lys Thr Val Lys Lys Ser
770                 775                 780

Pro Lys Arg Ser Pro Leu Ser Asp Pro Pro Ser Gln Asp Pro Thr Pro
785                 790                 795                 800

Ala Ala Thr Pro Glu Thr Pro Pro Val Ile Ser Ala Val Val His Ala
                805                 810                 815

Thr Asp Glu Glu Lys Leu Ala Val Thr Asn Gln Lys Trp Thr Cys Met
            820                 825                 830

Thr Val Asp Leu Glu Ala Asp Lys Gln Asp Tyr Pro Gln Pro Ser Asp
    835                 840                 845

Leu Ser Thr Phe Val Asn Glu Thr Lys Phe Ser Ser Pro Thr Glu Glu

```
                850              855              860
Leu Asp Tyr Arg Asn Ser Tyr Glu Ile Glu Tyr Met Glu Lys Ile Gly
865              870                       875                       880

Ser Ser Leu Pro Gln Asp Asp Ala Pro Lys Lys Gln Ala Leu Tyr
                       885                       890                       895

Leu Met Phe Asp Thr Ser Gln Glu Ser Pro Val Lys Ser Ser Pro Val
                       900                       905                       910

Arg Met Ser Glu Ser Pro Thr Pro Cys Ser Gly Ser Ser Phe Glu Glu
                       915                       920                       925

Thr Glu Ala Leu Val Asn Thr Ala Ala Lys Asn Gln His Pro Val Pro
                       930                       935                       940

Arg Gly Leu Ala Pro Asn Gln Glu Ser His Leu Gln Val Pro Glu Lys
945                       950                       955                       960

Ser Ser Gln Lys Glu Leu Glu Ala Met Gly Leu Gly Thr Pro Ser Glu
                       965                       970                       975

Ala Ile Glu Ile Arg Glu Ala Ala His Pro Thr Asp Val Ser Ile Ser
                       980                       985                       990

Lys Thr Ala Leu Tyr Ser Arg Ile Gly Thr Ala Glu Val Glu Lys Pro
                       995                       1000                       1005

Ala Gly Leu Leu Phe Gln Gln Pro Asp Leu Asp Ser Ala Leu Gln Ile
    1010                       1015                       1020

Ala Arg Ala Glu Ile Ile Thr Lys Glu Arg Glu Val Ser Glu Trp Lys
1025                       1030                       1035                       1040

Asp Lys Tyr Glu Glu Ser Arg Arg Glu Val Met Glu Met Arg Lys Ile
                       1045                       1050                       1055

Val Ala Glu Tyr Glu Lys Thr Ile Ala Gln Met Ile Glu Asp Glu Gln
                       1060                       1065                       1070

Arg Glu Lys Ser Val Ser His Gln Thr Val Gln Gln Leu Val Leu Glu
                       1075                       1080                       1085

Lys Glu Gln Ala Leu Ala Asp Leu Asn Ser Val Glu Lys Ser Leu Ala
    1090                       1095                       1100

Asp Leu Phe Arg Arg Tyr Glu Lys Met Lys Glu Val Leu Glu Gly Phe
1105                       1110                       1115                       1120

Arg Lys Asn Glu Glu Val Leu Lys Arg Cys Ala Gln Glu Tyr Leu Ser
                       1125                       1130                       1135

Arg Val Lys Lys Glu Glu Gln Arg Tyr Gln Ala Leu Lys Val His Ala
                       1140                       1145                       1150

Glu Glu Lys Leu Asp Arg Ala Asn Ala Glu Ile Ala Gln Val Arg Gly
                       1155                       1160                       1165

Lys Ala Gln Gln Glu Gln Ala Ala His Gln Ala Ser Leu Arg Lys Glu
    1170                       1175                       1180

Gln Leu Arg Val Asp Ala Leu Glu Arg Thr Leu Glu Gln Lys Asn Lys
1185                       1190                       1195                       1200

Glu Ile Glu Glu Leu Thr Lys Ile Cys Asp Glu Leu Ile Ala Lys Met
                       1205                       1210                       1215

Gly Lys Ser
```

<210> SEQ ID NO 5
<211> LENGTH: 2446
<212> TYPE: DNA
<213> ORGANISM: Homo sapiens

<400> SEQUENCE: 5
tggagtttga ctattctgag gacaagagta gttgggacaa ccagcaggaa aaccccccctc     60

-continued

```
ctaccaaaaa gataggcaaa aagccagttg ccaaaatgcc cctgaggagg ccaaagatga      120
aaaagacacc cgagaaactt gacaacactc ctgcctcacc tcccagatcc cctgctgaac      180
ccaatgacat ccccattgct aaaggtactt acacctttga tattgacaag tgggatgacc      240
ccaattttaa ccctttttct tccacctcaa aaatgcagga gtctcccaaa ctgccccaac      300
aatcatacaa ctttgaccca gacacctgtg atgagtccgt tgaccccttt aagacatcct      360
ctaagacccc cagctcacct tctaaatccc cagcctcctt tgagatccca gccagtgcta      420
tggaagccaa tggagtggac ggggatgggc taaacaagcc cgccaagaag aagaagacgc      480
ccctaaagac tgacacattt agggtgaaaa agtcgccaaa acggtctcct ctctctgatc      540
caccttccca ggaccccacc ccagctgcta ccagaaaac accaccagtg atctctgcgg       600
tggtccacgc cacagatgag gaaaagctgg cggtcaccaa ccagaagtgg acgtgcatga      660
cagtggacct agaggctgac aaacaggact cccgcagcc tcggacctg tccacctttg        720 taaacgagac caaattcagt tcacccactg aggagttgga ttacagaaac tcctatgaaa      780
ttgaatatat ggagaaaatt ggctcctcct tacctcagga cgacgatgcc ccgaagaagc      840
aggccttgta ccttatgttt gacacttctc aggagagccc tgtcaagtca tctcccgtcc      900
gcatgtcaga gtccccgacg ccgtgttcag ggtcaagttt tgaagagact gaagcccttg      960
tgaacactgc tgcgaaaaac cagcatcctg tcccacgagg actggcccct aaccaagagt     1020
cacacttgca ggtgccagag aaatcctccc agaaggagct ggaggccatg ggtttgggca     1080
ccccttcaga agcgattgaa attacagctc ccgagggctc ctttgcctct gctgacgccc     1140
tcctcagcag gctagctcac cccgtctctc tctgtggtgc acttgactat ctggagcccg     1200
acttagcaga aaagaacccc ccactattcg ctcagaaact ccagagagag gctgttcacc     1260
caacagacgt ctccatctcc aaaacagcct tgtactcccg catcgggacc gctgaggtgg     1320
agaaacctgc aggccttctg ttccagcagc ccgacctgga ctctgccctc cagatcgcca     1380
gagcagagat cataaccaag gagagagagg tctcagaatg gaaagataaa tatgaagaaa     1440
gcaggcggga agtgatggaa atgaggaaaa tagtggccga gtatgagaag accatcgctc     1500
agatgataga ggacgaacag agagagaagt cagtctccca ccagacggtg cagcagctgg     1560
ttctggagaa ggagcaagcc ctggccgacc tgaactccgt ggagagtct ctggccgacc      1620 tcttcagaag atatgagaag atgaaggagg tcctagaagg cttccgcaag aatgaagagg     1680
tgttgaagag atgtgcgcag gagtacctgt cccgggtgaa gaaggaggag cagaggtacc     1740
aggccctgaa ggtgcacgcg gaggagaaac tggacagggc caatgctgag attgctcagg     1800
ttcgaggcaa ggcccagcag gagcaagccc ccaccaggc cagcctgcgg aaggagcagc      1860
tgcgagtgga cgccctggaa aggacgctgg agcagaagaa taaagaaata gaagaactca     1920
ccaagatttg tgacgaactg attgccaaaa tggggaaaag ctaactctga accgaatgtt     1980
ttggacttaa ctgttgcggc aatatgaccg tcggcacact gctgttcctc cagttccatg     2040
gacaggttct gttttcactt tttcgtatgc actactgtat ttcctttcta aataaaattg     2100
atttgattgt atgcagtact aaggagacta tcagaatttc ttgctattgg tttgcattt     2160 cctagtataa ttcatagcaa gttgacctca gagttcctgt atcagggaga ttgtctgatt     2220
ctctaataaa agacacattg ctgaccttgg ccttgcccct tgtacacaag ttcccagggt     2280
gagcagcttt tggatttaat atgaacatgt acagcgtgca tagggactct tgccttaagg     2340 agtgtaaaact tgatctgcat ttgctgattt gtttttaaaa aaacaagaaa tgcatgtttc     2400
```

```
aaataaaatt ctctattgta aataaaattt tttctttgga tcttga                    2446
```

<210> SEQ ID NO 6
<211> LENGTH: 653
<212> TYPE: PRT
<213> ORGANISM: Homo sapiens

<400> SEQUENCE: 6

```
Glu Phe Asp Tyr Ser Glu Asp Lys Ser Ser Trp Asp Asn Gln Gln Glu
  1               5                  10                  15

Asn Pro Pro Thr Lys Lys Ile Gly Lys Lys Pro Val Ala Lys Met
                 20                  25                  30

Pro Leu Arg Arg Pro Lys Met Lys Lys Thr Pro Glu Lys Leu Asp Asn
             35                  40                  45

Thr Pro Ala Ser Pro Pro Arg Ser Pro Ala Glu Pro Asn Asp Ile Pro
         50                  55                  60

Ile Ala Lys Gly Thr Tyr Thr Phe Asp Ile Asp Lys Trp Asp Asp Pro
 65                  70                  75                  80

Asn Phe Asn Pro Phe Ser Ser Thr Ser Lys Met Gln Glu Ser Pro Lys
                 85                  90                  95

Leu Pro Gln Gln Ser Tyr Asn Phe Asp Pro Asp Thr Cys Asp Glu Ser
            100                 105                 110

Val Asp Pro Phe Lys Thr Ser Ser Lys Thr Pro Ser Ser Pro Ser Lys
        115                 120                 125

Ser Pro Ala Ser Phe Glu Ile Pro Ala Ser Ala Met Glu Ala Asn Gly
    130                 135                 140

Val Asp Gly Asp Gly Leu Asn Lys Pro Ala Lys Lys Lys Lys Thr Pro
145                 150                 155                 160

Leu Lys Thr Asp Thr Phe Arg Val Lys Lys Ser Pro Lys Arg Ser Pro
                165                 170                 175

Leu Ser Asp Pro Pro Ser Gln Asp Pro Thr Pro Ala Ala Thr Pro Glu
            180                 185                 190

Thr Pro Pro Val Ile Ser Ala Val Val His Ala Thr Asp Glu Glu Lys
        195                 200                 205

Leu Ala Val Thr Asn Gln Lys Trp Thr Cys Met Thr Val Asp Leu Glu
    210                 215                 220

Ala Asp Lys Gln Asp Tyr Pro Gln Pro Ser Asp Leu Ser Thr Phe Val
225                 230                 235                 240

Asn Glu Thr Lys Phe Ser Ser Pro Thr Glu Glu Leu Asp Tyr Arg Asn
                245                 250                 255

Ser Tyr Glu Ile Glu Tyr Met Glu Lys Ile Gly Ser Ser Leu Pro Gln
            260                 265                 270

Asp Asp Asp Ala Pro Lys Lys Gln Ala Leu Tyr Leu Met Phe Asp Thr
        275                 280                 285

Ser Gln Glu Ser Pro Val Lys Ser Ser Pro Val Arg Met Ser Glu Ser
    290                 295                 300

Pro Thr Pro Cys Ser Gly Ser Ser Phe Glu Glu Thr Glu Ala Leu Val
305                 310                 315                 320

Asn Thr Ala Ala Lys Asn Gln His Pro Val Pro Arg Gly Leu Ala Pro
                325                 330                 335

Asn Gln Glu Ser His Leu Gln Val Pro Glu Lys Ser Ser Gln Lys Glu
            340                 345                 350

Leu Glu Ala Met Gly Leu Gly Thr Pro Ser Glu Ala Ile Glu Ile Thr
        355                 360                 365
```

```
Ala Pro Glu Gly Ser Phe Ala Ser Ala Asp Ala Leu Leu Ser Arg Leu
    370                 375                 380

Ala His Pro Val Ser Leu Cys Gly Ala Leu Asp Tyr Leu Glu Pro Asp
385                 390                 395                 400

Leu Ala Glu Lys Asn Pro Pro Leu Phe Ala Gln Lys Leu Gln Arg Glu
                405                 410                 415

Ala Val His Pro Thr Asp Val Ser Ile Ser Lys Thr Ala Leu Tyr Ser
            420                 425                 430

Arg Ile Gly Thr Ala Glu Val Glu Lys Pro Ala Gly Leu Leu Phe Gln
        435                 440                 445

Gln Pro Asp Leu Asp Ser Ala Leu Gln Ile Ala Arg Ala Glu Ile Ile
    450                 455                 460

Thr Lys Glu Arg Glu Val Ser Glu Trp Lys Asp Lys Tyr Glu Glu Ser
465                 470                 475                 480

Arg Arg Glu Val Met Glu Met Arg Lys Ile Val Ala Glu Tyr Glu Lys
                485                 490                 495

Thr Ile Ala Gln Met Ile Glu Asp Glu Gln Arg Glu Lys Ser Val Ser
            500                 505                 510

His Gln Thr Val Gln Gln Leu Val Leu Glu Lys Glu Gln Ala Leu Ala
        515                 520                 525

Asp Leu Asn Ser Val Glu Lys Ser Leu Ala Asp Leu Phe Arg Arg Tyr
    530                 535                 540

Glu Lys Met Lys Glu Val Leu Glu Gly Phe Arg Lys Asn Glu Glu Val
545                 550                 555                 560

Leu Lys Arg Cys Ala Gln Glu Tyr Leu Ser Arg Val Lys Lys Glu Glu
                565                 570                 575

Gln Arg Tyr Gln Ala Leu Lys Val His Ala Glu Glu Lys Leu Asp Arg
            580                 585                 590

Ala Asn Ala Glu Ile Ala Gln Val Arg Gly Lys Ala Gln Gln Glu Gln
        595                 600                 605

Ala Ala His Gln Ala Ser Leu Arg Lys Glu Gln Leu Arg Val Asp Ala
    610                 615                 620

Leu Glu Arg Thr Leu Glu Gln Lys Asn Lys Glu Ile Glu Glu Leu Thr
625                 630                 635                 640

Lys Ile Cys Asp Glu Leu Ile Ala Lys Met Gly Lys Ser
                645                 650

<210> SEQ ID NO 7
<211> LENGTH: 107
<212> TYPE: PRT
<213> ORGANISM: Homo sapiens

<400> SEQUENCE: 7

Met Pro Leu Arg Arg Pro Lys Met Lys Lys Thr Pro Glu Lys Leu Asp
  1               5                  10                  15

Asn Thr Pro Ala Ser Pro Pro Arg Ser Pro Ala Glu Pro Asn Asp Ile
             20                  25                  30

Pro Ile Ala Lys Gly Thr Tyr Thr Phe Asp Ile Asp Lys Trp Asp Asp
         35                  40                  45

Pro Asn Phe Asn Pro Phe Ser Ser Thr Ser Lys Met Gln Glu Ser Pro
     50                  55                  60

Lys Leu Pro Gln Gln Ser Tyr Asn Phe Asp Pro Asp Thr Cys Asp Glu
 65                  70                  75                  80

Ser Val Asp Pro Phe Lys Thr Ser Ser Lys Thr Pro Ser Ser Pro Ser
                 85                  90                  95
```

```
Lys Ser Pro Ala Ser Phe Glu Ile Pro Ala Ser
        100                 105

<210> SEQ ID NO 8
<211> LENGTH: 210
<212> TYPE: PRT
<213> ORGANISM: Homo sapiens

<400> SEQUENCE: 8

Gly Leu Leu Phe Gln Gln Pro Asp Leu Asp Ser Ala Leu Gln Ile Ala
 1               5                  10                  15

Arg Ala Glu Ile Ile Thr Lys Glu Arg Glu Val Ser Glu Trp Lys Asp
            20                  25                  30

Lys Tyr Glu Glu Ser Arg Arg Glu Val Met Glu Met Arg Lys Ile Val
        35                  40                  45

Ala Glu Tyr Glu Lys Thr Ile Ala Gln Met Ile Glu Asp Glu Gln Arg
    50                  55                  60

Glu Lys Ser Val Ser His Gln Thr Val Gln Gln Leu Val Leu Glu Lys
65                  70                  75                  80

Glu Gln Ala Leu Ala Asp Leu Asn Ser Val Glu Lys Ser Leu Ala Asp
                85                  90                  95

Leu Phe Arg Arg Tyr Glu Lys Met Lys Glu Val Leu Glu Gly Phe Arg
            100                 105                 110

Lys Asn Glu Glu Val Leu Lys Arg Cys Ala Gln Glu Tyr Leu Ser Arg
        115                 120                 125

Val Lys Lys Glu Glu Gln Arg Tyr Gln Ala Leu Lys Val His Ala Glu
    130                 135                 140

Glu Lys Leu Asp Arg Ala Asn Ala Glu Ile Ala Gln Val Arg Gly Lys
145                 150                 155                 160

Ala Gln Gln Glu Gln Ala Ala His Gln Ala Ser Leu Arg Lys Glu Gln
                165                 170                 175

Leu Arg Val Asp Ala Leu Glu Arg Thr Leu Glu Gln Lys Asn Lys Glu
            180                 185                 190

Ile Glu Glu Leu Thr Lys Ile Cys Asp Glu Leu Ile Ala Lys Met Gly
        195                 200                 205

Lys Ser
    210

<210> SEQ ID NO 9
<211> LENGTH: 80
<212> TYPE: PRT
<213> ORGANISM: Homo sapiens

<400> SEQUENCE: 9

Gly Asn Ser Cys Pro Glu Leu Val Pro Ser Arg Arg Ser Lys Leu Arg
 1               5                  10                  15

Lys Pro Lys Pro Val Pro Leu Arg Lys Lys Ala Ile Gly Gly Glu Phe
            20                  25                  30

Ser Asp Thr Asn Ala Ala Val Glu Gly Thr Pro Leu Pro Lys Ala Ser
        35                  40                  45

Tyr His Phe Ser Pro Glu Glu Leu Asp Glu Asn Thr Ser Pro Leu Leu
    50                  55                  60

Gly Asp Ala Arg Phe Gln Lys Ser Pro Pro Asp Ile Lys Glu Thr Pro
65                  70                  75                  80

<210> SEQ ID NO 10
```

```
<211> LENGTH: 81
<212> TYPE: PRT
<213> ORGANISM: Homo sapiens

<400> SEQUENCE: 10

Ser Val Ala Ser Thr Lys Ser Ser Lys Ser Pro Arg Ala Thr Ser
 1               5                  10                  15

Arg Lys Ser Ile Tyr Asp Asp Ile Arg Ser Gln Phe Pro Asn Leu Thr
                20                  25                  30

Pro Asn Ser Thr His Ser Gln Phe Tyr Glu Ser Thr Pro Val Ile Glu
             35                  40                  45

Gln Ser Phe Asn Trp Thr Thr Asp Asp His Ile Ser Ala Gly Thr Leu
 50                  55                  60

Glu Asn Pro Thr Ser Phe Thr Asn Ser Ser Tyr Lys Asn Asp Asn Gly
 65                  70                  75                  80

Pro

<210> SEQ ID NO 11
<211> LENGTH: 210
<212> TYPE: PRT
<213> ORGANISM: Homo sapiens

<400> SEQUENCE: 11

Gly Ile Cys Leu Ser Glu Ser Asp Lys Thr Ala Val Leu Thr Leu Ile
 1               5                  10                  15

Arg Glu Glu Ile Ile Thr Lys Glu Ile Glu Ala Asn Glu Trp Lys Lys
                20                  25                  30

Lys Tyr Glu Glu Thr Arg Gln Glu Val Leu Glu Met Arg Lys Ile Val
             35                  40                  45

Ala Glu Tyr Glu Lys Thr Ile Ala Gln Met Ile Glu Asp Glu Gln Arg
 50                  55                  60

Thr Ser Met Thr Ser Gln Lys Ser Phe Gln Gln Leu Thr Met Glu Lys
 65                  70                  75                  80

Glu Gln Ala Leu Ala Asp Leu Asn Ser Val Glu Arg Ser Leu Ser Asp
                85                  90                  95

Leu Phe Arg Arg Tyr Glu Asn Leu Lys Gly Val Leu Glu Gly Phe Lys
            100                 105                 110

Lys Asn Glu Glu Ala Leu Lys Lys Cys Ala Gln Asp Tyr Leu Ala Arg
        115                 120                 125

Val Lys Gln Glu Glu Gln Arg Tyr Gln Ala Leu Lys Ile His Ala Glu
    130                 135                 140

Glu Lys Leu Asp Lys Ala Asn Glu Glu Ile Ala Gln Val Arg Thr Lys
145                 150                 155                 160

Ala Lys Ala Glu Ser Ala Ala Leu His Ala Gly Leu Arg Lys Glu Gln
                165                 170                 175

Met Lys Val Glu Ser Leu Glu Arg Ala Leu Gln Gln Lys Asn Gln Glu
            180                 185                 190

Ile Glu Glu Leu Thr Lys Ile Cys Asp Glu Leu Ile Ala Lys Leu Gly
        195                 200                 205

Lys Thr
    210

<210> SEQ ID NO 12
<211> LENGTH: 223
<212> TYPE: PRT
<213> ORGANISM: Homo sapiens
```

```
<400> SEQUENCE: 12

Leu Gln Leu Phe Lys Leu Tyr His Asn Glu Val Glu Ile Glu Lys Leu
  1               5                  10                  15

Asn Lys Glu Leu Ala Ser Lys Asn Lys Glu Ile Glu Lys Asp Lys Lys
             20                  25                  30

Arg Met Asp Lys Val Glu Asp Glu Leu Lys Glu Lys Lys Lys Glu Leu
         35                  40                  45

Gly Lys Met Met Arg Glu Gln Gln Ile Glu Lys Glu Ile Lys Glu
     50                  55                  60

Lys Asp Ser Glu Leu Asn Gln Lys Arg Pro Gln Tyr Ile Lys Ala Lys
 65                  70                  75                  80

Glu Asn Thr Ser His Lys Ile Lys Lys Leu Glu Ala Ala Lys Lys Ser
                 85                  90                  95

Leu Gln Asn Ala Gln Lys His Tyr Lys Lys Arg Lys Gly Asp Met Asp
                100                 105                 110

Glu Leu Glu Lys Glu Met Leu Ser Val Glu Lys Ala Arg Gln Glu Phe
            115                 120                 125

Glu Glu Arg Met Glu Glu Ser Gln Ser Gln Gly Arg Asp Leu Thr
130                 135                 140

Leu Glu Glu Asn Gln Val Lys Lys Tyr His Arg Leu Lys Glu Glu Ala
145                 150                 155                 160

Ser Lys Arg Ala Ala Thr Leu Ala Gln Glu Leu Glu Lys Phe Asn Arg
                165                 170                 175

Asp Gln Lys Ala Asp Gln Asp Arg Leu Asp Leu Glu Glu Arg Lys Lys
            180                 185                 190

Val Glu Thr Glu Ala Lys Ile Lys Gln Lys Leu Arg Glu Ile Glu Glu
            195                 200                 205

Asn Gln Lys Arg Ile Glu Lys Leu Glu Glu Tyr Ile Thr Thr Ser
210                 215                 220

<210> SEQ ID NO 13
<211> LENGTH: 140
<212> TYPE: PRT
<213> ORGANISM: Homo sapiens

<400> SEQUENCE: 13

Met Glu Ala Asn Gly Val Asp Gly Asp Gly Leu Asn Lys Pro Ala Lys
  1               5                  10                  15

Lys Lys Lys Thr Pro Leu Lys Thr Val Lys Lys Ser Pro Lys Arg Ser
             20                  25                  30

Pro Leu Ser Asp Pro Pro Ser Gln Asp Pro Thr Pro Ala Ala Thr Pro
         35                  40                  45

Glu Thr Pro Pro Val Ile Ser Ala Val Val His Ala Thr Asp Glu Glu
     50                  55                  60

Lys Leu Ala Val Thr Asn Gln Lys Trp Thr Cys Met Thr Val Asp Leu
 65                  70                  75                  80

Glu Ala Asp Lys Gln Asp Tyr Pro Gln Pro Ser Asp Leu Ser Thr Phe
                 85                  90                  95

Val Asn Glu Thr Lys Phe Ser Ser Pro Thr Glu Glu Leu Asp Tyr Arg
                100                 105                 110

Asn Ser Tyr Glu Ile Glu Tyr Met Glu Lys Ile Gly Ser Ser Leu Pro
            115                 120                 125

Gln Asp Asp Asp Ala Pro Lys Lys Gln Ala Leu Tyr
130                 135                 140
```

```
<210> SEQ ID NO 14
<211> LENGTH: 111
<212> TYPE: PRT
<213> ORGANISM: Homo sapiens

<400> SEQUENCE: 14

Met Phe Asp Thr Ser Gln Glu Ser Pro Val Lys Ser Ser Pro Val Arg
  1               5                  10                  15

Met Ser Glu Ser Pro Thr Pro Cys Ser Gly Ser Ser Phe Glu Glu Thr
             20                  25                  30

Glu Ala Leu Val Asn Thr Ala Ala Lys Asn Gln His Pro Val Pro Arg
         35                  40                  45

Gly Leu Ala Pro Asn Gln Glu Ser His Leu Gln Val Pro Glu Lys Ser
     50                  55                  60

Ser Gln Lys Glu Leu Glu Ala Met Gly Leu Gly Thr Pro Ser Glu Ala
 65                  70                  75                  80

Ile Glu Ile Arg Glu Ala Ala His Pro Thr Asp Val Ser Ile Ser Lys
                 85                  90                  95

Thr Ala Leu Tyr Ser Arg Ile Gly Thr Ala Glu Val Glu Lys Pro
            100                 105                 110

<210> SEQ ID NO 15
<211> LENGTH: 87
<212> TYPE: PRT
<213> ORGANISM: Homo sapiens

<400> SEQUENCE: 15

Lys Ser Ala Gly Leu Glu Gln Pro Thr Asp Pro Val Ala Arg Asp Gly
  1               5                  10                  15

Pro Leu Ser Gln Thr Ser Ser Lys Pro Asp Pro Ser Gln Trp Glu Ser
             20                  25                  30

Pro Ser Phe Asn Pro Phe Gly Ser His Ser Val Leu Gln Asn Ser Pro
         35                  40                  45

Pro Leu Ser Ser Glu Gly Ser Tyr His Phe Asp Pro Asp Asn Phe Asp
     50                  55                  60

Glu Ser Met Asp Pro Phe Lys Pro Thr Thr Thr Leu Thr Ser Ser Asp
 65                  70                  75                  80

Phe Cys Ser Pro Thr Gly Asn
             85

<210> SEQ ID NO 16
<211> LENGTH: 91
<212> TYPE: PRT
<213> ORGANISM: Homo sapiens

<400> SEQUENCE: 16

Gly Ala Thr Ser Lys Arg Ala Pro Pro Arg Arg Leu Gly Glu Arg
  1               5                  10                  15

Ser Gly Leu Lys Pro Pro Leu Arg Lys Ala Ala Val Arg Gln Gln Lys
             20                  25                  30

Ala Pro Gln Glu Val Glu Asp Asp Gly Arg Ser Gly Ala Gly Glu
         35                  40                  45

Asp Pro Pro Met Pro Ala Ser Arg Gly Ser Tyr His Leu Asp Trp Asp
     50                  55                  60

Lys Met Asp Asp Pro Asn Phe Ile Pro Phe Gly Gly Asp Thr Lys Ser
 65                  70                  75                  80

Gly Cys Ser Glu Ala Gln Pro Pro Glu Ser Pro
```

<210> SEQ ID NO 17
<211> LENGTH: 203
<212> TYPE: PRT
<213> ORGANISM: Homo sapiens

<400> SEQUENCE: 17

```
Leu Leu Gln Tyr Ser Gln Lys Asp Leu Asp Ala Val Val Lys Ala Thr
  1               5                  10                  15

Gln Glu Glu Asn Arg Glu Leu Arg Ser Arg Cys Glu Glu Leu His Gly
             20                  25                  30

Lys Asn Leu Glu Leu Gly Lys Ile Met Asp Arg Phe Glu Glu Val Val
         35                  40                  45

Tyr Gln Ala Met Glu Glu Val Gln Lys Gln Lys Glu Leu Ser Lys Ala
     50                  55                  60

Glu Ile Gln Lys Val Leu Lys Glu Lys Asp Gln Leu Thr Thr Asp Leu
 65                  70                  75                  80

Asn Ser Met Glu Lys Ser Phe Ser Asp Leu Phe Lys Arg Phe Glu Lys
                 85                  90                  95

Gln Lys Glu Val Ile Glu Gly Tyr Arg Lys Asn Glu Glu Ser Leu Lys
            100                 105                 110

Lys Cys Val Glu Asp Tyr Leu Ala Arg Ile Thr Gln Glu Gly Gln Arg
        115                 120                 125

Tyr Gln Ala Leu Lys Ala His Ala Glu Glu Lys Leu Gln Leu Ala Asn
    130                 135                 140

Glu Glu Ile Ala Gln Val Arg Ser Lys Ala Gln Ala Glu Ala Leu Ala
145                 150                 155                 160

Leu Gln Ala Ser Leu Arg Lys Glu Gln Met Arg Ile Gln Ser Leu Glu
                165                 170                 175

Lys Thr Val Glu Gln Lys Thr Lys Glu Asn Glu Glu Leu Thr Arg Ile
            180                 185                 190

Cys Asp Asp Leu Ile Ser Lys Met Glu Lys Ile
        195                 200
```

<210> SEQ ID NO 18
<211> LENGTH: 7736
<212> TYPE: DNA
<213> ORGANISM: Homo sapiens

<400> SEQUENCE: 18

| | |
|---|---|
| cagaggtcta gcagccgggc gccgcgggcc gggggcctga ggaggccaca ggacgggcgt | 60 |
| cttcccggct agtggagccc ggcgcggggc ccgctgcggc cgcaccgtga ggggaggagg | 120 |
| ccgaggagga cgcggcgccg gctgccggcg ggaggaagcg ctccaccagg gcccccgacg | 180 |
| gcactcgttt aaccacatcc gcgcctctgc tggaaacgct tgctggcgcc tgtcaccggt | 240 |
| tccctccatt ttgaaaggga aaaggctctc cccacccat tcccctgccc ctaggagctg | 300 |
| gagccggagg agccgcgctc atggcgttca gccgtggca gatcctgtcc cccgtgcagt | 360 |
| gggcgaaatg gacgtggtct gcggtacgcg gcggggccgc cggcgaggac gaggctggcg | 420 |
| ggcccgaggg cgaccccgag gaggaggatt cgcaagccga gaccaaatcc ttgagtttca | 480 |
| gctcggattc tgaaggtaat tttgagactc ctgaagctga accccgatc cgatcacctt | 540 |
| tcaaggagtc ctgtgatcca tcactcggat tggcaggacc tggggccaaa agccaagaat | 600 |
| cacaagaagc tgatgaacag cttgtagcag aagtggttga aaaatgttca tctaagactt | 660 |

```
gttctaaacc ttcagaaaat gaagtgccac agcaggccat tgactctcac tcagtcaaga    720
atttcagaga agaacctgaa catgatttta gcaaaatttc catcgtgagg ccattttcaa    780
tagaaacgaa ggattccacg gatatctcgg cagtcctcgg aacaaaagca gctcatggct    840
gtgtaactgc agtctcaggc aaggctctgc cttccagccc gccagacgcc ctccaggacg    900
aggcgatgac agaaggcagc atggggtca ccctcgaggc ctccgcagaa gctgatctaa      960
aagctggcaa ctcctgtcca gagcttgtgc ccagcagaag aagcaagctg agaaagccca   1020
agcctgtccc cctgaggaag aaagcaattg gaggagagtt ctcagacacc aacgctgctg   1080
tggagggcac acctctcccc aaggcatcct atcacttcag tcctgaagag ttggatgaga   1140
acacaagtcc tttgctagga gatgccaggt tccagaagtc tcccctgac attaaagaaa     1200 ctcccggcac tctcagtagt gacaccaacg actcaggggt tgagctgggg gaggagtcga   1260
ggagctcacc tctcaagctt gagtttgatt tcacagaaga tacaggaaac atagaggcca   1320
ggaaagccct tccaaggaag cttggcagga aactgggtag cacactgact cccaagatac   1380
aaaaagatgg catcagtaag tcagcaggtt tagaacagcc tacagaccca gtggcacgag   1440
acgggcctct ctcccaaaca tcttccaagc cagatcctag tcagtgggag agccccagct   1500 tcaaccccctt tgggagccac tctgttctgc agaactcccc acccctctct tctgagggct   1560
cctaccactt tgacccagat aactttgacg aatccatgga tcccttaaa ccaactacga     1620 ccttaacaag cagtgacttt tgttctccca ctggtaatca cgttaatgaa atcttagaat   1680
cacccaagaa ggcaaagtcg cgtttaataa cgagtggctg taaggtgaag aagcatgaaa   1740
ctcagtctct cgccctggat gcatgttctc gggatgaagg ggcagtgatc tcccagattt   1800
cagacatttc taatagggat ggccatgcta ctgatgagga gaaactggca tccacgtcat   1860
gtggtcagaa atcagctggt gccgaggtga aggtgagcc agaggaagac ctggagtact     1920
ttgaatgttc caatgttcct gtgtctacca taaatcatgc gttttcatcc tcagaagcag   1980
gcatagagaa ggagacgtgc cagaagatgg aagaagacgg gtccactgtg cttgggctgc   2040
tggagtcctc tgcagagaag gcccctgtgt cggtgtcctg tggaggtgag agccccctgg   2100
atgggatctg cctcagcgaa tcagacaaga cagccgtgct caccttaata agagaagaga   2160
taattactaa agagattgaa gcaaatgaat ggaagaagaa atacgaagag acccggcaag   2220
aagttttgga gatgaggaaa attgtagctg aatatgaaaa gactattgct caaatgattg   2280
aagatgaaca aaggacaagt atgacctctc agaagagctt ccagcaactg accatggaga   2340
aggaacaggc cctggctgac cttaactctg tggaaaggtc cctttctgat ctcttcagga   2400
gatatgagaa cctgaaaggt gttctggaag ggttcaagaa gaatgaagaa gccttgaaga   2460
aatgtgctca ggattactta gccagagtta acaagagga gcagcgatac caggccctga    2520
aaatccacgc agaagagaaa ctggacaaag ccaatgaaga gattgctcag gttcgaacaa   2580
aagcaaaggc tgagagtgca gctctccatg ctggactccg caaagagcag atgaaggtgg   2640
agtccctgga aagggccctg cagcagaaga accagaaat tgaagaactg acaaaaatct     2700
gtgatgagct gattgcaaag ctgggaaaga ctgactgaga cactccccct gttagctcaa   2760
cagatctgca tttggctgct tctcttgtga ccacaattat cttgccttat ccaggaataa   2820
ttgccccttt gcagagaaaa aaaaaaaact taaaaaagc acatgcctac tgctgcctgt      2880
cccgctttgc tgccaatgca acagccctgg aagaaaccct agagggttgc atagtctaga   2940
aaggagtgtg acctgacagt gctggagcct cctagttcc ccctatgaag gttcccttag     3000
gctgctgagt ttgggtttgt gatttatctt tagtttgttt taaagtcatc tttactttcc   3060
```

-continued

```
caaatgtgtt aaatttgtaa ctcctctttg gggtcttctc caccacctgt ctgatttttt    3120
tgtgatctgt ttaatctttt aattttttag tatcagtggt tttatttaag gagacagttt    3180
ggcctattgt tacttccaat ttataatcaa gaagggctc tggatcccct tttaaattac     3240
acacactctc acacacatac atgtatgttt atagatgctg ctgctctttt ccctgaagca    3300
tagtcaagta agaactgctc tacagaagga catatttcct tggatgtgag accctatttt   3360
gaaatagagt cctgactcag aacaccaact taagaatttg ggggattaaa gatgtgaaga    3420
ccacagtctt gggttttcat atctggagaa gactatttgc catgacgttt tgttgccctg    3480
gtatttggac actcctcagc tttaatgggt gtggcccctt taggggttagt cctcagacta    3540
atgatagtgt ctgctttctg catgaacggc aatatgggac tccctccaag ctagggtttg    3600
gcaagtctgc cctagagtca tttactctcc tctgcctcca tttgttaata cagaatcaac    3660
atttagtctt cattatcttt tttttttttt ttgagacaga gtttcgatct attttaagta    3720
tgtgaagaaa atctacttgt aaaaggctca gatcttaatt aaaaggtaat tgtagcacat    3780
taccaattat aaggtgaaga atgttttttt cccaagtgtg atgcattgtt cttcagatgt    3840
tgaaagaaa gcaaaaaata ccttctaact taagacagaa ttttaacaa aatgagcagt      3900
aaaagtcaca tgaaccactc caaaaatcag tgcattttgc atattttaa acaaagacag     3960
cttgttgaat actgagaaga ggagtgcaag gagaaggtct gtactaacaa agccaaattc    4020
ctcaagctct tactggactc agttcagagt ggtgggccat taaccccaac atggaatttt    4080
tccatataaa tctcaatgaa ttcccttca tttgaatagg caaacccaaa tccatgcaag     4140
tgttttaaag cactgtcctg tcttaatctt acatgctgaa agtcttcatg gtgatatgca    4200
ctatattcag tatacgtatg ttttcctact tctcttgtaa aactgttgca tgatccaact    4260
tcagcaatga attgtgccta gtggagaacc tctatagatc ttaaaaaatg aattattctt    4320
tagcagtgta ttactcacat gggtgcaatc tttagcccca gggaggtcaa taatgtctttt    4380
taaagccaga agtcacatt taccaatatg catttatcat aattggtgct taggctgtat     4440
attcaagcct gttgtcttaa cattttgtat aaaaagaac aacagaaatt atctgtcatt    4500
tgagaagtgg cttgacaatc atttgagctt tgaaagcagt cactgtggtg taatatgaat    4560
gctgtcctag tggtcatagt accaagggca cgtgtctccc cttggtataa ctgatttcct    4620
ttttagtcct ctactgctaa ataagttaat tttgcatttt gcagaaagaa acattgattg    4680
ctaaatcttt ttgctgctgt gttttggtgt tttcatgttt acttgtttta tattgatctg    4740
ttttaagtat gagaggctta tagtgccctc cattgtaaat ccatagtcat ctttttaagc    4800
ttattgtgtt taagaaagta gctatgtgtt aaacagaggt gatggcagcc cttccctagc    4860
acactggtgg aagagacccc ttaagaacct gaccccagtg aatgaagctg atgcacaggg    4920
acgaccaaag gaccttcgtt aagtgataat tgtcctggcc tctcagccat gaccgttatg    4980
aggaaatatc ccccattcga acttaacaga tgcctcctct ccaaagagaa ttaaaatcgt    5040
agcttgtaca gatcaagaga atatactggg cagaatgaag tatgtttgtt tattttttctt   5100
taaaaataaa ggattttgga actctggaga gtaagaatat agtatagagt ttgcctcaac    5160
acatgtgagg gccaaataac ctgctagcta ggcagtaata aactctgtta cagaagagaa    5220
aaagggccgg gcacagtggc ttattcctgt aatcccaaca ctgtgaagg ccgaggcagg    5280
aggatcactt gagtccagga gtttgaaacc tacctaggca acatggtgaa accttgtctc    5340
taccaaaata aaaattagct gggcatggtg gcacgtgcct gtggtcccag ctacttggga   5400
```

-continued

```
ggctgaggtg ggagcctggg aggtcaaggc tgcagtgagc catgatcatg ccactgcact    5460
ccatcctggg tgacagcaag atcttgtctc aaaaaaaaaa aaaaaaacca ggagtgaaaa    5520
aggaaagtag aaggcagctg ctggcctaga tgttggtttg ggaatattag gtgatcctgt    5580
tgagattctg gatccagagc aatttcttta gcttttgact ttgccaaagt gtagatagcc    5640
tttatccagc agtattttaa gtggggaatg caacgtgagg ccaactgaac aattcccccc    5700
gtggctgccc agatagtcac agtcaaggtt ggagagtctc cttccagcca gtgacctacc    5760 caaaccttt gttctgtaaa actgctctgg aaataccggg aagcccagtt ttctcacgtg    5820
gtttctagct tcttcagact cagcccaaat taggaagtgc agaagcacat gatggtgaaa    5880
aacctaggat ttggcagcct tccagaatgg tatggaatct gagggaagat ttatgtttcg    5940
ttttggagga tagctcaagt tgaatttct ttccagccag ttacccttc aacctaccca    6000 tactttgtac aactcttaca caaatactta gatatttatt agatagccct gaattcactc    6060
taattataaa cagggagtgt aaactgcccc cagatgttcc tggctgggt aaaagcagct    6120 ggagtgaagc actcattttc cataaaggta acaagggca gctcagtggt tactcaagct    6180
caaaggggtt ttttaagag caagcattgg ttaagtctgt gtatactgag ttggaagtga    6240
tttcagcaca ttctttttta gtgggagtga agttctgaa gcccccttt aacttcctct    6300 tggttttca ttataattgg tagccatctc atgaactgtc tctgactgtt gtctctttgt    6360
ggtcatgtga ttgtgagctt gctttctgac ttgcatttct gactttatcc tgttgttagg    6420
aagatagaaa ctaggttttg aaagattaca tgattcaagc gagggatttt aaagtaaaga    6480
tgtatttatt ctgaagaatc taaaagataa cagattattt gcttatgaaa gaacaatata    6540
gtctgggaat cccagaatgt caagccaaag gtctaagaag tcatctcctt caaatacttt    6600
aataaagaag tatttcgagg agatatctgt ccaaaaggt ttgactggcc tccagattcc    6660 agttatttt aaaaagcaac ttaccactaa atccttgagt ctccatagag taacagtaaa    6720
gaaactgatg taacagactc tcctctcaaa ggatctcctc tggaagagac tatcagcggc    6780
agatctctcc agggaagacc catccctag tgccagagct tgcatcctgg agactaaaga    6840
ttgcactttt ttgtagtttt ttgtccaaat gcaatcccat ttctgtgcct cttagcatgc    6900
agttagattt ggacaaacaa gattcctaag gaatgacttt attaactata atatggttac    6960
agctattata taaatatata ttctggttat agttctaata tggagatgtt gtgtgcaatg    7020
ctggcctgtg gtggtctgtg taatgcttta acttgtatgg aggaggccag gctcagagct    7080
gagatgtggc ctgaaccttc cctgtatcga tcctttaatt tagaactgtc aagatgtcac    7140
tttctccccc tctgccttt agtggtatct gacatatact caaaacagta atttcctggt    7200
cacatcatta actgctaatt ctgtatttat aaagaatttt cagatggaca tgtacaaatt    7260
tgaactcaaa ccatccccag tccagataca gggcagcgtg taggtgacca caccagagcc    7320
tcagcctcgg tccttctcag ccgtcgggat aggatccagg catttctttt aaatctcaga    7380
ggtagcagta aacttttcag tattgctgtt agcaagtgtg tgtttgccaa tagataccca    7440
ttatactaat gtgccaagta aatgttcatt gcacatctgc ttccactgtg ttcccacggg    7500
tgccatgaag tgtgtgagga gcccctcatc tggagggatg agtgctgcgt tgactactgc    7560
tatcaggatt gtgttgtgtg gaatattcat ctacataaat tttatatgca cagtaatttc    7620 ccttttata tgtcaagtaa ctatttgtaa aagttatact cacaaattat tataatgatt    7680
actaatatat ttttccatg tttcattgcc tgaataaaaa ctgtttacca ctgtta       7736
```

<210> SEQ ID NO 19
<211> LENGTH: 805
<212> TYPE: PRT
<213> ORGANISM: Homo sapiens

<400> SEQUENCE: 19

```
Met Ala Phe Ser Pro Trp Gln Ile Leu Ser Pro Val Gln Trp Ala Lys
 1               5                  10                  15

Trp Thr Trp Ser Ala Val Arg Gly Gly Ala Ala Gly Glu Asp Glu Ala
                20                  25                  30

Gly Gly Pro Glu Gly Asp Pro Glu Glu Asp Ser Gln Ala Glu Thr
            35                  40                  45

Lys Ser Leu Ser Phe Ser Ser Asp Ser Glu Gly Asn Phe Glu Thr Pro
 50                  55                  60

Glu Ala Glu Thr Pro Ile Arg Ser Pro Phe Lys Glu Ser Cys Asp Pro
 65                  70                  75                  80

Ser Leu Gly Leu Ala Gly Pro Gly Ala Lys Ser Gln Glu Ser Gln Glu
                85                  90                  95

Ala Asp Glu Gln Leu Val Ala Glu Val Val Glu Lys Cys Ser Ser Lys
            100                 105                 110

Thr Cys Ser Lys Pro Ser Glu Asn Glu Val Pro Gln Gln Ala Ile Asp
        115                 120                 125

Ser His Ser Val Lys Asn Phe Arg Glu Glu Pro Glu His Asp Phe Ser
130                 135                 140

Lys Ile Ser Ile Val Arg Pro Phe Ser Ile Glu Thr Lys Asp Ser Thr
145                 150                 155                 160

Asp Ile Ser Ala Val Leu Gly Thr Lys Ala Ala His Gly Cys Val Thr
                165                 170                 175

Ala Val Ser Gly Lys Ala Leu Pro Ser Ser Pro Asp Ala Leu Gln
            180                 185                 190

Asp Glu Ala Met Thr Glu Gly Ser Met Gly Val Thr Leu Glu Ala Ser
        195                 200                 205

Ala Glu Ala Asp Leu Lys Ala Gly Asn Ser Cys Pro Glu Leu Val Pro
210                 215                 220

Ser Arg Arg Ser Lys Leu Arg Lys Pro Lys Pro Val Pro Leu Arg Lys
225                 230                 235                 240

Lys Ala Ile Gly Gly Glu Phe Ser Asp Thr Asn Ala Ala Val Glu Gly
                245                 250                 255

Thr Pro Leu Pro Lys Ala Ser Tyr His Phe Ser Pro Glu Glu Leu Asp
            260                 265                 270

Glu Asn Thr Ser Pro Leu Leu Gly Asp Ala Arg Phe Gln Lys Ser Pro
        275                 280                 285

Pro Asp Ile Lys Glu Thr Pro Gly Thr Leu Ser Ser Asp Thr Asn Asp
290                 295                 300

Ser Gly Val Glu Leu Gly Glu Ser Arg Ser Ser Pro Leu Lys Leu
305                 310                 315                 320

Glu Phe Asp Phe Thr Glu Asp Thr Gly Asn Ile Glu Ala Arg Lys Ala
                325                 330                 335

Leu Pro Arg Lys Leu Gly Arg Lys Leu Gly Ser Thr Leu Thr Pro Lys
            340                 345                 350

Ile Gln Lys Asp Gly Ile Ser Lys Ser Ala Gly Leu Glu Gln Pro Thr
        355                 360                 365

Asp Pro Val Ala Arg Asp Gly Pro Leu Ser Gln Thr Ser Ser Lys Pro
370                 375                 380
```

-continued

```
Asp Pro Ser Gln Trp Glu Ser Pro Ser Phe Asn Pro Phe Gly Ser His
385                 390                 395                 400

Ser Val Leu Gln Asn Ser Pro Pro Leu Ser Ser Glu Gly Ser Tyr His
            405                 410                 415

Phe Asp Pro Asp Asn Phe Asp Glu Ser Met Asp Pro Phe Lys Pro Thr
        420                 425                 430

Thr Thr Leu Thr Ser Ser Asp Phe Cys Ser Pro Thr Gly Asn His Val
            435                 440                 445

Asn Glu Ile Leu Glu Ser Pro Lys Ala Lys Ser Arg Leu Ile Thr
        450                 455                 460

Ser Gly Cys Lys Val Lys His Glu Thr Gln Ser Leu Ala Leu Asp
465                 470                 475                 480

Ala Cys Ser Arg Asp Glu Gly Ala Val Ile Ser Gln Ile Ser Asp Ile
            485                 490                 495

Ser Asn Arg Asp Gly His Ala Thr Asp Glu Lys Leu Ala Ser Thr
        500                 505                 510

Ser Cys Gly Gln Lys Ser Ala Gly Ala Glu Val Lys Gly Glu Pro Glu
        515                 520                 525

Glu Asp Leu Glu Tyr Phe Glu Cys Ser Asn Val Pro Val Ser Thr Ile
530                 535                 540

Asn His Ala Phe Ser Ser Glu Ala Gly Ile Glu Lys Glu Thr Cys
545                 550                 555                 560

Gln Lys Met Glu Glu Asp Gly Ser Thr Val Leu Gly Leu Leu Glu Ser
            565                 570                 575

Ser Ala Glu Lys Ala Pro Val Ser Val Ser Cys Gly Gly Glu Ser Pro
        580                 585                 590

Leu Asp Gly Ile Cys Leu Ser Glu Ser Asp Lys Thr Ala Val Leu Thr
        595                 600                 605

Leu Ile Arg Glu Glu Ile Ile Thr Lys Glu Ile Glu Ala Asn Glu Trp
610                 615                 620

Lys Lys Lys Tyr Glu Glu Thr Arg Gln Glu Val Leu Glu Met Arg Lys
625                 630                 635                 640

Ile Val Ala Glu Tyr Glu Lys Thr Ile Ala Gln Met Ile Glu Asp Glu
            645                 650                 655

Gln Arg Thr Ser Met Thr Ser Gln Lys Ser Phe Gln Gln Leu Thr Met
        660                 665                 670

Glu Lys Glu Gln Ala Leu Ala Asp Leu Asn Ser Val Glu Arg Ser Leu
        675                 680                 685

Ser Asp Leu Phe Arg Arg Tyr Glu Asn Leu Lys Gly Val Leu Glu Gly
        690                 695                 700

Phe Lys Lys Asn Glu Glu Ala Leu Lys Lys Cys Ala Gln Asp Tyr Leu
705                 710                 715                 720

Ala Arg Val Lys Gln Glu Glu Gln Arg Tyr Gln Ala Leu Lys Ile His
            725                 730                 735

Ala Glu Glu Lys Leu Asp Lys Ala Asn Glu Glu Ile Ala Gln Val Arg
        740                 745                 750

Thr Lys Ala Lys Ala Glu Ser Ala Ala Leu His Ala Gly Leu Arg Lys
        755                 760                 765

Glu Gln Met Lys Val Glu Ser Leu Glu Arg Ala Leu Gln Gln Lys Asn
770                 775                 780

Gln Glu Ile Glu Glu Leu Thr Lys Ile Cys Asp Glu Leu Ile Ala Lys
785                 790                 795                 800

Leu Gly Lys Thr Asp
```

<210> SEQ ID NO 20
<211> LENGTH: 2781
<212> TYPE: DNA
<213> ORGANISM: Homo sapiens

<400> SEQUENCE: 20

| | |
|---|---|
| ggcggcggta gcagccaggc ttggcccccg gcgtggagca gacgcggacc cctccttcct | 60 |
| ggcggcggcg gcgcgggctc agagcccggc aacgggcggg cgggcagaat gagtctgcag | 120 |
| gtcttaaacg acaaaaatgt cagcaatgaa aaaatacaga aaaattgcga cttcctgttt | 180 |
| tcgccaccag aagttaccgg aagatcgtct gttcttcgtg tgtcacagaa agaaaatgtg | 240 |
| ccacccaaga acctggccaa agctatgaag gtgacttttc agacacctct gcgggatcca | 300 |
| cagacgcaca ggattctaag tcctagcatg ccagcaaac ttgaggctcc tttcactcag | 360 |
| gatgacaccc ttggactgga aaactcacac ccggtctgga cacagaaaga gaaccaacag | 420 |
| ctcatcaagg aagtggatgc caaaactact catggaattc tacagaaacc agtggaggct | 480 |
| gacaccgacc tcctggggga tgcaagccca gcctttggga gtggcagctc agcgagtct | 540 |
| ggcccaggtg ccctggctga cctggactgc tcaagctctt cccagagccc aggaagttct | 600 |
| gagaaccaaa tggtgtctcc aggaaaagtg tctggcagcc tgagcaagc cgtggaggaa | 660 |
| aaccttagtt cctattcctt agacagaaga gtgacacccg cctctgagac cctagaagac | 720 |
| ccttgcagga cagagtccca gcacaaagcg gagactccgc acggagccga ggaagaatgc | 780 |
| aaagcggaga ctccgcacgg agccgaggag gaatgccggc acggtggggt ctgtgctccc | 840 |
| gcagcagtgg ccacttcgcc tcctggtgca atccctaagg aagcctgcgg aggagcaccc | 900 |
| ctgcagggtc tgcctggcga agccctgggc tgccctgcgg gtgtgggcac cccgtgcca | 960 |
| gcagatggca ctcagaccct tacctgtgca cacacctctg ctcctgagag cacagcccca | 1020 |
| accaaccacc tggtggctgg cagggccatg accctgagtc ctcaggaaga agtggctgca | 1080 |
| ggccaaatgg ccagctcctc gaggagcgga cctgtaaaac tagaatttga tgtatctgat | 1140 |
| ggcgccacca gcaaaagggc acccccacca aggagactgg agagaggtc cggcctcaag | 1200 |
| cctcccttga ggaaagcagc agtgaggcag caaaaggccc cgcaggaggt ggaggaggac | 1260 |
| gacggtagga gcggagcagg agaggacccc cccatgccag cttctcgggg ctcttaccac | 1320 |
| ctcgactggg acaaaatgga tgacccaaac ttcatcccgt tcggaggtga caccaagtct | 1380 |
| ggttgcagtg aggcccagcc cccagaaagc cctgagacca ggctgggcca gccagcggct | 1440 |
| gaacagttgc atgctgggcc tgccacggag gagccaggtc cctgtctgag ccagcagctg | 1500 |
| cattcagcct cagcggagga cacgcctgtg gtgcagttgg cagccgagac cccaacagca | 1560 |
| gagagcaagg agagagcctt gaactctgcc agcacctcgc ttcccacaag ctgtccaggc | 1620 |
| agtgagccag tgcccaccca tcagcagggg cagcctgcct tggagctgaa agaggagagc | 1680 |
| ttcagagacc ccgctgaggt tctaggcacg gcgcgcgagg tggattacct ggagcagttt | 1740 |
| ggaacttcct cgtttaagga gtcggccttg aggaagcagt ccttataccct caagttcgac | 1800 |
| cccctcctga gggacagtcc tggtagacca gtgcccgtgg ccaccgagac cagcagcatg | 1860 |
| cacggtgcaa atgagactcc ctcaggacgt ccgcgggaag ccaagcttgt ggagttcgat | 1920 |
| ttcttgggag cactggacat tcctgtgcca ggcccacccc caggtgttcc cgcgcctggg | 1980 |
| ggcccacccc tgtccaccgg acctatagtg gacctgctcc agtacagcca gaaggacctg | 2040 |
| gatgcagtgg taaaggcgac acaggaggag aaccgggagc tgaggagcag gtgtgaggag | 2100 |

-continued

```
ctccacggga agaacctgga actggggaag atcatggaca ggttcgaaga ggttgtgtac    2160
caggccatgg aggaagttca gaagcagaag gaactttcca agctgaaat  ccagaaagtt    2220 ctaaaagaaa aagaccaact taccacagat ctgaactcca tggagaagtc cttctccgac    2280
ctcttcaagc gttttgagaa acagaaagag gtgatcgagg gctaccgcaa gaacgaagag    2340
tcactgaaga agtgcgtgga ggattacctg gcaaggatca cccaggaggg ccagaggtac    2400
caagccctga aggcccacgc ggaggagaag ctgcagctgg caaacgagga gatcgcccag    2460
gtccggagca aggcccaggc ggaagcgttg gccctccagg ccagcctgag gaaggagcag    2520
atgcgcatcc agtcgctgga agacacagtg gagcagaaga ctaaagagaa cgaggagctg    2580
accaggatct gcgacgacct catctccaag atggagaaga tctgacctcc acggagccgc    2640
tgtccccgcc ccctgctcc  cgtctgtctg tcctgtctga ttctcttagg tgtcatgttc    2700 tttttctgt  cttgtcttca acttttttta aaactagatt gctttgaaaa catgactcaa    2760
taaaagtttc ctttcaattt a                                              2781
```

<210> SEQ ID NO 21
<211> LENGTH: 838
<212> TYPE: PRT
<213> ORGANISM: Homo sapiens

<400> SEQUENCE: 21

```
Met Ser Leu Gln Val Leu Asn Asp Lys Asn Val Ser Asn Glu Lys Asn
 1               5                  10                  15

Thr Glu Asn Cys Asp Phe Leu Phe Ser Pro Glu Val Thr Gly Arg
            20                  25                  30

Ser Ser Val Leu Arg Val Ser Gln Lys Glu Asn Val Pro Pro Lys Asn
        35                  40                  45

Leu Ala Lys Ala Met Lys Val Thr Phe Gln Thr Pro Leu Arg Asp Pro
    50                  55                  60

Gln Thr His Arg Ile Leu Ser Pro Ser Met Ala Ser Lys Leu Glu Ala
65                  70                  75                  80

Pro Phe Thr Gln Asp Asp Thr Leu Gly Leu Glu Asn Ser His Pro Val
                85                  90                  95

Trp Thr Gln Lys Glu Asn Gln Gln Leu Ile Lys Glu Val Asp Ala Lys
            100                 105                 110

Thr Thr His Gly Ile Leu Gln Lys Pro Val Glu Ala Asp Thr Asp Leu
        115                 120                 125

Leu Gly Asp Ala Ser Pro Ala Phe Gly Ser Gly Ser Ser Ser Glu Ser
    130                 135                 140

Gly Pro Gly Ala Leu Ala Asp Leu Asp Cys Ser Ser Ser Gln Ser
145                 150                 155                 160

Pro Gly Ser Ser Glu Asn Gln Met Val Ser Pro Gly Lys Val Ser Gly
                165                 170                 175

Ser Pro Glu Gln Ala Val Glu Glu Asn Leu Ser Ser Tyr Ser Leu Asp
            180                 185                 190

Arg Arg Val Thr Pro Ala Ser Glu Thr Leu Glu Asp Pro Cys Arg Thr
        195                 200                 205

Glu Ser Gln His Lys Ala Glu Thr Pro His Gly Ala Glu Glu Glu Cys
    210                 215                 220

Lys Ala Glu Thr Pro His Gly Ala Glu Glu Glu Cys Arg His Gly Gly
225                 230                 235                 240

Val Cys Ala Pro Ala Ala Val Ala Thr Ser Pro Pro Gly Ala Ile Pro
                245                 250                 255
```

```
Lys Glu Ala Cys Gly Gly Ala Pro Leu Gln Gly Leu Pro Gly Glu Ala
                260                 265                 270
Leu Gly Cys Pro Ala Gly Val Gly Thr Pro Val Pro Ala Asp Gly Thr
            275                 280                 285
Gln Thr Leu Thr Cys Ala His Thr Ser Ala Pro Glu Ser Thr Ala Pro
        290                 295                 300
Thr Asn His Leu Val Ala Gly Arg Ala Met Thr Leu Ser Pro Gln Glu
305                 310                 315                 320
Glu Val Ala Ala Gly Gln Met Ala Ser Ser Arg Ser Gly Pro Val
                325                 330                 335
Lys Leu Glu Phe Asp Val Ser Asp Gly Ala Thr Ser Lys Arg Ala Pro
                340                 345                 350
Pro Pro Arg Arg Leu Gly Glu Arg Ser Gly Leu Lys Pro Pro Leu Arg
            355                 360                 365
Lys Ala Ala Val Arg Gln Gln Lys Ala Pro Gln Glu Val Glu Glu Asp
        370                 375                 380
Asp Gly Arg Ser Gly Ala Gly Glu Asp Pro Pro Met Pro Ala Ser Arg
385                 390                 395                 400
Gly Ser Tyr His Leu Asp Trp Asp Lys Met Asp Pro Asn Phe Ile
                405                 410                 415
Pro Phe Gly Gly Asp Thr Lys Ser Gly Cys Ser Glu Ala Gln Pro Pro
            420                 425                 430
Glu Ser Pro Glu Thr Arg Leu Gly Gln Pro Ala Ala Glu Gln Leu His
            435                 440                 445
Ala Gly Pro Ala Thr Glu Glu Pro Gly Pro Cys Leu Ser Gln Gln Leu
        450                 455                 460
His Ser Ala Ser Ala Glu Asp Thr Pro Val Val Gln Leu Ala Ala Glu
465                 470                 475                 480
Thr Pro Thr Ala Glu Ser Lys Glu Arg Ala Leu Asn Ser Ala Ser Thr
                485                 490                 495
Ser Leu Pro Thr Ser Cys Pro Gly Ser Glu Pro Val Pro Thr His Gln
            500                 505                 510
Gln Gly Gln Pro Ala Leu Glu Leu Lys Glu Glu Ser Phe Arg Asp Pro
        515                 520                 525
Ala Glu Val Leu Gly Thr Gly Ala Glu Val Asp Tyr Leu Glu Gln Phe
    530                 535                 540
Gly Thr Ser Ser Phe Lys Glu Ser Ala Leu Arg Lys Gln Ser Leu Tyr
545                 550                 555                 560
Leu Lys Phe Asp Pro Leu Leu Arg Asp Ser Pro Gly Arg Pro Val Pro
                565                 570                 575
Val Ala Thr Glu Thr Ser Ser Met His Gly Ala Asn Glu Thr Pro Ser
            580                 585                 590
Gly Arg Pro Arg Glu Ala Lys Leu Val Glu Phe Asp Phe Leu Gly Ala
        595                 600                 605
Leu Asp Ile Pro Val Pro Gly Pro Pro Gly Val Pro Ala Pro Gly
    610                 615                 620
Gly Pro Pro Leu Ser Thr Gly Pro Ile Val Asp Leu Leu Gln Tyr Ser
625                 630                 635                 640
Gln Lys Asp Leu Asp Ala Val Val Lys Ala Thr Gln Glu Glu Asn Arg
                645                 650                 655
Glu Leu Arg Ser Arg Cys Glu Glu Leu His Gly Lys Asn Leu Glu Leu
            660                 665                 670
```

```
Gly Lys Ile Met Asp Arg Phe Glu Glu Val Val Tyr Gln Ala Met Glu
        675                 680                 685

Glu Val Gln Lys Gln Lys Glu Leu Ser Lys Ala Glu Ile Gln Lys Val
690                 695                 700

Leu Lys Glu Lys Asp Gln Leu Thr Thr Asp Leu Asn Ser Met Glu Lys
705                 710                 715                 720

Ser Phe Ser Asp Leu Phe Lys Arg Phe Glu Lys Gln Lys Glu Val Ile
                725                 730                 735

Glu Gly Tyr Arg Lys Asn Glu Glu Ser Leu Lys Lys Cys Val Glu Asp
                740                 745                 750

Tyr Leu Ala Arg Ile Thr Gln Glu Gly Gln Arg Tyr Gln Ala Leu Lys
                755                 760                 765

Ala His Ala Glu Glu Lys Leu Gln Leu Ala Asn Glu Glu Ile Ala Gln
        770                 775                 780

Val Arg Ser Lys Ala Gln Ala Glu Ala Leu Ala Leu Gln Ala Ser Leu
785                 790                 795                 800

Arg Lys Glu Gln Met Arg Ile Gln Ser Leu Glu Lys Thr Val Glu Gln
                805                 810                 815

Lys Thr Lys Glu Asn Glu Glu Leu Thr Arg Ile Cys Asp Asp Leu Ile
                820                 825                 830

Ser Lys Met Glu Lys Ile
        835
```

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 22
ctgaattcat ggacctggac tctgccctcc ag                               32

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 23
gcctcgagtt agggctgctg gaacagaagg cc                               32

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 24
cgtatgcact actgtatttc ctttc                                       25

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 25

```
-continued gggcaagggc caaggtccag caatg                                        25

<210> SEQ ID NO 26
<211> LENGTH: 15
<212> TYPE: PRT
<213> ORGANISM: Homo sapiens

<400> SEQUENCE: 26

Lys Pro Ala Lys Lys Lys Lys Thr Pro Leu Lys Thr Val Lys Lys
  1               5                  10                  15

<210> SEQ ID NO 27
<211> LENGTH: 20
<212> TYPE: PRT
<213> ORGANISM: Homo sapiens

<400> SEQUENCE: 27

Met Pro Leu Arg Arg Pro Lys Met Lys Lys Thr Pro Glu Lys Leu Asp
  1               5                  10                  15

Asn Thr Pro Ala
             20

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 28
aagttttttt tttta                                                   15

<210> SEQ ID NO 29
<211> LENGTH: 13
<212> TYPE: DNA
<213> ORGANISM: Artificial Sequence
<220> FEATURE:
<223> OTHER INFORMATION: Description of Artificial Sequence: primer

<400> SEQUENCE: 29
aagcttgatt gcc                                                     13
```